(12) United States Patent
Chen et al.

(10) Patent No.: US 10,781,486 B2
(45) Date of Patent: Sep. 22, 2020

(54) METHODS, COMPOSITIONS, AND KITS COMPRISING LINKER PROBES FOR QUANTIFYING POLYNUCLEOTIDES

(71) Applicant: APPLIED BIOSYSTEMS, LLC, Carlsbad, CA (US)

(72) Inventors: Caifu Chen, Palo Alto, CA (US); Dana Ridzon, San Ramon, CA (US); Zhaohui Zhou, San Ramon, CA (US); Kai Qin Lao, Pleasanton, CA (US); Neil A. Straus, Emeryville, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 250 days.

(21) Appl. No.: 15/490,323

(22) Filed: Apr. 18, 2017

(65) Prior Publication Data

US 2017/0292158 A1    Oct. 12, 2017

Related U.S. Application Data

(60) Division of application No. 15/009,681, filed on Jan. 28, 2016, now Pat. No. 9,657,346, which is a continuation of application No. 13/612,485, filed on Sep. 12, 2012, now abandoned, which is a continuation of application No. 12/543,466, filed on Aug. 18, 2009, now Pat. No. 9,068,222, which is a continuation of application No. 10/947,460, filed on Sep. 21, 2004, now Pat. No. 7,575,863.

(60) Provisional application No. 60/575,661, filed on May 28, 2004.

(51) Int. Cl.
| | |
|---|---|
| *C12Q 1/68* | (2018.01) |
| *C07H 21/04* | (2006.01) |
| *C12P 19/34* | (2006.01) |
| *C12Q 1/6876* | (2018.01) |
| *C12N 9/00* | (2006.01) |
| *C12Q 1/686* | (2018.01) |

(52) U.S. Cl.
CPC .......... *C12Q 1/6876* (2013.01); *C07H 21/04* (2013.01); *C12N 9/00* (2013.01); *C12P 19/34* (2013.01); *C12Q 1/686* (2013.01); *C12Q 2525/301* (2013.01); *C12Q 2600/16* (2013.01); *C12Q 2600/178* (2013.01)

(58) Field of Classification Search
CPC ............ C12Q 1/6876; C12Q 2525/301; C12Q 2600/178
See application file for complete search history.

(56) References Cited

U.S. PATENT DOCUMENTS

| | | | |
|---|---|---|---|
| 4,683,202 | A | 7/1987 | Mullis |
| 4,800,159 | A | 1/1989 | Mullis et al. |
| 5,210,015 | A | 5/1993 | Gelfand et al. |
| 5,262,311 | A | 11/1993 | Pardee et al. |
| 5,538,848 | A | 7/1996 | Livak et al. |
| 5,874,260 | A | 2/1999 | Cleuziat et al. |
| 5,876,927 | A | 3/1999 | Lebo et al. |
| 5,876,930 | A | 3/1999 | Livak et al. |
| 5,882,864 | A | 3/1999 | An et al. |
| 5,952,202 | A | 9/1999 | Aoyagi et al. |
| 6,027,923 | A | 2/2000 | Wallace |
| 6,030,787 | A | 2/2000 | Livak et al. |
| 6,030,788 | A | 2/2000 | Gerhold |
| 6,037,130 | A | 3/2000 | Tyagi et al. |
| 6,040,166 | A | 3/2000 | Erlich et al. |
| 6,090,557 | A | 7/2000 | Weiss |
| 6,114,152 | A | 9/2000 | Serafini et al. |
| 6,117,635 | A | 9/2000 | Nazarenko et al. |
| 6,197,563 | B1 | 3/2001 | Erlich et al. |
| 6,258,569 | B1 | 7/2001 | Livak et al. |
| 6,270,967 | B1 | 8/2001 | Whitcombe et al. |
| 6,297,016 | B1 | 10/2001 | Egholm et al. |
| 6,358,679 | B1 | 3/2002 | Heid et al. |
| 6,403,319 | B1 | 6/2002 | Lizardi et al. |
| 6,406,891 | B1 | 6/2002 | Legerski et al. |
| 6,498,025 | B1 | 12/2002 | Miller |
| 6,548,250 | B1 | 4/2003 | Sorge et al. |

(Continued)

FOREIGN PATENT DOCUMENTS

| | | |
|---|---|---|
| EP | 1138764 | 10/2001 |
| EP | 1789591 A2 | 5/2007 |

(Continued)

OTHER PUBLICATIONS

"Stratagene Catalog", *Gene Characterization Kits*, 1988, cover and p. 39.

(Continued)

*Primary Examiner* — David C Thomas

(57) ABSTRACT

The present invention is directed to methods, reagents, kits, and compositions for identifying and quantifying target polynucleotide sequences. A linker probe comprising a 3' target specific portion, a loop, and a stem is hybridized to a target polynucleotide and extended to form a reaction product that includes a reverse primer portion and the stem nucleotides. A detector probe, a specific forward primer, and a reverse primer can be employed in an amplification reaction wherein the detector probe can detect the amplified target polynucleotide based on the stem nucleotides introduced by the linker probe. In some embodiments a plurality of short miRNAs are queried with a plurality of linker probes, wherein the linker probes all comprise a universal reverse primer portion a different 3' target specific portion and different stems. The plurality of queried miRNAs can then be decoded in a plurality of amplification reactions.

18 Claims, 6 Drawing Sheets

Specification includes a Sequence Listing.

(56) References Cited

U.S. PATENT DOCUMENTS

| | | | |
|---|---|---|---|
| 6,582,936 | B1 | 6/2003 | Serafini et al. |
| 6,605,451 | B1 | 8/2003 | Marmaro et al. |
| 6,692,915 | B1 | 2/2004 | Nallur |
| 6,764,821 | B1 | 7/2004 | Rabbani et al. |
| 6,777,180 | B1 | 8/2004 | Fisher et al. |
| 6,821,727 | B1 | 11/2004 | Livak et al. |
| 6,884,583 | B2 | 4/2005 | Livak et al. |
| 7,041,480 | B2 | 3/2006 | Abarzua |
| 7,575,863 | B2 | 8/2009 | Chen et al. |
| 7,601,495 | B2 | 10/2009 | Chen et al. |
| 7,642,055 | B2 | 1/2010 | Finn et al. |
| 8,187,815 | B2 | 5/2012 | Tan et al. |
| 8,710,208 | B2 | 4/2014 | Tan et al. |
| 9,068,222 | B2 | 6/2015 | Chen et al. |
| 9,657,346 | B2 | 5/2017 | Chen et al. |
| 2003/0050444 | A1 | 3/2003 | Haydock et al. |
| 2003/0186238 | A1 | 10/2003 | Allawi et al. |
| 2003/0186288 | A1 | 10/2003 | Spivack et al. |
| 2003/0235854 | A1 | 12/2003 | Chan et al. |
| 2004/0014058 | A1 | 1/2004 | Alsobrook et al. |
| 2004/0014129 | A1 | 1/2004 | Brown |
| 2004/0175732 | A1 | 9/2004 | Rana |
| 2004/0203061 | A1 | 10/2004 | Barany et al. |
| 2004/0214196 | A1 | 10/2004 | Aydin |
| 2005/0059049 | A1 | 3/2005 | Moen et al. |
| 2005/0074788 | A1 | 4/2005 | Dahlberg et al. |
| 2005/0245475 | A1 | 11/2005 | Khvorova et al. |
| 2005/0255487 | A1 | 11/2005 | Khvorova et al. |
| 2005/0260640 | A1 | 11/2005 | Andersen et al. |
| 2005/0266418 | A1 | 12/2005 | Chen et al. |
| 2005/0272071 | A1 | 12/2005 | Lao et al. |
| 2005/0272075 | A1 | 12/2005 | Jacobsen et al. |
| 2006/0035215 | A9 | 2/2006 | Sorge et al. |
| 2006/0035217 | A1 | 2/2006 | Livak et al. |
| 2006/0057595 | A1 | 3/2006 | Lao et al. |
| 2006/0063163 | A1 | 3/2006 | Chen et al. |
| 2006/0078924 | A1 | 4/2006 | Finn et al. |
| 2006/0194225 | A1 | 8/2006 | Spier |
| 2007/0015176 | A1 | 1/2007 | Lao et al. |
| 2007/0048757 | A1 | 3/2007 | Lao et al. |
| 2007/0111226 | A1 | 5/2007 | Tan et al. |
| 2007/0178459 | A1 | 8/2007 | Millar et al. |
| 2009/0087858 | A1 | 4/2009 | Finn et al. |
| 2010/0112573 | A1 | 5/2010 | Chen et al. |
| 2010/0203545 | A1 | 8/2010 | Finn et al. |
| 2013/0011840 | A1 | 1/2013 | Chen et al. |
| 2014/0377748 | A1 | 12/2014 | Tan et al. |

FOREIGN PATENT DOCUMENTS

| | | |
|---|---|---|
| EP | 1791982 | 6/2007 |
| EP | 2186908 A1 | 5/2010 |
| EP | 1791982 B1 | 1/2011 |
| EP | 1924713 B1 | 11/2011 |
| WO | WO-1998/35058 | 8/1998 |
| WO | WO-1999/007896 | 2/1999 |
| WO | WO-2000079009 | 12/2000 |
| WO | WO-2001/94634 | 12/2001 |
| WO | WO-2002061143 | 8/2002 |
| WO | WO-2002/090561 | 11/2002 |
| WO | WO 2003/102232 | 12/2003 |
| WO | WO 2004/022784 | 3/2004 |
| WO | WO 2004/057017 | 7/2004 |
| WO | WO 2005/094532 | 10/2005 |
| WO | WO 2006/034387 | 3/2006 |
| WO | WO-2006033928 A2 | 3/2006 |
| WO | WO-2007025281 A2 | 3/2007 |

OTHER PUBLICATIONS

"Supplemental EP Search Report for 06850497.6", dated Dec. 22, 2008.
"Supplemental EP Search Report for application No. 06802531.1", dated Dec. 17, 2008.
090160607, "Extended European search report dated Apr. 8, 2010", 9.
Allawi, Hatim T. et al., "Quantitation of MicroRNAs Using a Modified Invader Assay",*RNA, Cold Spring Harbor Laboratory Press, Woodbury, NY*, vol. 10 (7), Jul. 2004, 1153-1161.
Brennecke, et al., "Towards a Complete Description of the microRNA Complement of Animal Genomes", *Genome Biology*, vol. 4, No. 9, 2003, 228.1-228.3.
Chen, C et al., "Real-time PCR: advancing RNA interference and microRNA studies", *Pharmaceutical Discovery, Advanstar,Communications, Inc., Duluth, MN, US*, XP082364909,ISSN: 1554-2068, May 1, 2005, 5 pages.
Chen, C. et al., "Real-time quantification of microRNAs by stem-loop RT-PCR", *Nucleic Acids Research*, vol. 33(20), 2005, pp. 1-9
Eggerding, F. A. et al., "A One-Step Coupled Amplification and Oligonucleotide Ligation Procedure for Multiplex Genetic Typing", *PCR Methods &Applications,Cold Spring Harbor Laboratory Press, US,*, vol. 4, No. 6, 1995, 337-345.
Eldering, E. et al., "Expression profiling via novel multiplex assay allows rapid assessment of gene regulation in defined signalling pathways", *Nucleic Acids Research*, vol. 31, No. 23, pp. 1362-4962, Dec. 1, 2003, p. 153.
EP Patent App. 06802531.1, "Supplementary Search Report dated Nov. 27, 2008", 5 Pgs.
EP Patent App. 06850497.6, "Supplementary Search Report dated Dec. 1, 2008", 3 Pgs.
Grad, Y. et al., "Computational and Experimental Identification of C. Elegans MicroRNAs", *Molecular Cell, Cell Press, Cambridge, MA*, vol. 11 (5), May 2003, 1253-1263.
Guegler, et al., "Quantitation of Plant miRNAs by RT-PCR", http://www.gene-quantification.de/guegler-AB.pdf, Feb. 2, 2006, 1 page.
Heid, et al., "Real Time Quantitative PCR", *Genome Research, Cold Spring Harbor Laboratory Press, Woodbury, NY*, vol. 6 (10), Oct. 1996, 986-994.
Lane, M et al., "The Thermodynamic Advantage of DNA oligo-nucleotide 'stacking hybridization' reactions: Energetics of a DNA Nick", *Nucleic Acids Research* vol. 25(1): 611-616, 1997.
Lao, K. et al., "Multiplexing RT-PCR for the detection of multiple miRNA species in small samples", *Biochemical and Biophysical Research Communications*,343(1), Feb. 28, 2006, 85-89.
Liang, D-C et al., "Multiplex RT-PCR assay for the detection of major fusion transcripts in Taiwanese children with B-lineage acute lymphoblastic leukemia", *Medical and Pediatric Oncology*, vol. 39, No. 7,XP002506296; ISSN: 0098-1532, Jul. 2002, 12-17.
PCT/US025/33943, "PCT Search Report dated Feb. 21, 2006", 3.
PCT/US06/33942, "International Search Report", PCT/US06/33642 dated Sep. 5, 2007, 4.
PCT/US2005/033943, "International Search Report received for PCT Application No. PCT/US2005/033943 dated Feb. 21, 2006", 1-15.
PCT/US2006/021172, "International Search Report dated Aug. 9, 2007", 1 Pg.
Schmittgen, T. D. et al., "A high-throughput method to monitor the expression of microRNA precursors", *Nucleic Acids Research*, vol. 32 (4), Feb. 25, 2004, pp. 1-10.
Stratagene Catalog 1988, "Stragagene Cloning Systems: Tools and Technology for Life Sciences", *Gene Characterization Kits*, Jan. 1, 1988, 39.
Tse, W. T. et al., "Reverse Transcription and Direct Amplification of Cellular RNA Transcripts by TAQ Polymerase", *Gene. Elsevier, Amsterdam. NL*,XP000226751, vol. 88, No. 2,I SSN: 0378-1119, Apr. 16, 1990, 293-296.
Ambros et al., "MicroRNAs and Other Tiny Enfogenous RNAs in C. elegans", Current Biology, vol. 13, Issue 10, May 13, 2003, 807-818.
Bentwich, et al., "Identification of hundreds of conserved and nonconserved human micro RNAs", Nature Genetics, vol. 37, No. 7, Jun. 19, 2005, 766-770.
Detecting miRNA & siRNA—Sensitive Solution Hybridization Assay for Small RNAs Ambion, Inc., Tech Notes, vol. 10, No. 4, material obtained from company website on Aug. 16, 2005, pp. 1-8.

(56) References Cited

OTHER PUBLICATIONS

L. Beauchamp et al., "New Tools for miRNA and siRNA Analysis" Ambion, Inc., Product Information Poster, material obtained online from company website on Aug. 16, 2005, 8 pgs.

L. Lim et al., "The microRNAs of Caenorhabditis elegans" Genes & Development, vol. 17, (2003), pp. 991-1008.

Lagos-Quintana et al, "Identification of novel genes coding for small expressed RNAs," Science, vol. 294, No. 5543, 2001, pp. 853-858.

Lagos-Quintana, et al., "New microRNAs from mouse and human", RNA vol. 9, No. 2, Feb. 2003, 175-179.

Lau et al., RNA Cloning Method Flowchart, Science 2001, vol. 294, pp. 858-862, Bartel Lab Protocol, pp. 1-9.

Ortiz et al., PNA molecular beacons for rapid detection of PCR amplicons. Mole. Cell. Probes 12, 219-226, Aug. 1998.

METHODS, COMPOSITIONS, AND KITS COMPRISING LINKER PROBES FOR QUANTIFYING POLYNUCLEOTIDES

RELATED APPLICATIONS

This application is a division of U.S. application Ser. No. 15/009,681, filed Jan. 28, 2016, now U.S. Pat. No. 9,657, 346, which is a continuation of U.S. application Ser. No. 13/612,485, filed Sep. 12, 2012, now abandoned, which is a continuation of U.S. application Ser. No. 12/543,466, filed Aug. 18, 2009, now U.S. Pat. No. 9,068,222, which is a continuation of U.S. application Ser. No. 10/947,460, filed Sep. 21, 2004, now U.S. Pat. No. 7,575,863, which claims the benefit of U.S. Provisional Application 60/575,661, filed May 28, 2004, each of which is incorporated herein by reference in its entirety.

SEQUENCE LISTING

The instant application contains a Sequence Listing which has been submitted via EFS-Web and is hereby incorporated by reference in its entirety. Said ASCII copy, created on Jan. 6, 2009, is named 533USC1.txt, and is 118,670 bytes in size.

FIELD

The present teachings are in the field of molecular and cell biology, specifically in the field of detecting target polynucleotides such as miRNA.

INTRODUCTION

RNA interference (RNAi) is a highly coordinated, sequence-specific mechanism involved in posttranscriptional gene regulation. During the initial steps of process, a ribonuclease (RNase) II-like enzyme called Dicer reduces long double-strand RNA (dsRNA) and complex hairpin precursors into: 1) small interfering RNAs (siRNA) that degrade messenger RNA (mRNA) and 2) micro RNAs (miRNAs) that can target mRNAs for cleavage or attenuate translation.

The siRNA class of molecules is thought to be comprised of 21-23 nucleotide (nt) duplexes with characteristic dinucleotide 3' overhangs (Ambros et al., 2003, RNA, 9 (3), 277-279). siRNA has been shown to act as the functional intermediate in RNAi, specifically directing cleavage of complementary mRNA targets in a process that is commonly regarded to be an antiviral cellular defense mechanism (Elbashir et al., 2001, Nature, 411:6836), 494-498, Elbashir et al., 2001, Genes and Development, 15 (2), 188-200). Target RNA cleavage is catalyzed by the RNA-induced silencing complex (RISC), which functions as a siRNA directed endonuclease (reviewed in Bartel, 2004, Cell, 116 (2), 281-297).

Micro RNAs (miRNAs) typically comprise single-stranded, endogenous oligoribonucleotides of roughly 22 (18-25) bases in length that are processed from larger stem-looped precursor RNAs. The first genes recognized to encode miRNAs, lin-4 and let-7 of C. elegans, were identified on the basis of the developmental timing defects associated with the loss-of-function mutations (Lee et al., 1993, Cell, 75 (5), 843-854; Reinhart et al., 2000, Nature, 403, (6772), 901-906; reviewed by Pasquinelli et al., 2002, Annual Review of Cell and Developmental Biology, 18, 495-513). The breadth and importance of miRNA-directed gene regulation are coming into focus as more miRNAs and regulatory targets and functions are discovered. To date, a total of at least 700 miRNAs have been identified in C. elegans, Drosophila (Fire et al., 1998, Nature, 391 (6669 (805-811), mouse, human (Lagos-Quintana et al., 2001, Science, 294 (5543), 853-858), and plants (Reinhart et al., 2002, Genes and Development, 16 (13), 1616-1626). Their sequences are typically conserved among different species. Size ranges from 18 to 25 nucleotides for miRNAs are the most commonly observed to date.

The function of most miRNAs is not known. Recently discovered miRNA functions include control of cell proliferation, cell death, and fat metabolism in flies (Brennecke et al., 2003, cell, 113 (1), 25-36; Xu et al, 2003, Current Biology, 13 (9), 790-795), neuronal patterning in nematodes (Johnston and Hobert, 2003, Nature, 426 (6968), 845-849), modulation of hematopoietic lineage differentiation in mammals (Chen et al., 2004, Science, 303 (5654), 83-87), and control of leaf and flower development in plants (Aukerman and Sakai, 2003, Plant Cell, 15 (11), 2730-2741; Chen, 2003, Science, 303 (5666):2022-2025; Emery et al., 2003, Current Biology, 13 (20), 1768-1774; Palatnik et al., 2003, Nature, 425 (6955), 257-263). There is speculation that miRNAs may represent a new aspect of gene regulation.

Most miRNAs have been discovered by cloning. There are few cloning kits available for researchers from Ambion and QIAGEN etc. The process is laborious and less accurate. Further, there has been little reliable technology available for miRNA quantitation (Allawi et al., Third Wave Technologies, R N A. 2004 July; 10(7):1153-61). Northern blotting has been used but results are not quantitative (Lagos-Quitana et al., 2001, Science, 294 (5543), 853-854). Many miRNA researchers are interested in monitoring the level of the miRNAs at different tissues, at the different stages of development, or after treatment with various chemical agents. However, the short length of miRNAs has their study difficult.

SUMMARY

In some embodiments, the present teachings provide a method for detecting a micro RNA (miRNA) comprising; hybridizing the miRNA and a linker probe, wherein the linker probe comprises a stem, a loop, and a 3' target-specific portion, wherein the 3' target-specific portion base pairs with the 3' end region of the miRNA; extending the linker probe to form an extension reaction product; amplifying the extension reaction product to form an amplification product; and, detecting the miRNA.

In some embodiments, the present teachings provide a method for detecting a target polynucleotide comprising; hybridizing the target polynucleotide and a linker probe, wherein the linker probe comprises a stem, a loop, and a 3' target-specific portion, wherein the 3' target-specific portion base pairs with the 3' end region of the target polynucleotide; extending the linker probe to form an extension reaction product; amplifying the extension reaction product to form an amplification product in the presence of a detector probe, wherein the detector probe comprises a nucleotide of the linker probe stem in the amplification product or a nucleotide of the linker probe stem complement in the amplification product; and, detecting the target polynucleotide.

In some embodiments, the present teachings provide a method for detecting a miRNA molecule comprising; hybridizing the miRNA molecule and a linker probe, wherein the linker probe comprises a stem, a loop, and a 3' target specific portion, wherein the 3' target-specific portion base pairs with the 3' end region of the target polynucleotide;

extending the linker probe to form an extension reaction product; amplifying the extension reaction product in the presence of a detector probe to form an amplification product, wherein the detector probe comprises a nucleotide of the linker probe stem in the amplification product or a nucleotide of the linker probe stem complement in the amplification product, and the detector probe further comprises a nucleotide of the 3' end region of the miRNA in the amplification product or a nucleotide of the 3' end region of the miRNA complement in the amplification product; and, detecting the miRNA molecule.

In some embodiments, the present teachings provide a method for detecting two different miRNAs from a single hybridization reaction comprising; hybridizing a first miRNA and a first linker probe, and a second miRNA and a second linker probe, wherein the first linker probe and the second linker probe each comprise a loop, a stem, and a 3' target-specific portion, wherein the 3' target-specific portion of the first linker probe base pairs with the 3' end region of the first miRNA, and wherein the 3' target-specific portion of the second linker probe base pairs with the 3' end region of the second miRNA; extending the first linker probe and the second linker probe to form extension reaction products; dividing the extension reaction products into a first amplification reaction to form a first amplification reaction product, and a second amplification reaction to form a second amplification reaction product, wherein a primer in the first amplification reaction corresponds with the first miRNA and not the second miRNA, and a primer in the second amplification reaction corresponds with the second miRNA and not the first miRNA, wherein a first detector probe in the first amplification reaction differs from a second detector probe in the second amplification reaction, wherein the first detector probe comprises a nucleotide of the first linker probe stem of the amplification product or a nucleotide of the first linker probe stem complement in the first amplification product, wherein the second detector probe comprises a nucleotide of the second linker probe stem of the amplification product or a nucleotide of the second linker probe stem complement in the amplification product; and, detecting the two different miRNAs.

In some embodiments, the present teachings provide a method for detecting two different target polynucleotides from a single hybridization reaction comprising; hybridizing a first target polynucleotide and a first linker probe, and a second target polynucleotide and a second linker probe, wherein the first linker probe and the second linker probe each comprise a loop, a stem, and a 3' target-specific portion, wherein the 3' target-specific portion of the first linker probe base pairs with the 3' end region of the first target polynucleotide, and wherein the 3' target-specific portion of the second linker probe base pairs with the 3' end region of the second target polynucleotide; extending the first linker probe and the second linker probe to form extension reaction products; dividing the extension reaction products into a first amplification reaction to form a first amplification reaction product and a second amplification reaction to form a second amplification reaction product; and, detecting the two different miRNA molecules.

In some embodiments, the present teachings provide a method for detecting a miRNA molecule from a cell lysate comprising; hybridizing the miRNA molecule from the cell lysate with a linker probe, wherein the linker probe comprises a stem, a loop, and a 3' target specific portion, wherein the 3' target-specific portion base pairs with the 3' end region of the miRNA; extending the linker probe to form an extension reaction product; amplifying the extension reaction product to form an amplification product in the presence of a detector probe, wherein the detector probe comprises a nucleotide of the linker probe stem of the amplification product or a nucleotide of the linker probe stem complement in the amplification product, and the detector probe further comprises a nucleotide of the 3' end region of the miRNA in the amplification product or a nucleotide of the 3' end region of the miRNA complement in the amplification product; and, detecting the miRNA molecule.

A kit comprising; a reverse transcriptase and a linker probe, wherein the linker probe comprises a stem, a loop, and a 3' target-specific portion, wherein the 3' target-specific portion corresponds to a miRNA.

The present teachings contemplate method for detecting a miRNA molecule comprising a step of hybridizing, a step of extending, a step of amplifying, and a step of detecting.

These and other features of the present teachings are set forth herein.

BRIEF DESCRIPTION OF THE DRAWINGS

The skilled artisan will understand that the drawings, described below, are for illustration purposes only. The drawings are not intended to limit the scope of the present teachings in any way.

FIG. 3 depicts SEQ ID No. 780, the oligonucleotide for the micro RNA MiR-16 (boxed, 11) and a linker probe (13).

DESCRIPTION OF EXEMPLARY EMBODIMENTS

Figure 1A:
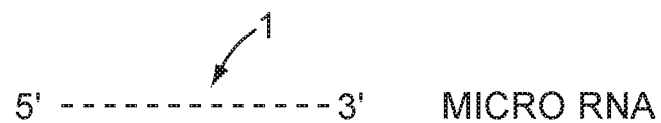
FIGS. 1A, 1B, and 1C depict certain aspects of various compositions according to some embodiments of the present teachings.

Aspects of the present teachings may be further understood in light of the following examples, which should not be construed as limiting the scope of the present teachings in any way. The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. For example, "a primer" means that more than one primer can, but need not, be present; for example but without limitation, one or more copies of a particular primer species, as well as one or more versions of a particular primer type, for example but not limited to, a multiplicity of different forward primers. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive of the invention.

Some Definitions

As used herein, the term "target polynucleotide" refers to a polynucleotide sequence that is sought to be detected. The target polynucleotide can be obtained from any source, and can comprise any number of different compositional components. For example, the target can be nucleic acid (e.g. DNA or RNA), transfer RNA, siRNA, and can comprise nucleic acid analogs or other nucleic acid mimic. The target can be methylated, non-methylated, or both. The target can be bisulfite-treated and non-methylated cytosines converted to uracil. Further, it will be appreciated that "target polynucleotide" can refer to the target polynucleotide itself, as well as surrogates thereof, for example amplification products, and native sequences. In some embodiments, the target polynucleotide is a miRNA molecule. In some embodiments, the target polynucleotide lacks a poly-A tail. In some embodiments, the target polynucleotide is a short DNA molecule derived from a degraded source, such as can be found in for example but not limited to forensics samples (see for example Butler, 2001, *Forensic DNA Typing: Biology and Technology Behind STR Markers*. The target polynucleotides of the present teachings can be derived from any of a number of sources, including without limitation, viruses, prokaryotes, eukaryotes, for example but not limited to plants, fungi, and animals. These sources may include, but are not limited to, whole blood, a tissue biopsy, lymph, bone marrow, amniotic fluid, hair, skin, semen, biowarfare agents, anal secretions, vaginal secretions, perspiration, saliva, buccal swabs, various environmental samples (for example, agricultural, water, and soil), research samples generally, purified samples generally, cultured cells, and lysed cells. It will be appreciated that target polynucleotides can be isolated from samples using any of a variety of procedures known in the art, for example the Applied Biosystems ABI Prism™ 6100 Nucleic Acid PrepStation, and the ABI Prism™ 6700 Automated Nucleic Acid Workstation, Boom et al., U.S. Pat. No. 5,234,809, mirVana RNA isolation kit (Ambion), etc. It will be appreciated that target polynucleotides can be cut or sheared prior to analysis, including the use of such procedures as mechanical force, sonication, restriction endonuclease cleavage, or any method known in the art. In general, the target polynucleotides of the present teachings will be single stranded, though in some embodiments the target polynucleotide can be double stranded, and a single strand can result from denaturation.

As used herein, the term "3' end region of the target polynucleotide" refers to the region of the target to which the 3' target specific portion of the linker probe hybridizes. In some embodiments there can be a gap between the 3' end region of the target polynucleotide and the 5' end of the linker probe, with extension reactions filling in the gap, though generally such scenarios are not preferred because of the likely destabilizing effects on the duplex. In some embodiments, a miRNA molecule is the target, in which case the term "3' end region of the miRNA" is used.

As used herein, the term "linker probe" refers to a molecule comprising a 3' target specific portion, a stem, and a loop. Illustrative linker probes are depicted in FIGS. 2A-2D and elsewhere in the present teachings. It will be appreciated that the linker probes, as well as the primers of the present teachings, can be comprised of ribonucleotides, deoxynucleotides, modified ribonucleotides, modified deoxyribonucleotides, modified phosphate-sugar-backbone oligonucleotides, nucleotide analogs, or combinations thereof. For some illustrative teachings of various nucleotide analogs etc, see Fasman, 1989, Practical Handbook of Biochemistry and Molecular Biology, pp. 385-394, CRC Press, Boca Raton, Fla., Loakes, N. A. R. 2001, vol 29:2437-2447, and Pellestor et al., Int J Mol Med. 2004 April; 13(4):521-5.), references cited therein, and recent articles citing these reviews. It will be appreciated that the selection of the linker probes to query a given target polynucleotide sequence, and the selection of which collection of target polynucleotide sequences to query in a given reaction with which collection of linker probes, will involve procedures generally known in the art, and can involve the use of algorithms to select for those sequences with minimal secondary and tertiary structure, those targets with minimal sequence redundancy with other regions of the genome, those target regions with desirable thermodynamic characteristics, and other parameters desirable for the context at hand.

As used herein, the term "3' target-specific portion" refers to the single stranded portion of a linker probe that is complementary to a target polynucleotide. The 3' target-specific portion is located downstream from the stem of the linker probe. Generally, the 3' target-specific portion is between 6 and 8 nucleotides long. In some embodiments, the 3' target-specific portion is 7 nucleotides long. It will be appreciated that routine experimentation can produce other lengths, and that 3' target-specific portions that are longer than 8 nucleotides or shorter than 6 nucleotides are also contemplated by the present teachings. Generally, the 3'-most nucleotides of the 3' target-specific portion should have minimal complementarity overlap, or no overlap at all, with the 3' nucleotides of the forward primer; it will be appreciated that overlap in these regions can produce undesired primer dimer amplification products in subsequent amplification reactions. In some embodiments, the overlap between the 3'-most nucleotides of the 3' target-specific portion and the 3' nucleotides of the forward primer is 0, 1, 2, or 3 nucleotides. In some embodiments, greater than 3 nucleotides can be complementary between the 3'-most nucleotides of the 3' target-specific portion and the 3' nucleotides of the forward primer, but generally such scenarios will be accompanied by additional non-complementary nucleotides interspersed therein. In some embodiments, modified bases such as LNA can be used in the 3' target specific portion to increase the Tm of the linker probe (see for example Petersen et al., Trends in Biochemistry (2003), 21:2:74-81). In some embodiments, universal bases can be used, for example to allow for smaller libraries of linker probes. Universal bases can also be used in the 3' target specific portion to allow for the detection of unknown targets. For some descriptions of universal bases, see for example Loakes et al., Nucleic Acids Research, 2001, Volume 29, No. 12, 2437-2447. In some embodiments, modifications including but not limited to LNAs and universal bases can improve reverse transcription specificity and potentially enhance detection specificity.

As used herein, the term "stem" refers to the double stranded region of the linker probe that is between the 3' target-specific portion and the loop. Generally, the stem is between 6 and 20 nucleotides long (that is, 6-20 complementary pairs of nucleotides, for a total of 12-40 distinct nucleotides). In some embodiments, the stem is 8-14 nucleotides long. As a general matter, in those embodiments in which a portion of the detector probe is encoded in the stem, the stem can be longer. In those embodiments in which a portion of the detector probe is not encoded in the stem, the stem can be shorter. Those in the art will appreciate that stems shorter that 6 nucleotides and longer than 20 nucleotides can be identified in the course of routine methodology and without undue experimentation, and that such shorter and longer stems are contemplated by the present teachings. In some embodiments, the stem can comprise an identifying portion.

Figure 1B:
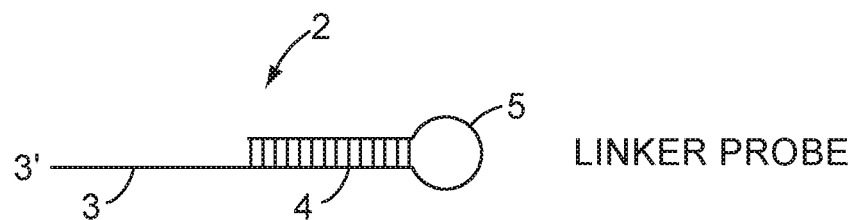
Figure 1C:
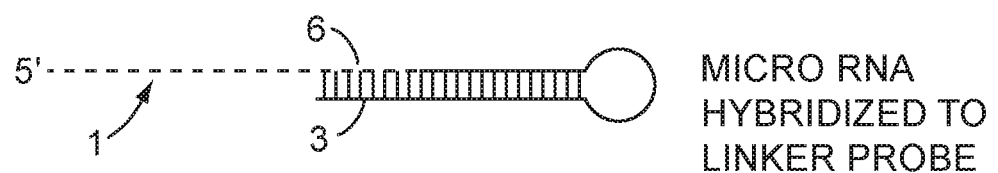

As used herein, the term "loop" refers to a region of the linker probe that is located between the two complementary strands of the stem, as depicted in FIGS. 1A-1C and elsewhere in the present teachings. Typically, the loop comprises single stranded nucleotides, though other moieties modified DNA or RNA, Carbon spacers such as C18, and/or PEG (polyethylene glycol) are also possible. Generally, the loop is between 4 and 20 nucleotides long. In some embodiments, the loop is between 14 and 18 nucleotides long. In some embodiments, the loop is 16 nucleotides long. As a general matter, in those embodiments in which a reverse primer is encoded in the loop, the loop can generally be longer. In those embodiments in which the reverse primer corresponds to both the target polynucleotide as well as the loop, the loop can generally be shorter. Those in the art will appreciate that loops shorter that 4 nucleotides and longer than 20 nucleotides can be identified in the course of routine methodology and without undue experimentation, and that such shorter and longer loops are contemplated by the present teachings. In some embodiments, the loop can comprise an identifying portion.

As used herein, the term "identifying portion" refers to a moiety or moieties that can be used to identify a particular linker probe species, and as a result determine a target polynucleotide sequence, and can refer to a variety of distinguishable moieties including zipcodes, a known number of nucleobases, and combinations thereof. In some embodiments, an identifying portion, or an identifying portion complement, can hybridize to a detector probe, thereby allowing detection of a target polynucleotide sequence in a decoding reaction. The terms "identifying portion complement" typically refers to at least one oligonucleotide that comprises at least one sequence of nucleobases that are at least substantially complementary to and hybridize with their corresponding identifying portion. In some embodiments, identifying portion complements serve as capture moieties for attaching at least one identifier portion:element complex to at least one substrate; serve as "pull-out" sequences for bulk separation procedures; or both as capture moieties and as pull-out sequences (see for example O'Neil, et al., U.S. Pat. Nos. 6,638,760, 6,514,699, 6,146,511, and 6,124,092). Typically, identifying portions and their corresponding identifying portion complements are selected to minimize: internal, self-hybridization; cross-hybridization with different identifying portion species, nucleotide sequences in a reaction composition, including but not limited to gDNA, different species of identifying portion complements, or target-specific portions of probes, and the like; but should be amenable to facile hybridization between the identifying portion and its corresponding identifying portion complement. Identifying portion sequences and identifying portion complement sequences can be selected by any suitable method, for example but not limited to, computer algorithms such as described in PCT Publication Nos. WO 96/12014 and WO 96/41011 and in European Publication No. EP 799,897; and the algorithm and parameters of SantaLucia (Proc. Natl. Acad. Sci. 95:1460-65 (1998)). Descriptions of identifying portions can be found in, among other places, U.S. Pat. No. 6,309,829 (referred to as "tag segment" therein); U.S. Pat. No. 6,451,525 (referred to as "tag segment" therein); U.S. Pat. No. 6,309,829 (referred to as "tag segment" therein); U.S. Pat. No. 5,981,176 (referred to as "grid oligonucleotides" therein); U.S. Pat. No. 5,935,793 (referred to as "identifier tags" therein); and PCT Publication No. WO 01/92579 (referred to as "addressable support-specific sequences" therein). In some embodiments, the stem of the linker probe, the loop of the linker probe, or combinations thereof can comprise an identifying portion, and the detector probe can hybridize to the corresponding identifying portion. In some embodiments, the detector probe can hybridize to both the identifying portion as well as sequence corresponding to the target polynucleotide. In some embodiments, at least two identifying portion: identifying portion complement duplexes have melting temperatures that fall within a $\Delta T_m$ range ($T_{max}$-$T_{min}$) of no more than 10° C. of each other. In some embodiments, at least two identifying portion: identifying portion complement duplexes have melting temperatures that fall within a $\Delta T_m$ range of 5° C. or less of each other. In some embodiments, at least two identifying portion: identifying portion complement duplexes have melting temperatures that fall within a $\Delta T_m$ range of 2° C. or less of each other. In some embodiments, at least one identifying portion or at least one identifying portion complement is used to separate the element to which it is bound from at least one component of a ligation reaction composition, a digestion reaction composition, an amplified ligation reaction composition, or the like. In some embodiments, identifying portions are used to attach at least one ligation product, at least one ligation product surrogate, or combinations thereof, to at least one substrate. In some embodiments, at least one ligation product, at least one ligation product surrogate, or combinations thereof, comprise the same identifying portion. Examples of separation approaches include but are not limited to, separating a multiplicity of different element: identifying portion species using the same identifying portion complement, tethering a multiplicity of different element: identifying portion species to a substrate comprising the same identifying portion complement, or both. In some embodiments, at least one identifying portion complement comprises at least one label, at least one mobility modifier, at least one label binding portion, or combinations thereof. In some embodiments, at least one identifying portion complement is annealed to at least one corresponding identifying portion and, subsequently, at least part of that identifying portion complement is released and detected, see for example Published P.C.T. Application WO04/4634 to Rosenblum et al., and Published P.C.T. Application WO01/92579 to Wenz et al., As used herein, the term "extension reaction" refers to an elongation reaction in which the 3' target specific portion of a linker probe is extended to form an extension reaction product comprising a strand complementary to the target polynucleotide. In some embodiments, the target polynucleotide is a miRNA molecule and the extension reaction is a reverse transcription reaction comprising a reverse transcriptase. In some embodiments, the extension reaction is a reverse transcription reaction comprising a polymerase derived from a Eubacteria. In some embodiments, the extension reaction can comprise rTth polymerase, for example as commercially available from Applied Biosystems catalog number N808-0192, and N808-0098. In some embodiments, the target polynucleotide is a miRNA or other RNA molecule, and as such it will be appreciated that the use of polymerases that also comprise reverse transcription properties can allow for some embodiments of the present teachings to comprise a first reverse transcription reaction followed thereafter by an amplification reaction, thereby allowing for the consolidation of two reactions in essentially a single reaction. In some embodiments, the target polynucleotide is a short DNA molecule and the extension reaction comprises a polymerase and results in the synthesis of a $2^{nd}$ strand of DNA. In some embodiments, the consolidation of the extension reaction and a subsequent amplification reaction is further contemplated by the present teachings.

As used herein, the term "primer portion" refers to a region of a polynucleotide sequence that can serve directly, or by virtue of its complement, as the template upon which a primer can anneal for any of a variety of primer nucleotide extension reactions known in the art (for example, PCR). It will be appreciated by those of skill in the art that when two primer portions are present on a single polynucleotide, the orientation of the two primer portions is generally different. For example, one PCR primer can directly hybridize to a first primer portion, while the other PCR primer can hybridize to the complement of the second primer portion. In addition, "universal" primers and primer portions as used herein are generally chosen to be as unique as possible given the particular assays and host genomes to ensure specificity of the assay.

As used herein, the term "forward primer" refers to a primer that comprises an extension reaction product portion and a tail portion. The extension reaction product portion of the forward primer hybridizes to the extension reaction product. Generally, the extension reaction product portion of the forward primer is between 9 and 19 nucleotides in length. In some embodiments, the extension reaction product portion of the forward primer is 16 nucleotides. The tail portion is located upstream from the extension reaction product portion, and is not complementary with the extension reaction product; after a round of amplification however, the tail portion can hybridize to complementary sequence of amplification products. Generally, the tail portion of the forward primer is between 5-8 nucleotides long. In some embodiments, the tail portion of the forward primer is 6 nucleotides long. Those in the art will appreciate that forward primer tail portion lengths shorter than 5 nucleotides and longer than 8 nucleotides can be identified in the course of routine methodology and without undue experimentation, and that such shorter and longer forward primer tail portion lengths are contemplated by the present teachings. Further, those in the art will appreciate that lengths of the extension reaction product portion of the forward primer shorter than 9 nucleotides in length and longer than 19 nucleotides in length can be identified in the course of routine methodology and without undue experimentation, and that such shorter and longer extension reaction product portion of forward primers are contemplated by the present teachings.

As used herein, the term "reverse primer" refers to a primer that when extended forms a strand complementary to the target polynucleotide. In some embodiments, the reverse primer corresponds with a region of the loop of the linker probe. Following the extension reaction, the forward primer can be extended to form a second strand product. The reverse primer hybridizes with this second strand product, and can be extended to continue the amplification reaction.

In some embodiments, the reverse primer corresponds with a region of the loop of the linker probe, a region of the stem of the linker probe, a region of the target polynucleotide, or combinations thereof. Generally, the reverse primer is between 13-16 nucleotides long. In some embodiments the reverse primer is 14 nucleotides long. In some embodiments, the reverse primer can further comprise a non-complementary tail region, though such a tail is not required. In some embodiments, the reverse primer is a "universal reverse primer," which indicates that the sequence of the reverse primer can be used in a plurality of different reactions querying different target polynucleotides, but that the reverse primer nonetheless is the same sequence.

The term "upstream" as used herein takes on its customary meaning in molecular biology, and refers to the location of a region of a polynucleotide that is on the 5' side of a "downstream" region. Correspondingly, the term "downstream" refers to the location of a region of a polynucleotide that is on the 3' side of an "upstream" region.

As used herein, the term "hybridization" refers to the complementary base-pairing interaction of one nucleic acid with another nucleic acid that results in formation of a duplex, triplex, or other higher-ordered structure, and is used herein interchangeably with "annealing." Typically, the primary interaction is base specific, e.g., A/T and G/C, by Watson/Crick and Hoogsteen-type hydrogen bonding. Base-stacking and hydrophobic interactions can also contribute to duplex stability. Conditions for hybridizing detector probes and primers to complementary and substantially complementary target sequences are well known, e.g., as described in Nucleic Acid Hybridization, A Practical Approach, B. Hames and S. Higgins, eds., IRL Press, Washington, D.C. (1985) and J. Wetmur and N. Davidson, Mol. Biol. 31:349 et seq. (1968). In general, whether such annealing takes place is influenced by, among other things, the length of the polynucleotides and the complementary, the pH, the temperature, the presence of mono- and divalent cations, the proportion of G and C nucleotides in the hybridizing region, the viscosity of the medium, and the presence of denaturants. Such variables influence the time required for hybridization. Thus, the preferred annealing conditions will depend upon the particular application. Such conditions, however, can be routinely determined by the person of ordinary skill in the art without undue experimentation. It will be appreciated that complementarity need not be perfect; there can be a small number of base pair mismatches that will minimally interfere with hybridization between the target sequence and the single stranded nucleic acids of the present teachings. However, if the number of base pair mismatches is so great that no hybridization can occur under minimally stringent conditions then the sequence is generally not a complementary target sequence. Thus, complementarity herein is meant that the probes or primers are sufficiently complementary to the target sequence to hybridize under the selected reaction conditions to achieve the ends of the present teachings.

As used herein, the term "amplifying" refers to any means by which at least a part of a target polynucleotide, target polynucleotide surrogate, or combinations thereof, is reproduced, typically in a template-dependent manner, including without limitation, a broad range of techniques for amplifying nucleic acid sequences, either linearly or exponentially. Exemplary means for performing an amplifying step include ligase chain reaction (LCR), ligase detection reaction (LDR), ligation followed by Q-replicase amplification, PCR, primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA) and the like, including multiplex versions or combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), and the like. Descriptions of such techniques can be found in, among other places, Sambrook et al. Molecular Cloning, $3^{rd}$ Edition; Ausbel et al.; PCR Primer: A Laboratory Manual, Diffenbach, Ed., Cold Spring Harbor Press (1995); The Electronic Protocol Book, Chang Bioscience (2002), Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); Belgrader, Barany, and Lubin, Development of a Multiplex Ligation Detection Reaction DNA Typing Assay, Sixth International Symposium on Human Identification, 1995 (available on the world wide web at: promega.com/geneticidproc/ussymp6proc/blegrad.html); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18(2002); Lage et al., Genome Res. 2003 February; 13(2):294-307, and Landegren et al., Science 241:1077-80 (1988), Demidov, V., Expert Rev Mol Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, Published P.C.T. Application WO0056927A3, and Published P.C.T. Application WO9803673A1. In some embodiments, newly-formed nucleic acid duplexes are not initially denatured, but are used in their double-stranded form in one or more subsequent steps. An extension reaction is an amplifying technique that comprises elongating a linker probe that is annealed to a template in the 5' to 3' direction using an amplifying means such as a polymerase and/or reverse transcriptase. According to some embodiments, with appropriate buffers, salts, pH, temperature, and nucleotide triphosphates, including analogs thereof, i.e., under appropriate conditions, a polymerase incorporates nucleotides complementary to the template strand starting at the 3'-end of an annealed linker probe, to generate a complementary strand. In some embodiments, the polymerase used for extension lacks or substantially lacks 5' exonuclease activity. In some embodiments of the present teachings, unconventional nucleotide bases can be introduced into the amplification reaction products and the products treated by enzymatic (e.g., glycosylases) and/or physical-chemical means in order to render the product incapable of acting as a template for subsequent amplifications. In some embodiments, uracil can be included as a nucleobase in the reaction mixture, thereby allowing for subsequent reactions to decontaminate carry-over of previous uracil-containing products by the use of uracil-N-glycosylase (see for example Published P.C.T. Application WO9201814A2). In some embodiments of the present teachings, any of a variety of techniques can be employed prior to amplification in order to facilitate amplification success, as described for example in Radstrom et al., Mol Biotechnol. 2004 February; 26(2):133-46. In some embodiments, amplification can be achieved in a self-contained integrated approach comprising sample preparation and detection, as described for example in U.S. Pat. Nos. 6,153,425 and 6,649,378. Reversibly modified enzymes, for example but not limited to those described in U.S. Pat. No. 5,773,258, are also within the scope of the disclosed teachings. The present teachings also contemplate various uracil-based decontamination strategies, wherein for example uracil can be incorporated into an amplification reaction, and subsequent carry-over products removed with various glycosylase treatments (see for example U.S. Pat. No. 5,536, 649, and U.S. Provisional Application 60/584,682 to Andersen et al.,). Those in the art will understand that any protein with the desired enzymatic activity can be used in the disclosed methods and kits. Descriptions of DNA polymerases, including reverse transcriptases, uracil N-glycosylase, and the like, can be found in, among other places, Twyman, Advanced Molecular Biology, BIOS Scientific Publishers, 1999; Enzyme Resource Guide, rev. 092298, Promega, 1998; Sambrook and Russell; Sambrook et al.; Lehninger; PCR: The Basics; and Ausbel et al.

As used herein, the term "detector probe" refers to a molecule used in an amplification reaction, typically for quantitative or real-time PCR analysis, as well as end-point analysis. Such detector probes can be used to monitor the amplification of the target polynucleotide. In some embodiments, detector probes present in an amplification reaction are suitable for monitoring the amount of amplicon(s) produced as a function of time. Such detector probes include, but are not limited to, the 5'-exonuclease assay (TaqMan®) probes described herein (see also U.S. Pat. No. 5,538,848) various stem-loop molecular beacons (see e.g., U.S. Pat. Nos. 6,103,476 and 5,925,517 and Tyagi and Kramer, 1996, Nature Biotechnology 14:303-308), stemless or linear beacons (see, e.g., WO 99/21881), PNA Molecular Beacons™ (see, e.g., U.S. Pat. Nos. 6,355,421 and 6,593,091), linear PNA beacons (see, e.g., Kubista et al., 2001, SPIE 4264: 53-58), non-FRET probes (see, e.g., U.S. Pat. No. 6,150, 097), Sunrise®/Amplifluor® probes (U.S. Pat. No. 6,548, 250), stem-loop and duplex Scorpion™ probes (Solinas et al., 2001, Nucleic Acids Research 29:E96 and U.S. Pat. No. 6,589,743), bulge loop probes (U.S. Pat. No. 6,590,091), pseudo knot probes (U.S. Pat. No. 6,589,250), cyclicons (U.S. Pat. No. 6,383,752), MGB Eclipse™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001, Methods 25:463-471; Whitcombe et al., 1999, Nature Biotechnology. 17:804-807; Isacsson et al., 2000, Molecular Cell Probes. 14:321-328; Svanvik et al., 2000, Anal Biochem. 281:26-35; Wolffs et al., 2001, Biotechniques 766:769-771; Tsourkas et al., 2002, Nucleic Acids Research. 30:4208-4215; Riccelli et al., 2002, Nucleic Acids Research 30:4088-4093; Zhang et al., 2002 Shanghai. 34:329-332; Maxwell et al., 2002, J. Am. Chem. Soc. 124:9606-9612; Broude et al., 2002, Trends Biotechnol. 20:249-56; Huang et al., 2002, Chem Res. Toxicol. 15:118-126; and Yu et al., 2001, J. Am. Chem. Soc 14:11155-11161. Detector probes can also comprise quenchers, including without limitation black hole quenchers (Biosearch), Iowa Black (IDT), QSY quencher (Molecular Probes), and Dabsyl and Dabcel sulfonate/carboxylate Quenchers (Epoch).

Detector probes can also comprise two probes, wherein for example a fluor is on one probe, and a quencher is on the other probe, wherein hybridization of the two probes together on a target quenches the signal, or wherein hybridization on the target alters the signal signature via a change in fluorescence. Detector probes can also comprise sulfonate derivatives of fluorescenin dyes with SO3 instead of the carboxylate group, phosphoramidite forms of fluorescein, phosphoramidite forms of CY 5 (commercially available for example from Amersham). In some embodiments, interchelating labels are used such as ethidium bromide, SYBR® Green I (Molecular Probes), and PicoGreen® (Molecular Probes), thereby allowing visualization in real-time, or end point, of an amplification product in the absence of a detector probe. In some embodiments, real-time visualization can comprise both an intercalating detector probe and a sequence-based detector probe can be employed. In some embodiments, the detector probe is at least partially quenched when not hybridized to a complementary sequence in the amplification reaction, and is at least partially unquenched when hybridized to a complementary sequence in the amplification reaction. In some embodiments, the detector probes of the present teachings have a Tm of 63-69 C, though it will be appreciated that guided by the present teachings routine experimentation can result in detector probes with other Tms. In some embodiments, probes can further comprise various modifications such as a minor groove binder (see for example U.S. Pat. No. 6,486,308) to further provide desirable thermodynamic characteristics. In some embodiments, detector probes can correspond to identifying portions or identifying portion complements.

The term "corresponding" as used herein refers to a specific relationship between the elements to which the term refers. Some non-limiting examples of corresponding include: a linker probe can correspond with a target polynucleotide, and vice versa. A forward primer can correspond with a target polynucleotide, and vice versa. A linker probe can correspond with a forward primer for a given target polynucleotide, and vice versa. The 3' target-specific portion of the linker probe can correspond with the 3' region of a target polynucleotide, and vice versa. A detector probe can correspond with a particular region of a target polynucleotide and vice versa. A detector probe can correspond with a particular identifying portion and vice versa. In some cases, the corresponding elements can be complementary. In some cases, the corresponding elements are not complementary to each other, but one element can be complementary to the complement of another element.

The term "or combinations thereof" as used herein refers to all permutations and combinations of the listed items preceding the term. For example, "A, B, C, or combinations thereof" is intended to include at least one of: A, B, C, Aft AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

As used herein, the term "reaction vessel" generally refers to any container in which a reaction can occur in accordance with the present teachings. In some embodiments, a reaction vessel can be an eppendorf tube, and other containers of the sort in common practice in modern molecular biology laboratories. In some embodiments, a reaction vessel can be a well in microtitre plate, a spot on a glass slide, or a well in an Applied Biosystems TaqMan Low Density Array for gene expression (formerly MicroCard™). For example, a plurality of reaction vessels can reside on the same support. In some embodiments, lab-on-a-chip like devices, available for example from Caliper and Fluidgm, can provide for reaction vessels. In some embodiments, various microfluidic approaches as described in U.S. Provisional Application 60/545,674 to Wenz et al., can be employed. It will be recognized that a variety of reaction vessel are available in the art and within the scope of the present teachings.

As used herein, the term "detection" refers to any of a variety of ways of determining the presence and/or quantity and/or identity of a target polynucleotide. In some embodiments employing a donor moiety and signal moiety, one may use certain energy-transfer fluorescent dyes. Certain non-limiting exemplary pairs of donors (donor moieties) and acceptors (signal moieties) are illustrated, e.g., in U.S. Pat. Nos. 5,863,727; 5,800,996; and 5,945,526. Use of some combinations of a donor and an acceptor have been called FRET (Fluorescent Resonance Energy Transfer). In some embodiments, fluorophores that can be used as signaling probes include, but are not limited to, rhodamine, cyanine 3 (Cy 3), cyanine 5 (Cy 5), fluorescein, Vic™ Liz™, Tamra™, 5-Fam™, 6-Fam™, and Texas Red (Molecular Probes). (Vic™ Liz™, Tamra™, 5-Fam™, and 6-Fam™ (all available from Applied Biosystems, Foster City, Calif.). In some embodiments, the amount of detector probe that gives a fluorescent signal in response to an excited light typically relates to the amount of nucleic acid produced in the amplification reaction. Thus, in some embodiments, the amount of fluorescent signal is related to the amount of product created in the amplification reaction. In such embodiments, one can therefore measure the amount of amplification product by measuring the intensity of the fluorescent signal from the fluorescent indicator. According to some embodiments, one can employ an internal standard to quantify the amplification product indicated by the fluorescent signal. See, e.g., U.S. Pat. No. 5,736,333. Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670, and include, but are not limited to the ABI Prism® 7700 Sequence Detection System (Applied Biosystems, Foster City, Calif.), the ABI GeneAmp® 5700 Sequence Detection System (Applied Biosystems, Foster City, Calif.), the ABI GeneAmp® 7300 Sequence Detection System (Applied Biosystems, Foster City, Calif.), and the ABI GeneAmp® 7500 Sequence Detection System (Applied Biosystems). In some embodiments, each of these functions can be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product. In some embodiments, combined thermal cycling and fluorescence detecting devices can be used for precise quantification of target nucleic acid sequences in samples. In some embodiments, fluorescent signals can be detected and displayed during and/or after one or more thermal cycles, thus permitting monitoring of amplification products as the reactions occur in "real time." In some embodiments, one can use the amount of amplification product and number of amplification cycles to calculate how much of the target nucleic acid sequence was in the sample prior to amplification. In some embodiments, one could simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target polynucleotide. As used herein, determining the presence of a target can comprise identifying it, as well as optionally quantifying it. In some embodiments, the amplification products can be scored as positive or negative as soon as a given number of cycles is complete. In some embodiments, the results may be transmitted electronically directly to a database and tabulated. Thus, in some embodiments, large numbers of samples can be processed and analyzed with less time and labor when such an instrument is used. In some embodiments, different detector probes may distinguish between different target polynucleotides. A non-limiting example of such a probe is a 5'-nuclease fluorescent probe, such as a TaqMan® probe molecule, wherein a fluorescent molecule is attached to a fluorescence-quenching molecule through an oligonucleotide link element. In some embodiments, the oligonucleotide link element of the 5'-nuclease fluorescent probe binds to a specific sequence of an identifying portion or its complement. In some embodiments, different 5'-nuclease fluorescent probes, each fluorescing at different wavelengths, can distinguish between different amplification products within the same amplification reaction. For example, in some embodiments, one could use two different 5'-nuclease fluorescent probes that fluoresce at two different wavelengths ($WL_A$ and $WL_B$) and that are specific to two different stem regions of two different extension reaction products (A' and B', respectively). Amplification product A' is formed if target nucleic acid sequence A is in the sample, and amplification product B' is formed if target nucleic acid sequence B is in the sample. In some embodiments, amplification product A' and/or B' may form even if the appropriate target nucleic acid sequence is not in the sample, but such occurs to a measurably lesser extent than when the appropriate target nucleic acid sequence is in the sample. After amplification, one can determine which specific target nucleic acid sequences are present in the sample based on the wavelength of signal detected and their intensity. Thus, if an appropriate detectable signal value of only wavelength $WL_A$ is detected, one would know that the sample includes target nucleic acid sequence A, but not target nucleic acid sequence B. If an appropriate detectable signal value of both wavelengths $WL_A$ and $WL_B$ are detected, one would know that the sample includes both target nucleic acid sequence A and target nucleic acid sequence B. In some embodiments, detection can occur through any of a variety of mobility dependent analytical techniques based on differential rates of migration between different analyte species. Exemplary mobility-dependent analysis techniques include electrophoresis, chromatography, mass spectroscopy, sedimentation, e.g., gradient centrifugation, field-flow fractionation, multi-stage extraction techniques, and the like. In some embodiments, mobility probes can be hybridized to amplification products, and the identity of the target polynucleotide determined via a mobility dependent analysis technique of the eluted mobility probes, as described for example in Published P.C.T. Application WO04/46344 to Rosenblum et al., and WO01/92579 to Wenz et al., In some embodiments, detection can be achieved by various microarrays and related software such as the Applied Biosystems Array System with the Applied Biosystems 1700 Chemiluminescent Microarray Analyzer and other commercially available array systems available from Affymetrix, Agilent, Illumina, and Amersham Biosciences, among others (see also Gerry et al., J. Mol. Biol. 292:251-62, 1999; De Bellis et al., Minerva Biotec 14:247-52, 2002; and Stears et al., Nat. Med. 9:140-45, including supplements, 2003). It will also be appreciated that detection can comprise reporter groups that are incorporated into the reaction products, either as part of labeled primers or due to the incorporation of labeled dNTPs during an amplification, or attached to reaction products, for example but not limited to, via hybridization tag complements comprising reporter groups or via linker arms that are integral or attached to reaction products. Detection of unlabeled reaction products, for example using mass spectrometry, is also within the scope of the current teachings.

EXEMPLARY EMBODIMENTS

FIGS. 1A-1C depict certain compositions according to some embodiments of the present teachings. FIG. 1A, a miRNA molecule (1, dashed line) is depicted. FIG. 1B, a linker probe (2) is depicted, illustrating a 3' target specific portion (3), a stem (4), and a loop (5). FIG. 1C, a miRNA hybridized to a linker probe is depicted, illustrating the 3' target specific portion of the linker probe (3) hybridized to the 3' end region of the miRNA (6).

Figure 2A:
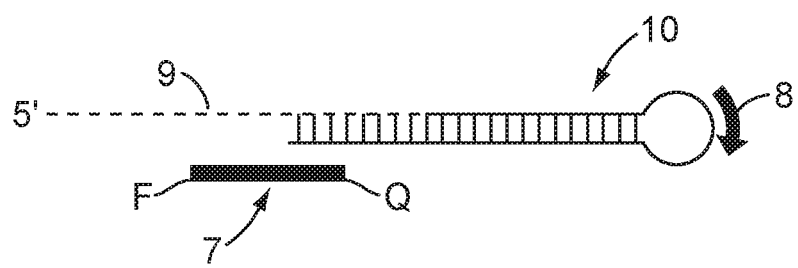
FIGS. 2A, 2B, 2C, and 2D depict certain aspects of various compositions according to some embodiments of the present teachings.
Figure 2B:
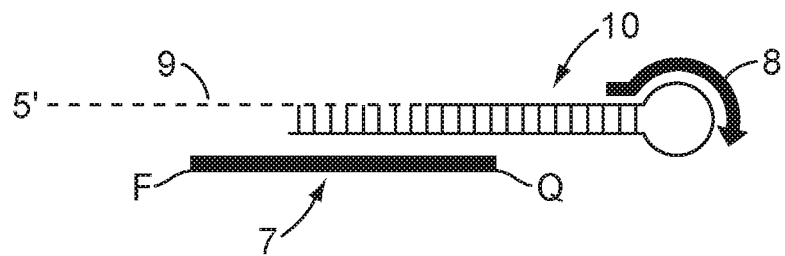
Figure 2C:
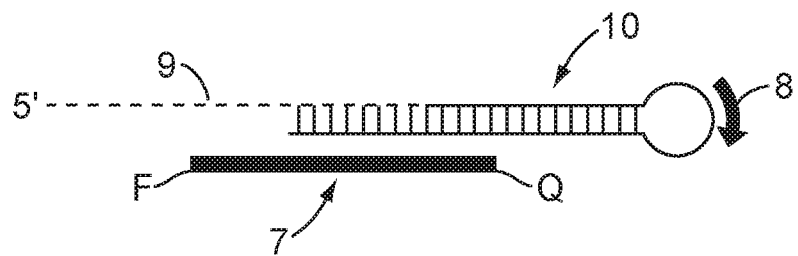
Figure 2D:
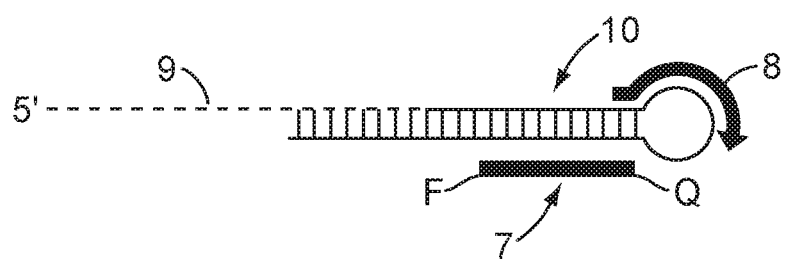

As shown in FIGS. 2A-2D, a target polynucleotide (9, dotted line) is illustrated to show the relationship with various components of the linker probe (10), the detector probe (7), and the reverse primer (8), according to various non-limiting embodiments of the present teachings. For example as shown in FIG. 2A, in some embodiments the detector probe (7) can correspond with the 3' end region of the target polynucleotide in the amplification product as well as a region upstream from the 3' end region of the target polynucleotide in the amplification product. (Here, the detector probe is depicted as rectangle (7) with an F and a Q, symbolizing a TaqMan probe with a fluorophore (F) and a quencher (Q)). Also shown in FIG. 2A, the loop can correspond to the reverse primer (8). In some embodiments as shown in FIG. 2B, the detector probe (7) can correspond with a region of the amplification product corresponding with the 3' end region of the target polynucleotide in the amplification product, as well as a region upstream from the 3' end region of the target polynucleotide in the amplification product, as well as the linker probe stem in the amplification product. Also shown in FIG. 2B, the upstream region of the stem, as well as the loop, can correspond to the reverse primer (8). In some embodiments as shown in FIG. 2C, the detector probe can correspond to the amplification product in a manner similar to that shown in FIG. 2B, but the loop can correspond to the reverse primer (8). In some embodiments as shown in FIG. 2D, the detector probe (7) can correspond with the linker probe stem in the amplification product. Also shown in FIG. 2D, the upstream region of the stem, as well as the loop can correspond to the reverse primer (8). It will be appreciated that various related strategies for implementing the different functional regions of these compositions are possible in light of the present teachings, and that such derivations are routine to one having ordinary skill in the art without undue experimentation.

Figure 3:
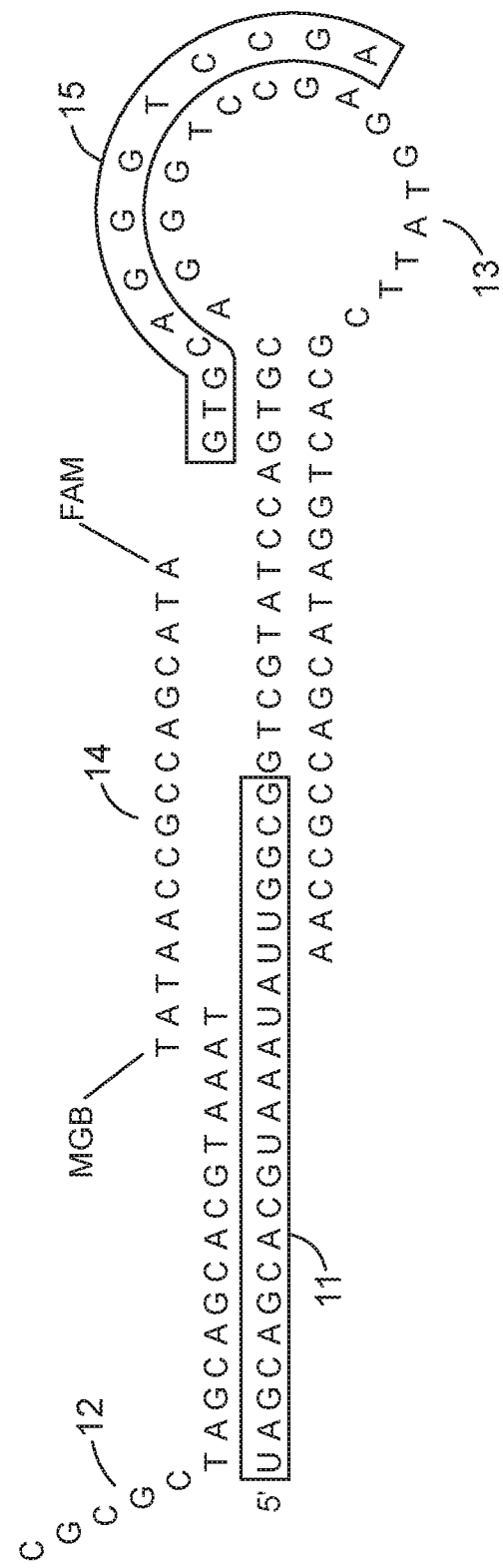
FIG. 3 depicts certain sequences of various compositions according to some embodiments of the present teachings.

FIG. 3 depicts the nucleotide relationship for the micro RNA MiR-16 (boxed, 11) according to some embodiments of the present teachings. Shown here is the interrelationship of MiR-16 to a forward primer (12) (SEQ ID No. 781), a linker probe (13), a TaqMan detector probe (14) (SEQ ID No. 782), and a reverse primer (boxed, 15) (SEQ ID No. 783). The TaqMan probe comprises a 3' minor groove binder (MGB), and a 5' FAM fluorophore. It will be appreciated that in some embodiments of the present teachings the detector probes, such as for example TaqMan probes, can hybridize to either strand of an amplification product. For example, in some embodiments the detector probe can hybridize to the strand of the amplification product corresponding to the first strand synthesized. In some embodiments, the detector probe can hybridize to the strand of the amplification product corresponding to the second strand synthesized.

Figure 4:
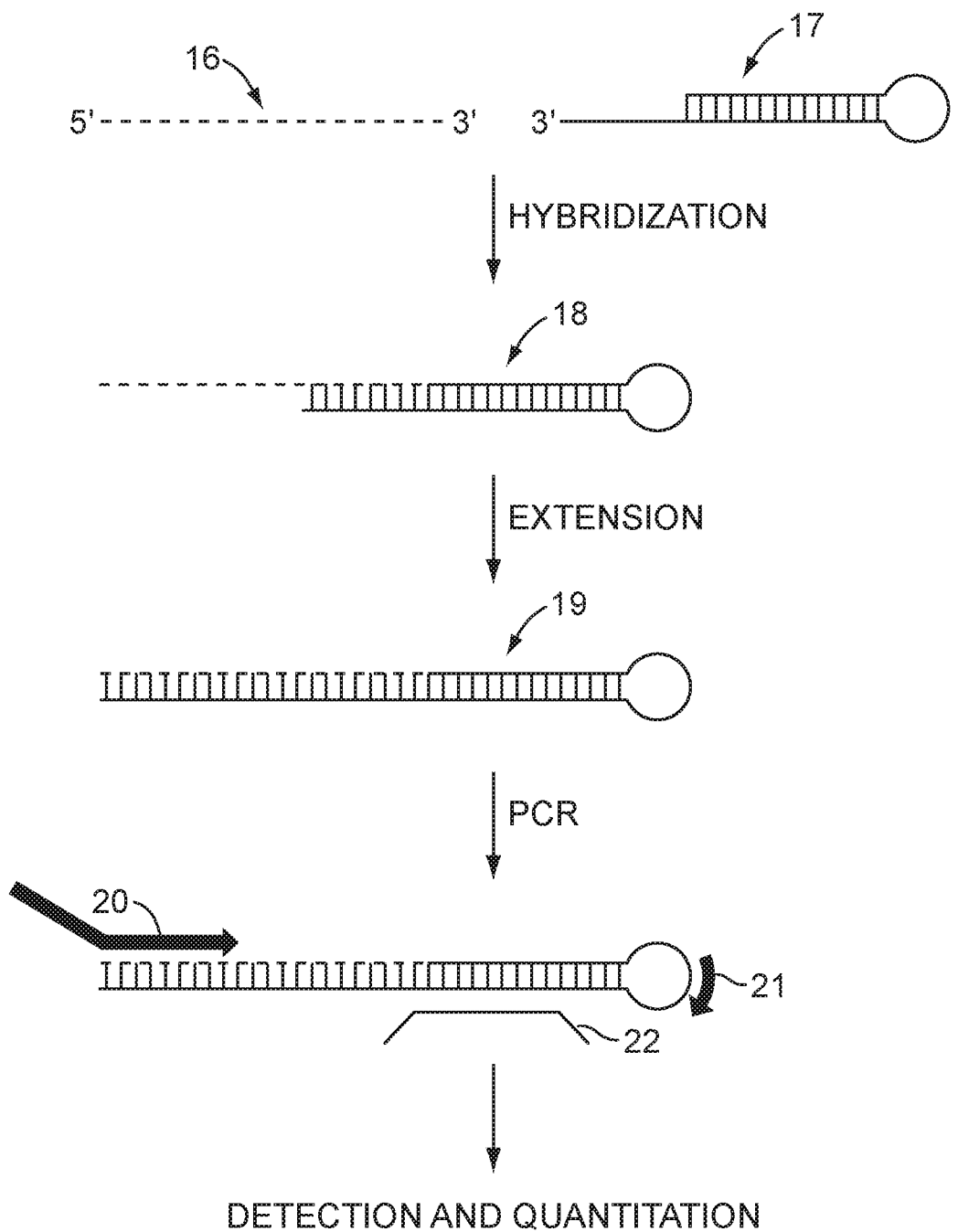
FIG. 4 depicts one single-plex assay design according to some embodiments of the present teachings.

FIG. 4 depicts a single-plex assay design according to some embodiments of the present teachings. Here, a miRNA molecule (16) and a linker probe (17) are hybridized together (18). The 3' end of the linker probe of the target-linker probe composition is extended to form an extension product (19) that can be amplified in a PCR. The PCR can comprise a miRNA specific forward primer (20) and a reverse primer (21). The detection of a detector probe (22) during the amplification allows for quantitation of the miRNA.

Figure 5:
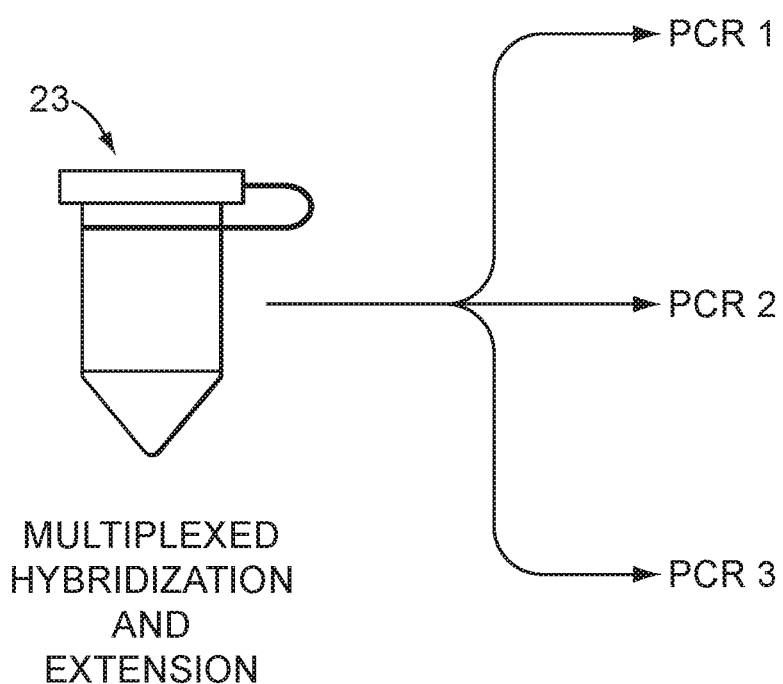
FIG. 5 depicts an overview of a multiplex assay design according to some embodiments of the present teachings.

FIG. 5 depicts an overview of a multiplex assay design according to some embodiments of the present teachings. Here, a multiplexed hybridization and extension reaction is performed in a first reaction vessel (23). Thereafter, aliquots of the extension reaction products from the first reaction vessel are transferred into a plurality of amplification reactions (here, depicted as PCRs 1, 2, and 3) in a plurality of second reaction vessels. Each PCR can comprise a distinct primer pair and a distinct detector probe. In some embodiments, a distinct primer pair but the same detector probe can be present in each of a plurality of PCRs.

Figure 6:
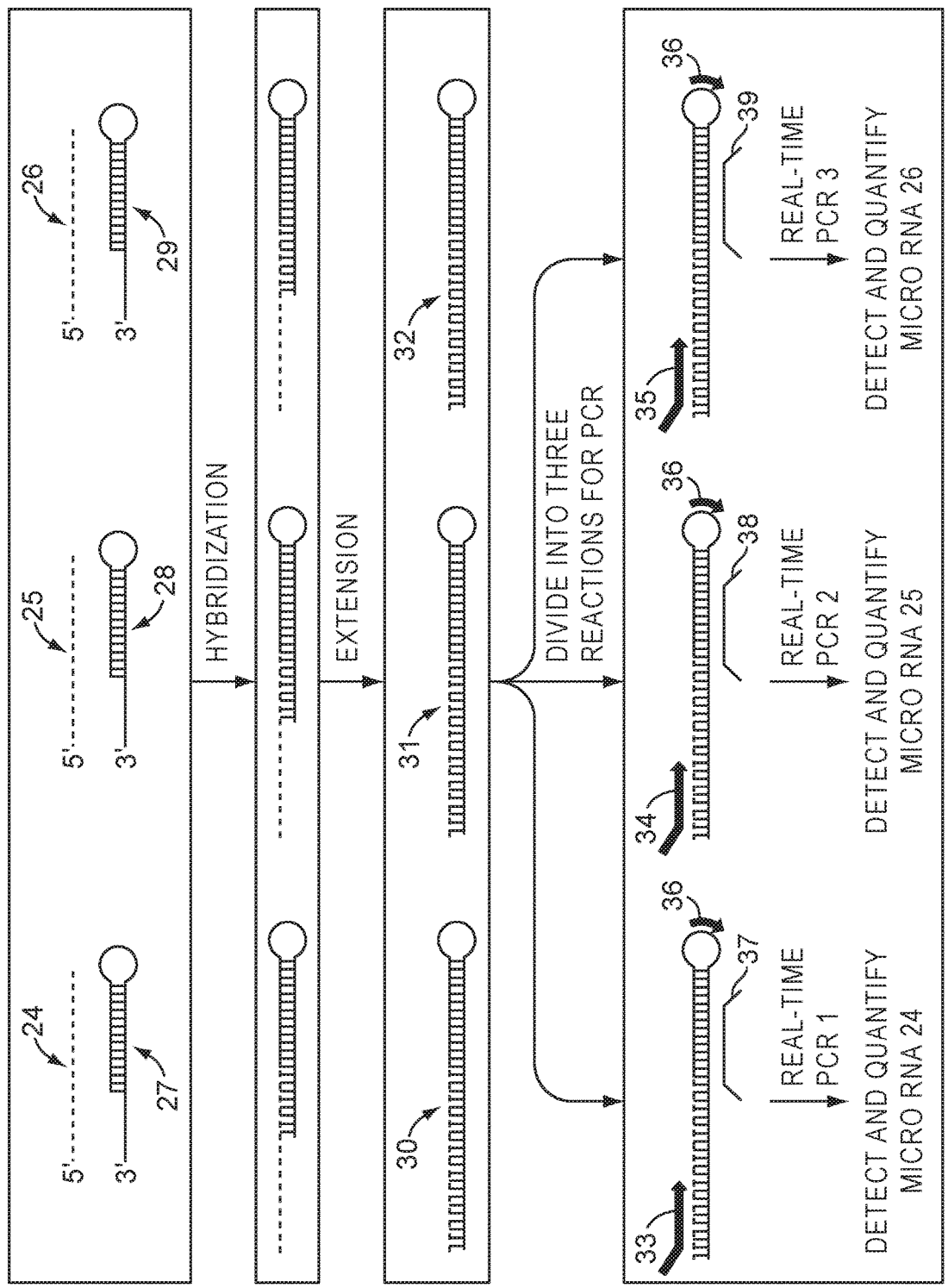
FIG. 6 depicts a multiplex assay design according to some embodiments of the present teachings.

FIG. 6 depicts a multiplex assay design according to some embodiments of the present teachings. Here, three different miRNAs (24, 25, and 26) are queried in a hybridization reaction comprising three different linker probes (27, 28, and 29). Following hybridization and extension to form extension products (30, 31, and 32), the extension products are divided into three separate amplification reactions. (Though not explicitly shown, it will be appreciated that a number of copies of the molecules depicted by 30, 31, and 32 can be present, such that each of the three amplification reactions can have copies of 30, 31, and 32.) PCR 1 comprises a forward primer specific for miRNA 24 (33), PCR 2 comprises a forward primer specific for miRNA 25 (34), and PCR 3 comprises a forward primer specific for miRNA 26 (35). Each of the forward primers further comprise a non-complementary tail portion. PCR 1, PCR 2, and PCR 3 all comprise the same universal reverse primer 36. Further, PCR 1 comprises a distinct detector probe (37) that corresponds to the 3' end region of miRNA 24 and the stem of linker probe 27, PCR 2 comprises a distinct detector probe (38) that corresponds to the 3' end region of miRNA 25 and the stem of linker probe 28, and PCR 3 comprises a distinct detector probe (39) that corresponds to the 3' region of miRNA 26 and the stem of linker probe 29.

The present teachings also contemplate reactions comprising configurations other than a linker probe. For example, in some embodiments, two hybridized molecules with a sticky end can be employed, wherein for example an overlapping 3' sticky end hybridizes with the 3' end region of the target polynucleotide. Some descriptions of two molecule configurations that can be employed in the present teachings can be found in Chen et al., U.S. Provisional Application 60/517,470. Viewed in light of the present teachings herein, one of skill in the art will appreciate that the approaches of Chen et al., can also be employed to result in extension reaction products that are longer that the target polynucleotide. These longer products can be detected with detector probes by, for example, taking advantage of the additional nucleotides introduced into the reaction products.

The present teachings also contemplate embodiments wherein the linker probe is ligated to the target polynucleotide, as described for example in Chen et al., U.S. Provisional Application 60/575,661, and the corresponding co-filed U.S. Provisional application co-filed herewith Further, it will be appreciated that in some embodiments of the present teachings, the two molecule configurations in Chen et al., U.S. Provisional Application 60/517,470 can be applied in embodiments comprising the linker approaches discussed in Chen et al., U.S. Provisional Application 60/575,661.

Generally however, the loop structure of the present teachings will enhance the Tm of the target polynucleotide-linker probe duplex. Without being limited to any particular theory, this enhanced Tm could possibly be due to base stacking effects. Also, the characteristics of the looped linker probe of the present teachings can minimize nonspecific priming during the extension reaction, and/or a subsequent amplification reaction such as PCR. Further, the looped linker probe of the present teachings can better differentiate mature and precursor forms of miRNA, as illustrated infra in Example 6.

The present teachings also contemplate encoding and decoding reaction schemes, wherein a first encoding extension reaction is followed by a second decoding amplification reaction, as described for example in Livak et al., U.S. Provisional Application 60/556,162, Chen et al., U.S. Provisional Application 60/556,157, Andersen et al., U.S. Provisional Application 60/556,224, and Lao et al., U.S. Provisional Application 60/556,163.

The present teachings also contemplate a variety of strategies to minimize the number of different molecules in multiplexed amplification strategies, as described for example in Whitcombe et al., U.S. Pat. No. 6,270,967.

In certain embodiments, the present teachings also provide kits designed to expedite performing certain methods. In some embodiments, kits serve to expedite the performance of the methods of interest by assembling two or more components used in carrying out the methods. In some embodiments, kits may contain components in pre-measured unit amounts to minimize the need for measurements by end-users. In some embodiments, kits may include instructions for performing one or more methods of the present teachings. In certain embodiments, the kit components are optimized to operate in conjunction with one another.

For example, the present teachings provide a kit comprising, a reverse transcriptase and a linker probe, wherein the linker probe comprises a stem, a loop, and a 3' target-specific portion, wherein the 3' target-specific portion corresponds to a miRNA. In some embodiments, the kits can comprise a DNA polymerase. In some embodiments, the kits can comprise a primer pair. In some embodiments, the kits can further comprise a forward primer specific for a miRNA, and, a universal reverse primer, wherein the universal reverse primer comprises a nucleotide of the loop of the linker probe. In some embodiments, the kits can comprise a plurality of primer pairs, wherein each primer pair is in one reaction vessel of a plurality of reaction vessels. In some embodiments, the kits can comprise a detector probe. In some embodiments, the detector probe comprises a nucleotide of the linker probe stem in the amplification product or a nucleotide of the linker probe stem complement in the amplification product, and the detector probe further comprises a nucleotide of the 3' end region of the miRNA in the amplification product or a nucleotide of the 3' end region of the miRNA complement in the amplification product.

The present teachings further contemplate kits comprising a means for hybridizing, a means for extending, a means for amplifying, a means for detecting, or combinations thereof.

While the present teachings have been described in terms of these exemplary embodiments, the skilled artisan will readily understand that numerous variations and modifications of these exemplary embodiments are possible without undue experimentation. All such variations and modifications are within the scope of the current teachings. Aspects of the present teachings may be further understood in light of the following examples, which should not be construed as limiting the scope of the teachings in any way.

Example 1

A single-plex reaction was performed in replicate for a collection of mouse miRNAs, and the effect of the presence or absence of ligase, as well as the presence or absence of reverse transcriptase, determined. The results are shown in Table 1 as Ct values.

First, a 6 ul reaction was set up comprising: 1 ul Reverse Transcription Enzyme Mix (Applied Biosystems part number 4340444) (or 1 ul dH2O), 0.5 ul T4 DNA Ligase (400 units/ul, NEB) (or 0.5 ul dH20), 0.25 ul 2M KCl, 0.05 ul dNTPs (25 mM each), 0.25 ul T4 Kinase (10 units/ul, NEB), 1 ul 10×T4 DNA ligase buffer (NEB), 0.25 ul Applied Biosystems RNase Inhibitor (10 units/up, and 2.2 ul dH20 Next, 2 ul of the linker probe (0.25 uM) and RNA samples (2 ul of 0.25 ug/ul mouse lung total RNA (Ambion, product number 7818) were added. Next, the reaction was mixed, spun briefly, and placed on ice for 5 minutes.

The reaction was then incubated at 16 C for 30 minutes, 42 C for 30 minutes, followed by 85 C for 5 minutes, and then held at 4 C. The reactions were diluted 4 times by adding 30 ul of dH20 prior to the PCR amplification.

A 10 ul PCR amplification was then set up comprising: 2 ul of diluted reverse transcription reaction product, 1.3 ul 10 uM miRNA specific Forward Primer, 0.7 ul 10 uM Universal Reverse Primer, 0.2 ul TaqMan detector probe, 0.2 ul dNTPs (25 mM each), 0.6 ul dH20, 5 ul 2×TaqMan master mix (Applied Biosystems, without UNG). The reaction was started with a 95 C step for 10 minutes. Then, 40 cycles were performed, each cycle comprising 95 C for 15 seconds, and 60 C for 1 minute. Table 1 indicates the results of this experiment.

TABLE 1

| Replicate | Ligase | Reverse transcriptase | Let-7a1 | mir16 | mir20 | mir21 | mir26a | mir30a | mir224 | miRNA average |
|---|---|---|---|---|---|---|---|---|---|---|
| I | Yes | Yes | 16.8 | 16.0 | 19.1 | 16.8 | 15.0 | 21.3 | 27.3 | 18.9 |
|  | Yes | No | 38.7 | 31.3 | 39.9 | 31.9 | 30.1 | 33.3 | 40.0 | 35.0 |
|  | No | Yes | 18.0 | 14.6 | 18.3 | 16.2 | 14.0 | 21.3 | 26.4 | 18.4 |
|  | No | No | 40.0 | 36.6 | 40.0 | 40.0 | 33.8 | 39.2 | 40.0 | 38.5 |
| II | Yes | Yes | 17.1 | 16.2 | 19.3 | 17.0 | 15.1 | 21.4 | 27.3 | 19.1 |
|  | Yes | No | 38.9 | 31.2 | 37.6 | 32.1 | 30.4 | 33.4 | 39.4 | 34.7 |
|  | No | Yes | 18.4 | 14.8 | 18.7 | 16.6 | 14.3 | 21.5 | 26.7 | 18.7 |
|  | No | No | 40.0 | 36.1 | 40.0 | 40.0 | 34.1 | 40.0 | 40.0 | 38.6 |
| Replicate Average | Yes | Yes | 16.9 | 16.1 | 19.2 | 16.9 | 15.0 | 21.4 | 27.3 | 19.0 |
|  | Yes | No | 38.8 | 31.2 | 38.8 | 32.0 | 30.3 | 33.4 | 39.7 | 34.9 |
|  | No | Yes | 18.2 | 14.7 | 18.5 | 16.4 | 14.1 | 21.4 | 26.6 | 18.6 |
|  | No | No | 40.0 | 36.4 | 40.0 | 40.0 | 34.0 | 39.6 | 40.0 | 40.0 |

Sequences of corresponding forward primers, reverse primer, and TaqMan probes are shown in Table 2.

TABLE 2

| miRNA ID | SEQ ID NO: | miRNA sequences |
|---|---|---|
| miR-16 | 1 | uagcagcacguaaauauuggcg |
| miR-20 | 2 | uaaagugcuuauagugcaggua |
| miR-21 | 3 | uagcuuaucagacugauguuga |
| miR-22 | 4 | aagcugccaguugaagaacugu |
| miR-26a | 5 | uucaaguaauccaggauaggcu |
| miR-29 | 6 | cuagcaccaucugaaaucgguu |
| miR-30a | 7 | cuuucagucggauguuugcagc |
| miR-34 | 8 | uggcagugucuuuagcugguugu |
| miR-200b | 9 | cucuaauacugccugguaaugaug |
| miR-323 | 10 | gcacauuacacggucgaccucu |
| miR-324-5 | 11 | cgcaucccuagggcauuggugu |
| Let-7a1 | 12 | ugagguaguagguuguauaguu |

| Linker probe | SEQ ID NO: | Linker probe sequences |
|---|---|---|
| miR-16linR6 | 13 | GTCGTATCCAGTGCAGGGTCCGAGGGTATTCGCACTGGATACGACCGCCAA |
| miR20LinR6 | 14 | GTCGTATCCAGTGCAGGGTCCGAGGGTATTCGCACTGGATACGACTACCTG |
| miR-21linR6 | 15 | GTCGTATCCAGTGCAGGGTCCGAGGGTATTCGCACTGGATACGACTCAACA |
| miR-22linR6 | 16 | GTCGTATCCAGTGCAGGGTCCGAGGGTATTCGCACTGGATACGACACAGTT |
| miR-26a1inR6 | 17 | GTCGTATCCAGTGCAGGGTCCGAGGGTATTCGCACTGGATACGACAGCCTA |

TABLE 2-continued

| | SEQ ID NO: | |
|---|---|---|
| miR-29linR6 | 18 | GTCGTATCCAGTGCAGGGTCCGAGGGTATTCGCACTGGATACGACAACCGA |
| miR30LinR6 | 19 | GTCGTATCCAGTGCAGGGTCCGAGGGTATTCGCACTGGATACGACGCTGCA |
| miR-34linR6 | 20 | GTCGTATCCAGTGCAGGGTCCGAGGGTATTCGCACTGGATACGACACAACC |
| miR-200blinR6 | 21 | GTCGTATCCAGTGCAGGGTCCGAGGGTATTCGCACTGGATACGACCATCAT |
| miR-323linR6 | 22 | GTCGTATCCAGTGCAGGGTCCGAGGGTATTCGCACTGGATACGACAGAGGT |
| miR-324-5linR6 | 23 | GTCGTATCCAGTGCAGGGTCCGAGGGTATTCGCACTGGATACGACACACCA |
| let7aLinR6 | 24 | GTCGTATCCAGTGCAGGGTCCGAGGGTATTCGCACTGGATACGACAACTAT |

| Forward primer ID | SEQ ID NO: | Forward primer sequences |
|---|---|---|
| miR-16F55 | 25 | CGCGCTAGCAGCACGTAAAT |
| miR-20F56 | 26 | GCCGCTAAAGTGCTTATAGTGC |
| miR-21F56 | 27 | GCCCGCTAGCTTATCAGACTGATG |
| miR-22F56 | 28 | GCCTGAAGCTGCCAGTTGA |
| miR-26aF54 | 29 | CCGGCGTTCAAGTAATCCAGGA |
| miR-29F56 | 30 | GCCGCTAGCACCATCTGAAA |
| miR-30aF58 | 31 | GCCCCTTTCAGTCGGATGTTT |
| miR-34F56 | 32 | GCCCGTGGCAGTGTCTTAG |
| miR-200bF56 | 33 | GCCCCTCTAATACTGCCTGG |
| miR-323F58 | 34 | GCCACGCACATTACACGGTC |
| miR-324-5F56 | 35 | GCCACCATCCCCTAGGGC |
| let-7a1F56 | 36 | GCCGCTGAGGTAGTAGGTTGT |

| TaqMan probe ID | SEQ ID NO: | TaqMan probe sequences |
|---|---|---|
| miR-16_Tq8F67 | 37 | (6FAM)ATACGACCGCCAATAT(MGB) |
| miR20_Tq8F68 | 38 | (6FAM)CTGGATACGACTACCTG(MGB) |
| miR-21_Tq8F68 | 39 | (6FAM)CTGGATACGACTCAACA(MGB) |
| miR-22_Tq8F68 | 40 | (6FAM)TGGATACGACACAGTTCT(MGB) |
| miR-26a_Tq8F69 | 41 | (6FAM)TGGATACGACAGCCTATC(MGB) |
| miR-29_Tq8F68 | 42 | (6FAM)TGGATACGACAACCGAT(MGB) |
| miR30_Tq8F68 | 43 | (6FAM)CTGGATACGACGCTGC(MGB) |
| miR-34_Tq8F68 | 44 | (6FAM)ATACGACACAACCAGC(MGB) |
| miR-200b_Tq8F67 | 45 | (6FAM)ATACGACCATCATTACC(MGB) |
| miR-323_Tq8F67 | 46 | (6FAM)CTGGATACGACAGAGGT(MGB) |
| miR-324-5Tq8F68 | 47 | (6FAM)ATACGACACACCAATGC(MGB) |
| let7a_Tq8F68 | 48 | (6FAM)TGGATACGACAACTATAC(MGB) |

| Universal reverse primer ID | SEQ ID NO: | Reverse primer sequence |
|---|---|---|
| miR-UP-R67.8 | 49 | GTGCAGGGTCCGAGGT |

Example 2

A multiplex (12-plex) assay was performed and the results compared to a corresponding collection of single-plex reactions. Additionally, the effect of the presence or absence of ligase, as well as the presence or absence of reverse transcriptase, was determined. The experiments were performed essentially the same as in Example 1, and the concentration of each linker in the 12-plex reaction was 0.05 uM, thereby resulting in a total linker probe concentration of 0.6 uM. Further, the diluted 12-plex reverse transcription product was split into 12 different PCR amplification reactions, wherein a miRNA forward primer and a universal reverse primer and a detector probe where in each amplification reaction. The miRNA sequences, Forward primers, and TaqMan detector probes are included in Table 2. The results are shown in Table 3.

TABLE 3

Singleplex vs. Multiplex Assay With Or Without T4 DNA Ligase

| | 1-plex Ct | | 12-plex Ct | | Ligation + RT | 1-vs. |
|---|---|---|---|---|---|---|
| miRNA | Ligation + RT | RT only | Ligation + RT | RT only | vs RT only | 12-plex |
| let-7a1 | 17.8 | 16.3 | 17.6 | 17.0 | 1.0 | −0.3 |
| mir-16 | 16.0 | 15.1 | 16.1 | 15.3 | 0.9 | −0.1 |
| mir-20 | 19.3 | 18.7 | 19.8 | 19.5 | 0.4 | −0.6 |
| mir-21 | 17.0 | 15.8 | 17.1 | 16.3 | 1.0 | −0.3 |
| mir-22 | 21.6 | 20.4 | 21.4 | 20.7 | 1.0 | −0.1 |
| mir-26a | 15.2 | 14.3 | 15.6 | 14.9 | 0.8 | −0.4 |
| mir-29 | 17.9 | 16.8 | 17.7 | 17.0 | 0.9 | 0.0 |
| mir-30a | 20.7 | 19.9 | 21.2 | 20.7 | 0.7 | −0.7 |
| mir-34 | 21.3 | 20.4 | 22.0 | 21.0 | 0.9 | −0.6 |
| mir-200b | 19.9 | 19.2 | 21.1 | 20.2 | 0.8 | −1.0 |
| mir-323 | 32.5 | 31.2 | 33.6 | 32.3 | 1.3 | −1.1 |

TABLE 3-continued

Singleplex vs. Multiplex Assay With Or Without T4 DNA Ligase

| miRNA | 1-plex Ct | | 12-plex Ct | | Ligation + RT vs RT only | 1-vs. 12-plex |
|---|---|---|---|---|---|---|
| | Ligation + RT | RT only | Ligation + RT | RT only | | |
| mir-324-5 | 24.7 | 23.1 | 25.0 | 24.4 | 1.1 | −0.8 |
| Average | 20.3 | 19.3 | 20.7 | 19.9 | 0.9 | −0.5 |

Example 3

An experiment was performed to determine the effect of buffer conditions on reaction performance. In one set of experiments, a commercially available reverse transcription buffer from Applied Biosystems (part number 43400550) was employed in the hybridization and extension reaction. In a corresponding set of experiments, a commercially available T4 DNA ligase buffer (NEB) was employed in the hybridization and extension reaction. The experiments were performed as single-plex format essentially as described for Example 1, and each miRNA was done in triplicate. The results are shown in Table 4, comparing RT buffer (AB part #4340550) vs T4 DNA ligase buffer.

TABLE 4

| | RT Buffer | | | | T4 DNA Ligase Buffer | | | | RT vs T4 Buffer |
|---|---|---|---|---|---|---|---|---|---|
| | I | II | III | Mean | I | II | III | Mean | |
| let-7a1 | 22.7 | 22.8 | 22.8 | 22.8 | 20.8 | 20.7 | 20.6 | 20.7 | 2.1 |
| mir-16 | 18.4 | 18.5 | 18.6 | 18.5 | 17.7 | 17.8 | 17.9 | 17.8 | 0.7 |
| mir-20 | 23.6 | 23.7 | 23.8 | 23.7 | 23.1 | 23.1 | 23.0 | 23.1 | 0.6 |
| mir-21 | 20.4 | 20.4 | 20.5 | 20.4 | 19.4 | 19.3 | 19.2 | 19.3 | 1.1 |
| mir-22 | 24.0 | 23.9 | 24.1 | 24.0 | 22.7 | 22.7 | 22.7 | 22.7 | 1.3 |
| mir-26a | 19.8 | 19.9 | 20.1 | 19.9 | 18.9 | 19.0 | 19.0 | 18.9 | 1.0 |
| mir-29 | 21.3 | 21.3 | 21.4 | 21.3 | 20.5 | 20.6 | 20.5 | 20.5 | 0.8 |
| mir-30a | 24.4 | 24.4 | 24.4 | 24.4 | 23.6 | 23.4 | 23.6 | 23.5 | 0.9 |
| mir-34 | 24.9 | 24.8 | 25.1 | 25.0 | 23.0 | 23.1 | 23.2 | 23.1 | 1.9 |
| mir-200b | 25.8 | 25.8 | 25.9 | 25.9 | 24.6 | 24.6 | 24.8 | 24.7 | 1.2 |
| mir-323 | 34.6 | 34.5 | 34.8 | 34.6 | 34.7 | 34.2 | 34.5 | 34.5 | 0.2 |
| mir-324-5 | 26.0 | 26.0 | 26.1 | 26.0 | 25.4 | 25.7 | 25.6 | 25.6 | 0.5 |
| Average | 23.8 | 23.8 | 24.0 | 23.9 | 22.9 | 22.8 | 22.9 | 22.9 | 1.0 |

Example 4

An experiment was performed to examine the effect of ligase and kinase in a real-time miRNA amplification reaction. Here, twelve single-plex reactions were performed in duplicate, essentially as described in Example 1. Results are shown in Table 5.

TABLE 5

| | Ligase & Kinase | | | No Ligase/No Kinase | | |
|---|---|---|---|---|---|---|
| | I | II | Mean | I | II | Mean |
| let-7a1 | 17.7 | 17.9 | 17.8 | 16.2 | 16.4 | 16.3 |
| mir-16 | 15.9 | 16.2 | 16.0 | 15.0 | 15.2 | 15.1 |
| mir-20 | 19.1 | 19.6 | 19.3 | 18.6 | 18.9 | 18.7 |
| mir-21 | 16.9 | 17.2 | 17.0 | 15.7 | 15.9 | 15.8 |
| mir-22 | 21.4 | 21.7 | 21.6 | 20.3 | 20.5 | 20.4 |
| mir-26a | 15.0 | 15.4 | 15.2 | 14.3 | 14.4 | 14.3 |
| mir-29 | 17.9 | 18.0 | 17.9 | 16.7 | 16.8 | 16.8 |
| mir-30a | 20.6 | 20.8 | 20.7 | 19.8 | 20.0 | 19.9 |
| mir-34 | 21.1 | 21.5 | 21.3 | 20.4 | 20.5 | 20.4 |
| mir-200b | 19.8 | 20.0 | 19.9 | 19.2 | 19.3 | 19.2 |
| mir-323 | 32.3 | 32.6 | 32.5 | 31.1 | 31.2 | 31.2 |
| mir-324-5 | 24.6 | 24.8 | 24.7 | 23.0 | 23.3 | 23.1 |
| Average | 20.2 | 20.5 | 20.3 | 19.2 | 19.4 | 19.3 |

Example 5

An experiment was performed to determine the effect of sample material on Ct values in a real-time miRNA amplification reaction. Here, cells, GuHCl lysate, Tris lysate, and Purified RNA were compared. The cells were NIH3T3 cells. The Purified RNA was collected using the commercially available mirVana mRNA isolation kit for Ambion (catalog number 1560). ATris lysate, and a Guanidine lysate (GuHCl) (commercially available from Applied Biosystems), were prepared as follows:

For the Tris lysate, a 1× lysis buffer comprised 10 mM Tris-HCl, pH 8.0, 0.02% Sodium Azide, and 0.03% Tween-20. Trypsinized cells were pelleted by centrifugation at 1500 rpm for 5 minutes. The growth media was removed by aspiration, being careful that the cell pellet was not disturbed. PBS was added to bring the cells to $2 \times 10^3$ cells/ul. Next 10 ul of cell suspension was mixed with 10 ul of a 2× lysis buffer and spun briefly. The tubes were then immediately incubated for 5 minutes at 95 C, and then immediately placed in a chilled block on ice for 2 minutes. The tubes were then mixed well and spun briefly at full speed before use (or optionally, stored at −20 C).

For the GuHCl lysate, a 1× lysis buffer comprised 2.5M GuHCl, 150 mM MES pH 6.0, 200 mM NaCl, 0.75% Tween-20. Trypsinized cells were pelleted by centrifugation at 1500 rpm for 5 minutes. The growth media was removed by aspiration, being careful that the cell pellet was not disturbed. The cell pellet was then re-suspended in 1×PBS, Ca++ and Mg++ free to bring cells to $2 \times 10^4$ cells/uL. Then, 1 volume of 2× lysis buffer was added. To ensure complete nucleic acid release, this was followed by pipetting up and down ten times, followed by a brief spin. Results are shown in Table 6.

Similar results were obtained for a variety of cell lines, including NIH/3T3, OP9, A549, and HepG2 cells.

TABLE 6

| | Ct | | | |
|---|---|---|---|---|
| miRNA ID | Cells | GuHCl lysate | Tris lysate | Purified RNA |
| let-7a1 | 24.9 | 31.3 | 28.2 | 31.5 |
| mir-16 | 22.3 | 25.2 | 22.3 | 24.9 |
| mir-20 | 22.7 | 26.0 | 24.1 | 26.1 |

TABLE 6-continued

| miRNA ID | Ct | | | |
|---|---|---|---|---|
| | Cells | GuHCl lysate | Tris lysate | Purified RNA |
| mir-21 | 21.3 | 24.2 | 22.0 | 24.7 |
| mir-22 | 30.3 | 28.6 | 27.2 | 28.8 |
| mir-26a | 25.6 | 31.0 | 27.9 | 31.4 |
| mir-29 | 27.2 | 27.9 | 26.5 | 27.4 |
| mir-30a | 26.1 | 32.2 | 28.9 | 30.7 |
| mir-34 | 26.8 | 30.3 | 26.4 | 27.4 |
| mir-200b | 40.0 | 40.0 | 40.0 | 40.0 |
| mir-323 | 30.1 | 34.7 | 31.1 | 31.8 |
| mir-324-5 | 28.6 | 29.7 | 28.3 | 29.3 |
| Average | 27.2 | 30.1 | 27.8 | 29.5 |

Example 6

An experiment was performed to demonstrate the ability of the reaction to selectively quantity mature miRNA in the presence of precursor miRNA. Here, let-7a miRNA and mir-26b miRNA were queried in both mature form as well as in their precursor form. Experiments were performed essentially as described for Example 1 in the no ligase condition, done in triplicate, with varying amounts of target material as indicated. Results are shown in Table 7. The sequences examined were as follows:

```
Mature let-7a, Seq ID NO: 50
UGAGGUAGUAGGUUGUAUAGUU

Precursor let-7a, SEQ ID NO: 51 (Note that the
underlined sequences corresponds to the Mature
let-7a.)
GGGUGAGGUAGUAGGUUGUAUAGUUUGGGGCUCUGCCCUGCUAUGGGA

UAACUAUACAAUCUACUGUCUUUCCU

Mature mir-26b, SEQ ID NO: 52
UUCAAGUAAUUCAGGAUAGGU

Precursor mir-26b of SEQ ID NO: 53 (Note that the
underlined sequences corresponds to the Mature
mir-26b.)
CCGGGACCCAGUUCAAGUAAUUCAGGAUAGGUUGUGUGCUGUCCAGCCU

GUUCUCCAUUACUUGGCUCGGGGACCGG
```

TABLE 7

| Target | Mouse lung RNA (ng) | Synthetic miRNA (fM) | Synthetic precursor (fM) | Assay specific for (CT) | |
|---|---|---|---|---|---|
| | | | | miRNA | Precursor |
| Let-7a | 0 | 0 | 0 | 40.0 ± 0.0 | 40.0 ± 0.0 |
| (let-7a3) | 0 | 10 | 0 | 24.2 ± 0.3 | 40.0 ± 0.0 |
| | 0 | 100 | 0 | 21.0 ± 0.2 | 40.0 ± 0.0 |
| | 0 | 0 | 10 | 35.0 ± 1.0 | 25.0 ± 0.1 |
| | 0 | 0 | 100 | 31.0 ± 0.1 | 21.5 ± 0.1 |
| | 10 | 0 | 0 | 19.1 ± 0.4 | 40.0 ± 0.0 |
| Mir-26b | 0 | 0 | 0 | 40.0 ± 0.0 | 40.0 ± 0.0 |
| | 0 | 10 | 0 | 23.1 ± 0.1 | 40.0 ± 0.0 |
| | 0 | 100 | 0 | 19.7 ± 0.1 | 40.0 ± 0.0 |
| | 0 | 0 | 10 | 32.9 ± 0.4 | 25.7 ± 0.0 |
| | 0 | 0 | 100 | 28.9 ± 0.2 | 22.3 ± 0.0 |
| | 10 | 0 | 0 | 20.5 ± 0.1 | 28.0 ± 0.2 |

Example 7

An experiment was performed on synthetic let-7a miRNA to assess the number of 3' nucleotides in the 3' target specific portion of the linker probe that correspond with the 3' end region of the miRNA. The experiment was performed as essentially as described supra for Example 1 for the no ligase condition, and results are shown in Table 8 as means and standard deviations of Ct values.

TABLE 8

| miRNA assay components: let-7a | | | | | |
|---|---|---|---|---|---|
| miRNA synthetic target: let-7a | | | | | |
| No. 3' ssDNA linker probe target specific portion bases | $C_T$ values & statistics | | | | |
| | I | II | III | Average | SD |
| 7 | 29.4 | 29.1 | 29.3 | 29.3 | 0.1 |
| 6 | 30.1 | 29.9 | 30.2 | 30.1 | 0.2 |
| 5 | 33.9 | 33.2 | 33.8 | 33.6 | 0.4 |
| 4 | 40.0 | 39.2 | 40.0 | 39.7 | 0.4 |

In some embodiments, 3' target specific portions of linker probes preferably comprise 5 nucleotides that correspond to the 3' end region of miRNAs. For example, miR-26a and miR-26b differ by only 2 bases, one of which is the 3' end nucleotide of miR-26a. Linker probes comprising 5 nucleotides at their 3' target specific portions can be employed to selectively detect miR-26a versus miR-26b.

Additional strategies for using the linker probes of the present teachings in the context of single step assays, as well as in the context of short primer compositions, can be found in filed U.S. Provisional application "Compositions, Methods, and Kits for Identifying and Quantitating Small RNA Molecules" by Lao and Straus, as well as in Elfaitouri et al., J. Clin. Virol. 2004, 30(2): 150-156.

The present teachings further contemplate linker probe compositions comprising 3' target specific portions corresponding to any micro RNA sequence, including but without limitation, those sequences shown in Table 9, including *C. elegans* (cel), mouse (mmu), human (hsa), *drosophila* (dme), rat (rno), and rice (osa).

TABLE 9

| | SEQ ID NO: |
|---|---|
| cel-let-7<br>ugagguaguagguuguauaguu | 54 |
| cel-lin-4<br>ucccugagaccucaaguguga | 55 |
| cel-miR-1<br>uggaauguaaagaaguaugua | 56 |
| cel-miR-2<br>uaucacagccagcuuugaugugc | 57 |
| cel-miR-34<br>aggcagugugguuagcugguug | 58 |
| cel-miR-35<br>ucaccggguggaaacuagcagu | 59 |
| cel-miR-36<br>ucaccggguggaaaauucgcaug | 60 |
| cel-miR-37<br>ucaccggguggaacacuugcagu | 61 |
| cel-miR-38<br>ucaccgggagaaaaacuggagu | 62 |

TABLE 9-continued

| | SEQ ID NO: |
|---|---|
| cel-miR-39<br>ucaccgggguguaaaucagcuug | 63 |
| cel-miR-40<br>ucaccgggguguacaucagcuaa | 64 |
| cel-miR-41<br>ucaccgggugaaaaaucaccua | 65 |
| cel-miR-42<br>caccggguuaacaucuacag | 66 |
| cel-miR-43<br>uaucacaguuuacuugcugucgc | 67 |
| cel-miR-44<br>ugacuagagacacauucagcu | 68 |
| cel-miR-45<br>ugacuagagacacauucagcu | 69 |
| cel-miR-46<br>ugucauggagucgcucucuuca | 70 |
| cel-miR-47<br>ugucauggaggcgcucucuuca | 71 |
| cel-miR-48<br>ugagguaggcucaguagaugcga | 72 |
| cel-miR-49<br>aagcaccacgagaagcugcaga | 73 |
| cel-miR-50<br>ugauaugucugguauucuggguu | 74 |
| cel-miR-51<br>uacccguagcuccuauccauguu | 75 |
| cel-miR-52<br>cacccguacauauguuuccgugcu | 76 |
| cel-miR-53<br>cacccguacauuuguuuccgugcu | 77 |
| cel-miR-54<br>uacccguaaucuucauaauccgag | 78 |
| cel-miR-55<br>uacccguauaaguuucugcugag | 79 |
| cel-miR-56*<br>uggcggauccauuuugggguugua | 80 |
| cel-miR-56<br>uacccguaauguuuccgcugag | 81 |
| cel-miR-57<br>uacccuguagaucgagcugugugu | 82 |
| cel-miR-58<br>ugagaucguucaguacggcaau | 83 |
| cel-miR-59<br>ucgaaucguuuaucaggaugaug | 84 |
| cel-miR-60<br>uauuaugcacauuuucaguuca | 85 |
| cel-miR-61<br>ugacuagaaccguuacucaucuc | 86 |
| cel-miR-62<br>ugauauguaaucuagcuuacag | 87 |
| cel-miR-63<br>uaugacacugaagcgaguuggaaa | 88 |

TABLE 9-continued

| | SEQ ID NO: |
|---|---|
| cel-miR-64<br>uaugacacugaagcguuaccgaa | 89 |
| cel-miR-65<br>uaugacacugaagcguaaccgaa | 90 |
| cel-miR-66<br>caugacacugauuagggauguga | 91 |
| cel-miR-67<br>ucacaaccuccuagaaagaguaga | 92 |
| cel-miR-68<br>ucgaagacucaaaaguguaga | 93 |
| cel-miR-69<br>ucgaaaauuaaaaaguguaga | 94 |
| cel-miR-70<br>uaauacgucguugguguuuccau | 95 |
| cel-miR-71<br>ugaaagacauggguaguga | 96 |
| cel-miR-72<br>aggcaagauguuggcauagc | 97 |
| cel-miR-73<br>uggcaagauguaggcaguucagu | 98 |
| cel-miR-74<br>uggcaagaaauggcagucuaca | 99 |
| cel-miR-75<br>uuaaagcuaccaaccggcuuca | 100 |
| cel-miR-76<br>uucguuguugaugaagccuuga | 101 |
| cel-miR-77<br>uucaucaggccauagcugucca | 102 |
| cel-miR-78<br>uggaggccugguuguuugugc | 103 |
| cel-miR-79<br>auaaagcuagguuaccaaagcu | 104 |
| cel-miR-227<br>agcuuucgacaugauucugaac | 105 |
| cel-miR-80<br>ugagaucauuaguugaaagccga | 106 |
| cel-miR-81<br>ugagaucaucgugaaagcuagu | 107 |
| cel-miR-82<br>ugagaucaucgugaaagccagu | 108 |
| cel-miR-83<br>uagcaccauauaaauucaguaa | 109 |
| cel-miR-84<br>ugagguaguauguaauauugua | 110 |
| cel-miR-85<br>uacaaaguauuugaaaagucgugc | 111 |
| cel-miR-86<br>uaagugaaugcuuugccacaguc | 112 |
| cel-miR-87<br>gugagcaaaaguuucaggugu | 113 |

TABLE 9-continued

| | SEQ ID NO: |
|---|---|
| cel-miR-90<br>ugauauguuguuugaaugcccc | 114 |
| cel-miR-124<br>uaaggcacgcggugaaugcca | 115 |
| cel-miR-228<br>aauggcacugcaugaauucacgg | 116 |
| cel-miR-229<br>aaugacacugguuaucuuuuccaucgu | 117 |
| cel-miR-230<br>guauuaguugugcgaccaggaga | 118 |
| cel-miR-231<br>uaagcucgugaucaacaggcagaa | 119 |
| cel-miR-232<br>uaaaugcaucuuaacugcgguga | 120 |
| cel-miR-233<br>uugagcaaugcgcaugugcggga | 121 |
| cel-miR-234<br>uuauugcucgagaauacccuu | 122 |
| cel-miR-235<br>uauugcacucucccggccuga | 123 |
| cel-miR-236<br>uaauacugucagguaaugacgcu | 124 |
| cel-miR-237<br>ucccugagaauucucgaacagcuu | 125 |
| cel-miR-238<br>uuuguacuccgaugccauucaga | 126 |
| cel-miR-239a<br>uuuguacuacacauagguacugg | 127 |
| cel-miR-239b<br>uuguacuacacaaaaguacug | 128 |
| cel-miR-240<br>uacuggcccccaaaucuucgcu | 129 |
| cel-miR-241<br>ugagguaggugcgagaaauga | 130 |
| cel-miR-242<br>uugcguaggccuuugcuucga | 131 |
| cel-miR-243<br>cgguacgaucgcggcgggauauc | 132 |
| cel-miR-244<br>ucuuugguuguacaaaguggguaug | 133 |
| cel-miR-245<br>auuggucccccuccaaguagcuc | 134 |
| cel-miR-246<br>uuacauguuucggguaggagcu | 135 |
| cel-miR-247<br>ugacuagagccuauucucuucuu | 136 |
| cel-miR-248<br>uacacgugcacggauaacgcuca | 137 |
| cel-miR-249<br>ucacaggacuuuugagcguugc | 138 |

TABLE 9-continued

| | SEQ ID NO: |
|---|---|
| cel-miR-250<br>ucacagucaacuguuggcaugg | 139 |
| cel-miR-251<br>uuaaguaguggugccgcucuuauu | 140 |
| cel-miR-252<br>uaaguaguagugccgcagguaac | 141 |
| cel-miR-253<br>cacaccucacuaacacugacc | 142 |
| cel-miR-254<br>ugcaaaucuuucgcgacuguagg | 143 |
| cel-miR-256<br>uggaaugcauagaagacugua | 144 |
| cel-miR-257<br>gaguaucaggaguacccaguga | 145 |
| cel-miR-258<br>gguuuugagaggaauccuuuu | 146 |
| cel-miR-259<br>aaaucucauccuaaucuggua | 147 |
| cel-miR-260<br>gugaugucgaacucuuguag | 148 |
| cel-miR-261<br>uagcuuuuuaguuuucacg | 149 |
| cel-miR-262<br>guuucucgauguuuucugau | 150 |
| cel-miR-264<br>ggcggguggguguuguuaug | 151 |
| cel-miR-265<br>ugagggaggaagggugguau | 152 |
| cel-miR-266<br>aggcaagacuuuggcaaagc | 153 |
| cel-miR-267<br>cccgugaagugucugcugca | 154 |
| cel-miR-268<br>ggcaagaauuagaagcaguuuggu | 155 |
| cel-miR-269<br>ggcaagacucuggcaaaacu | 156 |
| cel-miR-270<br>ggcaugauguagcaguggag | 157 |
| cel-miR-271<br>ucgccggguggggaaagcauu | 158 |
| cel-miR-272<br>uguaggcaugggguguuug | 159 |
| cel-miR-273<br>ugcccguacugugucggcug | 160 |
| cel-miR-353<br>caauugccaugguguuggauu | 161 |
| cel-miR-354<br>accuuguuuguugcugcuccu | 162 |
| cel-miR-355<br>uuuguuuuagccugagcuaug | 163 |

TABLE 9-continued

| | SEQ ID NO: |
|---|---|
| cel-miR-356<br>uugagcaacgcgaacaaauca | 164 |
| cel-miR-357<br>uaaaugccagucguugcagga | 165 |
| cel-miR-358<br>caauugguaucccugucaagg | 166 |
| cel-miR-359<br>ucacuggucuuucucugacga | 167 |
| cel-miR-360<br>ugaccguaaucccguucacaa | 168 |
| cel-lsy-6<br>uuuuguaugagacgcauuucg | 169 |
| cel-miR-392<br>uaucaucgaucacgugugauga | 170 |
| hsa-let-7a<br>ugagguaguagguuguauaguu | 171 |
| hsa-let-7b<br>ugagguaguagguugugugguu | 172 |
| hsa-let-7c<br>ugagguaguagguuguaugguu | 173 |
| hsa-let-7d<br>agagguaguagguugcauagu | 174 |
| hsa-let-7e<br>ugagguaggagguuguauagu | 175 |
| hsa-let-7f<br>ugagguaguagauuguauaguu | 176 |
| hsa-miR-15a<br>uagcagcacauaaugguuugug | 177 |
| hsa-miR-16<br>uagcagcacguaaauauuggcg | 178 |
| hsa-miR-17-5p<br>caaagugcuuacagugcagguagu | 179 |
| hsa-miR-17-3p<br>acugcagugaaggcacuugu | 180 |
| hsa-miR-18<br>uaaggugcaucuagugcagaua | 181 |
| hsa-miR-19a<br>ugugcaaaucuaugcaaaacuga | 182 |
| hsa-miR-19b<br>ugugcaaauccaugcaaaacuga | 183 |
| hsa-miR-20<br>uaaagugcuuauagugcaggua | 184 |
| hsa-miR-21<br>uagcuuaucagacugauguuga | 185 |
| hsa-miR-22<br>aagcugccaguugaagaacugu | 186 |
| hsa-miR-23a<br>aucacauugccagggauuucc | 187 |
| hsa-miR-189<br>gugccacugagcugauaucagu | 188 |

TABLE 9-continued

| | SEQ ID NO: |
|---|---|
| hsa-miR-24<br>uggcucaguucagcaggaacag | 189 |
| hsa-miR-25<br>cauugcacuugucucggucuga | 190 |
| hsa-miR-26a<br>uucaaguaauccaggauaggcu | 191 |
| hsa-miR-26b<br>uucaaguaauucaggauaggu | 192 |
| hsa-miR-27a<br>uucacaguggcuaaguuccgcc | 193 |
| hsa-miR-28<br>aaggagcucacagucuauugag | 194 |
| hsa-miR-29a<br>cuagcaccaucugaaaucgguu | 195 |
| hsa-miR-30a*<br>uguaaacauccucgacuggaagc | 196 |
| hsa-miR-30a<br>cuuucagucggauguuugcagc | 197 |
| hsa-miR-31<br>ggcaagaugcuggcauagcug | 198 |
| hsa-miR-32<br>uauugcacauuacuaaguugc | 199 |
| hsa-miR-33<br>gugcauuguaguugcauug | 200 |
| hsa-miR-92<br>uauugcacuugucccggccugu | 201 |
| hsa-miR-93<br>aaagugcuguucgugcagguag | 202 |
| hsa-miR-95<br>uucaacggguauuuauugagca | 203 |
| hsa-miR-96<br>uuuggcacuagcacauuuugc | 204 |
| hsa-miR-98<br>ugagguaguaaguuguauuguu | 205 |
| hsa-miR-99a<br>aacccguagauccgaucuugug | 206 |
| hsa-miR-100<br>aacccguagauccgaacuugug | 207 |
| hsa-miR-101<br>uacaguacugugauaacugaag | 208 |
| hsa-miR-29b<br>uagcaccauuugaaaucagu | 209 |
| hsa-miR-103<br>agcagcauuguacagggcuauga | 210 |
| hsa-miR-105<br>ucaaaugcucagacuccugu | 211 |
| hsa-miR-106a<br>aaaagugcuuacagugcagguagc | 212 |
| hsa-miR-107<br>agcagcauuguacagggcuauca | 213 |

TABLE 9-continued

| | SEQ ID NO: |
|---|---|
| hsa-miR-192<br>cugaccuaugaauugacagcc | 214 |
| hsa-miR-196<br>uagguaguuucauguuguugg | 215 |
| hsa-miR-197<br>uucaccaccuucuccacccagc | 216 |
| hsa-miR-198<br>gguccagaggggagauagg | 217 |
| hsa-miR-199a<br>cccaguguucagacuaccuguuc | 218 |
| hsa-miR-199a*<br>uacaguagucugcacauugguu | 219 |
| hsa-miR-208<br>auaagacgagcaaaaagcuugu | 220 |
| hsa-miR-148a<br>ucagugcacuacagaacuuugu | 221 |
| hsa-miR-30c<br>uguaaacauccuacacucucagc | 222 |
| hsa-miR-30d<br>uguaaacauccccgacuggaag | 223 |
| hsa-miR-139<br>ucuacagugcacgugucu | 224 |
| hsa-miR-147<br>guguguggaaaugcuucugc | 225 |
| hsa-miR-7<br>uggaagacuagugauuuuguu | 226 |
| hsa-miR-10a<br>uacccuguagauccgaauuugug | 227 |
| hsa-miR-10b<br>uacccuguagaaccgaauuugu | 228 |
| hsa-miR-34a<br>uggcagugucuuagcugguugu | 229 |
| hsa-miR-181a<br>aacauucaacgcugucggugagu | 230 |
| hsa-miR-181b<br>aacauucauugcugucgguggguu | 231 |
| hsa-miR-181c<br>aacauucaaccugucggugagu | 232 |
| hsa-miR-182<br>uuuggcaauggguagaacucaca | 233 |
| hsa-miR-182*<br>ugguucuagacuugccaacua | 234 |
| hsa-miR-183<br>uauggcacugguagaauucacug | 235 |
| hsa-miR-187<br>ucgugucuuguguugcagccg | 236 |
| hsa-miR-199b<br>cccaguguuuagacuaucuguuc | 237 |
| hsa-miR-203<br>gugaaauguuuaggaccacuag | 238 |
| hsa-miR-204<br>uucccuuugucauccuaugccu | 239 |
| hsa-miR-205<br>uccuucauuccaccggagucug | 240 |
| hsa-miR-210<br>cugugcgugugacagcggcug | 241 |
| hsa-miR-211<br>uucccuuugucauccuucgccu | 242 |
| hsa-miR-212<br>uaacagucuccagucacggcc | 243 |
| hsa-miR-213<br>accaucgaccguugauuguacc | 244 |
| hsa-miR-214<br>acagcaggcacagacaggcag | 245 |
| hsa-miR-215<br>augaccuaugaauugacagac | 246 |
| hsa-miR-216<br>uaaucucagcuggcaacugug | 247 |
| hsa-miR-217<br>uacugcaucaggaacugauuggau | 248 |
| hsa-miR-218<br>uugugcuugaucuaaccaugu | 249 |
| hsa-miR-219<br>ugauuguccaaacgcaauucu | 250 |
| hsa-miR-220<br>ccacaccguaucugacacuuu | 251 |
| hsa-miR-221<br>agcuacauugucugcuggguuuc | 252 |
| hsa-miR-222<br>agcuacaucuggcuacugggucuc | 253 |
| hsa-miR-223<br>ugucaguuugucaaauacccc | 254 |
| hsa-miR-224<br>caagucacuagugguuccguuua | 255 |
| hsa-miR-200b<br>cucuaauacugccugguaaugaug | 256 |
| hsa-let-7g<br>ugagguaguaguuuguacagu | 257 |
| hsa-let-7i<br>ugagguaguaguuugugcu | 258 |
| hsa-miR-1<br>uggaauguaaagaaguaugua | 259 |
| hsa-miR-15b<br>uagcagcacaucaugguuuaca | 260 |
| hsa-miR-23b<br>aucacauugccagggauuaccac | 261 |
| hsa-miR-27b<br>uucacaguggcuaaguucug | 262 |
| hsa-miR-30b<br>uguaaacauccuacacucagc | 263 |

TABLE 9-continued

| | SEQ ID NO: |
|---|---|
| hsa-miR-122a<br>uggagugugacaaugguguuugu | 264 |
| hsa-miR-124a<br>uuaaggcacgcggugaaugcca | 265 |
| hsa-miR-125b<br>ucccugagacccuaacuuguga | 266 |
| hsa-miR-128a<br>ucacagugaaccggucucuuuu | 267 |
| hsa-miR-130a<br>cagugcaauguuaaaagggc | 268 |
| hsa-miR-132<br>uaacagucuacagccauggucg | 269 |
| hsa-miR-133a<br>uuggucccuucaaccagcugu | 270 |
| hsa-miR-135a<br>uauggcuuuuauuccuauguga | 271 |
| hsa-miR-137<br>uauugcuuaagaauacgcguag | 272 |
| hsa-miR-138<br>agcugguguugugaauc | 273 |
| hsa-miR-140<br>agugguuuuacccuauggUag | 274 |
| hsa-miR-141<br>aacacugucugguaaagaugg | 275 |
| hsa-miR-142-5p<br>cauaaaguagaaagcacuac | 276 |
| hsa-miR-142-3p<br>uguaguguuuccuacuuuaugga | 277 |
| hsa-miR-143<br>ugagaugaagcacuguagcuca | 278 |
| hsa-miR-144<br>uacaguauagaugauguacuag | 279 |
| hsa-miR-145<br>guccaguuuucccaggaaucccuu | 280 |
| hsa-miR-152<br>ucagugcaugacagaacuugg | 281 |
| hsa-miR-153<br>uugcauagucacaaaaguga | 282 |
| hsa-miR-191<br>caacggaaucccaaaagcagcu | 283 |
| hsa-miR-9<br>ucuuugguuaucuagcuauga | 284 |
| hsa-miR-9*<br>uaaagcuagauaaccgaaagu | 285 |
| hsa-miR-125a<br>ucccugagacccuuuaaccugug | 286 |
| hsa-miR-126*<br>cauuauuacuuuugguacgcg | 287 |
| hsa-miR-126<br>ucguaccgugaguaauaaugc | 288 |
| hsa-miR-127<br>ucggauccgucugagcuuggcu | 289 |
| hsa-miR-129<br>cuuuuugcggucugggcuugc | 290 |
| hsa-miR-134<br>ugugacugguugaccagaggg | 291 |
| hsa-miR-136<br>acuccauuuguuuugaugaugga | 292 |
| hsa-miR-146<br>ugagaacugaauuccaugggUu | 293 |
| hsa-miR-149<br>ucuggcuccgugucuucacucc | 294 |
| hsa-miR-150<br>ucucccaacccuuguaccagug | 295 |
| hsa-miR-154<br>uagguuauccguguugccuucg | 296 |
| hsa-miR-184<br>uggacggagaacugauaagggu | 297 |
| hsa-miR-185<br>uggagagaaaggcaguuc | 298 |
| hsa-miR-186<br>caaagaauucuccuuuugggcuu | 299 |
| hsa-miR-188<br>caucccuugcauggugagggu | 300 |
| hsa-miR-190<br>ugauauguuugauauauuaggu | 301 |
| hsa-miR-193<br>aacuggccuacaaagucccag | 302 |
| hsa-miR-194<br>uguaacagcaacuccaugugga | 303 |
| hsa-miR-195<br>uagcagcacagaaauauuggc | 304 |
| hsa-miR-206<br>uggaauguaaggaagugugugg | 305 |
| hsa-miR-320<br>aaaagcuggguugagagggcgaa | 306 |
| hsa-miR-321<br>uaagccagggauguggguuc | 307 |
| hsa-miR-200c<br>aauacugccggguaaugauga | 308 |
| hsa-miR-155<br>uuaaugcuaaucugauagggg | 309 |
| hsa-miR-128b<br>ucacagugaaccggucucuuuc | 310 |
| hsa-miR-106b<br>uaaagcugacagugcagau | 311 |
| hsa-miR-29c<br>uagcaccauuugaaaucgguua | 312 |
| hsa-miR-200a<br>uaacacugucugguaacgaugu | 313 |

TABLE 9-continued

| | SEQ ID NO: |
|---|---|
| hsa-miR-302<br>uaagugcuuccauguuuugguga | 314 |
| hsa-miR-34b<br>aggcagugucauuagcugauug | 315 |
| hsa-miR-34c<br>aggcaguguaguuagcugauug | 316 |
| hsa-miR-299<br>ugguuuaccgucccacauacau | 317 |
| hsa-miR-301<br>cagugcaauaguauugucaaagc | 318 |
| hsa-miR-99b<br>cacccg uagaaccgaccuugcg | 319 |
| hsa-miR-296<br>agggccccccucaauccugu | 320 |
| hsa-miR-130b<br>cagugcaaugaugaaagggcau | 321 |
| hsa-miR-30e<br>uguaaacauccuugacugga | 322 |
| hsa-miR-340<br>uccgucucaguuacuuuauagcc | 323 |
| hsa-miR-330<br>gcaaagcacacggccugcagaga | 324 |
| hsa-miR-328<br>cuggcccucucugcccuuccgu | 325 |
| hsa-miR-342<br>ucucacacagaaaucgcacccguc | 326 |
| hsa-miR-337<br>uccagcuccuauaugaugccuuu | 327 |
| hsa-miR-323<br>gcacauuacacggucgaccucu | 328 |
| hsa-miR-326<br>ccucugggcccuuccuccag | 329 |
| hsa-miR-151<br>acuagacugaagcuccuugagg | 330 |
| hsa-miR-135b<br>uauggcuuuucauuccuaugug | 331 |
| hsa-miR-148b<br>ucagugcaucacagaacuuugu | 332 |
| hsa-miR-331<br>gccccugggccuauccuagaa | 333 |
| hsa-miR-324-5p<br>cgcaucccuagggcauuggugu | 334 |
| hsa-miR-324-3p<br>ccacugccccaggugcugcugg | 335 |
| hsa-miR-338<br>uccagcaucagugauuuuguuga | 336 |
| hsa-miR-339<br>ucccuguccuccaggagcuca | 337 |
| hsa-miR-335<br>ucaagagcaauaacgaaaaugu | 338 |

TABLE 9-continued

| | SEQ ID NO: |
|---|---|
| hsa-miR-133b<br>uugguccccuucaaccagcua | 339 |
| osa-miR156<br>ugacagaagagagugagcac | 340 |
| osa-miR160<br>ugccuggcucccuguaugcca | 341 |
| osa-miR162<br>ucgauaaaccucugcauccag | 342 |
| osa-miR164<br>uggagaagcagggcacgugca | 343 |
| osa-miR166<br>ucggaccaggcuucauccccc | 344 |
| osa-miR167<br>ugaagcugccagcaugaucua | 345 |
| osa-miR169<br>cagccaaggaugacuugccga | 346 |
| osa-miR171<br>ugauugagccgcgccaauauc | 347 |
| mmu-let-7g<br>ugagguaguaguuuguacagu | 348 |
| mmu-let-7i<br>ugagguaguaguuugugcu | 349 |
| mmu-miR-1<br>uggaauguaaagaaguaugua | 350 |
| mmu-miR-15b<br>uagcagcacaucaugguuuaca | 351 |
| mmu-miR-23b<br>aucacauugccagggauuaccac | 352 |
| mmu-miR-27b<br>uucacaguggcuaaguucug | 353 |
| mmu-miR-29b<br>uagcaccauuugaaaucagugu | 354 |
| mmu-miR-30a*<br>uguaaacauccucgacuggaagc | 355 |
| mmu-miR-30a<br>cuuucagucggauguuugcagc | 356 |
| mmu-miR-30b<br>uguaaacauccuacacucagc | 357 |
| mmu-miR-99a<br>acccguagauccgaucuugu | 358 |
| mmu-miR-99b<br>cacccguagaaccgaccuugcg | 359 |
| mmu-miR-101<br>uacaguacugugauaacuga | 360 |
| mmu-miR-124a<br>uuaaggcacgcggugaaugcca | 361 |
| mmu-miR-125a<br>ucccugagacccuuuaaccugug | 362 |
| mmu-miR-125b<br>ucccugagacccuaacuuguga | 363 |

TABLE 9-continued

| | SEQ ID NO: |
|---|---|
| mmu-miR-126* cauuauuacuuuugguacgcg | 364 |
| mmu-miR-126 ucguaccgugaguaauaaugc | 365 |
| mmu-miR-127 ucggauccgucugagcuuggcu | 366 |
| mmu-miR-128a ucacagugaaccggucucuuuu | 367 |
| mmu-miR-130a cagugcaauguuaaaagggc | 368 |
| mmu-miR-9 ucuuugguuaucuagcuauga | 369 |
| mmu-miR-9* uaaagcuagauaaccgaaagu | 370 |
| mmu-miR-132 uaacagucuacagccauggucg | 371 |
| mmu-miR-133a uuggcccccuucaaccagcugu | 372 |
| mmu-miR-134 ugugacugguugaccagaggg | 373 |
| mmu-miR-135a uauggcuuuuuauuccuauguga | 374 |
| mmu-miR-136 acuccauuuguuuugaugaugga | 375 |
| mmu-miR-137 uauugcuuaagaauacgcguag | 376 |
| mmu-miR-138 agcugguguugugaauc | 377 |
| mmu-miR-140 agugguuuuacccuaugguag | 378 |
| mmu-miR-141 aacacugucugguaaagaugg | 379 |
| mmu-miR-142-5p cauaaaguagaaagcacuac | 380 |
| mmu-miR-142-3p uguaguguuuccuacuuuaugg | 381 |
| mmu-miR-144 uacaguauagaugauguacuag | 382 |
| mmu-miR-145 guccaguuuucccaggaaucccuu | 383 |
| mmu-miR-146 ugagaacugaauuccaugggguu | 384 |
| mmu-miR-149 ucuggcuccgugucuucacucc | 385 |
| mmu-miR-150 ucucccaacccuuguaccagug | 386 |
| mmu-miR-151 cuagacugaggcuccuugagg | 387 |
| mmu-miR-152 ucagugcaugacagaacuugg | 388 |

TABLE 9-continued

| | SEQ ID NO: |
|---|---|
| mmu-miR-153 uugcauagucacaaaaguga | 389 |
| mmu-miR-154 uagguuauccguguugccuucg | 390 |
| mmu-miR-155 uuaaugcuaauugugauagggg | 391 |
| mmu-miR-10b cccuguagaaccgaauuugugu | 392 |
| mmu-miR-129 cuuuuugcggucugggcuugcu | 393 |
| mmu-miR-181a aacauucaacgcugucggugagu | 394 |
| mmu-miR-182 uuuggcaaugguagaacucaca | 395 |
| mmu-miR-183 uauggcacugguagaauucacug | 396 |
| mmu-miR-184 uggacggagaacugauaagggu | 397 |
| mmu-miR-185 uggagagaaaggcaguuc | 398 |
| mmu-miR-186 caaagaauucuccuuuugggcuu | 399 |
| mmu-miR-187 ucgugucuuguguugcagccgg | 400 |
| mmu-miR-188 caucccuugcaugguggagggu | 401 |
| mmu-miR-189 gugccuacugagcugauaucagu | 402 |
| mmu-miR-24 uggcucaguucagcaggaacag | 403 |
| mmu-miR-190 ugauauguuugauauauuaggu | 404 |
| mmu-miR-191 caacggaaucccaaaagcagcu | 405 |
| mmu-miR-193 aacuggccuacaaagucccag | 406 |
| mmu-miR-194 uguaacagcaacuccaugugga | 407 |
| mmu-miR-195 uagcagcacagaaauauuggc | 408 |
| mmu-miR-199a cccaguguucagacuaccuguuc | 409 |
| mmu-miR-199a* uacaguagucugcacauugguu | 410 |
| mmu-miR-200b uaauacugccugguaaugaugac | 411 |
| mmu-miR-201 uacucaguaaggcauuguucu | 412 |
| mmu-miR-202 agagguauagcgcaugggaaga | 413 |

TABLE 9-continued

| | SEQ ID NO: |
|---|---|
| mmu-miR-203 ugaaauguuuaggaccacuag | 414 |
| mmu-miR-204 uucccuuugucauccuaugccug | 415 |
| mmu-miR-205 uccuucauuccaccggagucug | 416 |
| mmu-miR-206 uggaauguaaggaagugugugg | 417 |
| mmu-miR-207 gcuucuccuggcucuccucccuc | 418 |
| mmu-miR-122a uggagugugacaauggugungu | 419 |
| mmu-miR-143 ugagaugaagcacuguagcuca | 420 |
| mmu-miR-30e uguaaacauccuugacugga | 421 |
| mmu-miR-290 cucaaacauggggggcacuuuuu | 422 |
| mmu-miR-291-5p caucaaaguggaggcccucucu | 423 |
| mmu-miR-291-3p aaagugcuuccacuuugugugcc | 424 |
| mmu-miR-292-5p acucaaacuggggggcucuuuug | 425 |
| mmu-miR-292-3p aagugccgccagguuuugagugu | 426 |
| mmu-miR-293 agugccgcagaguuuguagugu | 427 |
| mmu-miR-294 aaagugcuucccuuuugugugu | 428 |
| mmu-miR-295 aaagugcuacuacuuugagucu | 429 |
| mmu-miR-296 agggcccccccucaauccugu | 430 |
| mmu-miR-297 auguaugugugcaugugcaug | 431 |
| mmu-miR-298 ggcagaggagggcuguucuucc | 432 |
| mmu-miR-299 ugguuuaccgucccacauacau | 433 |
| mmu-miR-300 uaugcaagggcaagcucucuuc | 434 |
| mmu-miR-301 cagugcaauaguauugucaaagc | 435 |
| mmu-miR-302 uaagugcuuccauguuuugguga | 436 |
| mmu-miR-34c aggcaguguaguuagcugauugc | 437 |
| mmu-miR-34b uaggcaguguaauuagcugauug | 438 |
| mmu-let-7d agagguaguagguugcauagu | 439 |
| mmu-let-7d* cuauacgaccugcugccuuucu | 440 |
| mmu-miR-106a caaagugcuaacagugcaggua | 441 |
| mmu-miR-106b uaaagugcugacagugcagau | 442 |
| mmu-miR-130b cagugcaaugaugaaagggcau | 443 |
| mmu-miR-19b ugugcaaauccaugcaaaacuga | 444 |
| mmu-miR-30c uguaaacauccuacacucucagc | 445 |
| mmu-miR-30d uguaaacauccccgacuggaag | 446 |
| mmu-miR-148a ucagugcacuacagaacuuugu | 447 |
| mmu-miR-192 cugaccuaugaauugaca | 448 |
| mmu-miR-196 uagguaguuucauguuguugg | 449 |
| mmu-miR-200a uaacacugucugguaacgaugu | 450 |
| mmu-miR-208 auaagacgagcaaaaagcuugu | 451 |
| mmu-let-7a ugagguaguagguuguauaguu | 452 |
| mmu-let-7b ugagguaguagguugugugguu | 453 |
| mmu-let-7c ugagguaguagguuguaugguu | 454 |
| mmu-let-7e ugagguaggagguuguauagu | 455 |
| mmu-let-7f ugagguaguagauuguauaguu | 456 |
| mmu-miR-15a uagcagcacauaaugguuugug | 457 |
| mmu-miR-16 uagcagcacguaaauauuggcg | 458 |
| mmu-miR-18 uaaggugcaucuagugcagaua | 459 |
| mmu-miR-20 uaaagugcuuauagugcagguag | 460 |
| mmu-miR-21 uagcuuaucagacugauguuga | 461 |
| mmu-miR-22 aagcugccaguugaagaacugu | 462 |
| mmu-miR-23a aucacauugccagggauuucc | 463 |
| mmu-miR-26a uucaaguaauccaggauaggcu | 464 |

TABLE 9-continued

| | SEQ ID NO: |
|---|---|
| mmu-miR-26b<br>uucaaguaauucaggauagguu | 465 |
| mmu-miR-29a<br>cuagcaccaucugaaaucgguu | 466 |
| mmu-miR-29c<br>uagcaccauuugaaaucgguua | 467 |
| mmu-miR-27a<br>uucacaguggcuaaguuccgc | 468 |
| mmu-miR-31<br>aggcaagaugcuggcauagcug | 469 |
| mmu-miR-92<br>uauugcacuugucccggccug | 470 |
| mmu-miR-93<br>caaagugcuguucgugcagguag | 471 |
| mmu-miR-96<br>uuuggcacuagcacauuuugcu | 472 |
| mmu-miR-34a<br>uggcagugucuuagcugguuguu | 473 |
| mmu-miR-98<br>ugagguaguaaguuguauuguu | 474 |
| mmu-miR-103<br>agcagcauuguacagggcuauga | 475 |
| mmu-miR-323<br>gcacauuacacggucgaccucu | 476 |
| mmu-miR-324-5p<br>cgcauccccuagggcauuggugu | 477 |
| mmu-miR-324-3p<br>ccacugccccaggugcugcugg | 478 |
| mmu-miR-325<br>ccuaguaggugcucaguaagugu | 479 |
| mmu-miR-326<br>ccucugggcccuuccuccagu | 480 |
| mmu-miR-328<br>cuggcccucucugcccuuccgu | 481 |
| mmu-miR-329<br>aacacaccagcuaaccuuuuu | 482 |
| mmu-miR-330<br>gcaaagcacagggccugcagaga | 483 |
| mmu-miR-331<br>gccccugggccuauccuagaa | 484 |
| mmu-miR-337<br>uucagcuccuauaugaugccuuu | 485 |
| mmu-miR-338<br>uccagcaucagugauuuuguuga | 486 |
| mmu-miR-339<br>ucccuguccuccaggagcuca | 487 |
| mmu-miR-340<br>uccgucucaguuacuuuauagcc | 488 |
| mmu-miR-341<br>ucgaucggucggucggucagu | 489 |
| mmu-miR-342<br>ucucacacagaaaucgcacccguc | 490 |

TABLE 9-continued

| | SEQ ID NO: |
|---|---|
| mmu-miR-344<br>ugaucuagccaaagccugacugu | 491 |
| mmu-miR-345<br>ugcugaccccuaguccagugc | 492 |
| mmu-miR-346<br>ugucugcccgagugccugccucu | 493 |
| mmu-miR-350<br>uucacaaagcccauacacuuuac | 494 |
| mmu-miR-135b<br>uauggcuuuucauuccuaugug | 495 |
| mmu-miR-101b<br>uacaguacugugauagcugaag | 496 |
| mmu-miR-107<br>agcagcauuguacagggcuauca | 497 |
| mmu-miR-10a<br>uacccuguagauccgaauuugug | 498 |
| mmu-miR-17-5p<br>caaagugcuuacagugcagguagu | 499 |
| mmu-miR-17-3p<br>acugcagugagggcacugu | 500 |
| mmu-miR-19a<br>ugugcaaaucuaugcaaaacuga | 501 |
| mmu-miR-25<br>cauugcacuugucucggucuga | 502 |
| mmu-miR-28<br>aaggagcucacagucuauugag | 503 |
| mmu-miR-32<br>uauugcacauuacuaaguugc | 504 |
| mmu-miR-100<br>aacccguagauccgaacuugug | 505 |
| mmu-miR-139<br>ucuacagugcacgugucu | 506 |
| mmu-miR-200c<br>aauacugccggguaaugaugga | 507 |
| mmu-miR-210<br>cugugcgugugacagcggcug | 508 |
| mmu-miR-212<br>uaacagucuccagucacggcc | 509 |
| mmu-miR-213<br>accaucgaccguugauuguacc | 510 |
| mmu-miR-214<br>acagcaggcacagacaggcag | 511 |
| mmu-miR-216<br>uaaucucagcuggcaacugug | 512 |
| mmu-miR-218<br>uugugcuugaucuaaccaugu | 513 |
| mmu-miR-219<br>ugauuguccaaacgcaauucu | 514 |
| mmu-miR-223<br>ugucaguuugucaaauacccc | 515 |

TABLE 9-continued

| | SEQ ID NO: |
|---|---|
| mmu-miR-320 aaaagcuggguugagagggcgaa | 516 |
| mmu-miR-321 uaagccagggauguggguuc | 517 |
| mmu-miR-33 gugcauuguaguugcauug | 518 |
| mmu-miR-211 uccccuuugucauccuuugccu | 519 |
| mmu-miR-221 agcuacauugucugcuggguuu | 520 |
| mmu-miR-222 agcuacaucuggcuacugggucu | 521 |
| mmu-miR-224 uaagucacuagugguuccguuua | 522 |
| mmu-miR-199b cccaguguuuagacuaccuguuc | 523 |
| mmu-miR-181b aacauucauugcugucgguggguu | 524 |
| mmu-miR-181c aacauucaaccugucggugagu | 525 |
| mmu-miR-128b ucacagugaaccggcucuuuc | 526 |
| mmu-miR-7 uggaagacuagugauuuuguu | 527 |
| mmu-miR-7b uggaagacuugugauuuuguu | 528 |
| mmu-miR-217 uacugcaucaggaacugacuggau | 529 |
| mmu-miR-133b uuggucccuuucaaccagcua | 530 |
| mmu-miR-215 augaccaugauuugacagac | 531 |
| dme-miR-1 uggaauguaaagaaguauggag | 532 |
| dme-miR-2a uaucacagccagcuuugaugagc | 533 |
| dme-miR-2b uaucacagccagcuuugaggagc | 534 |
| dme-miR-3 ucacugggcaaaguguguguca | 535 |
| dme-miR-4 auaaagcuagacaaccauuga | 536 |
| dme-miR-5 aaaggaacgaucguugugauaug | 537 |
| dme-miR-6 uaucacaguggcuguucuuuuu | 538 |
| dme-miR-7 uggaagacuagugauuuuguugu | 539 |
| dme-miR-8 uaauacugucagguaaagauguc | 540 |

TABLE 9-continued

| | SEQ ID NO: |
|---|---|
| dme-miR-9a ucuuugguuaucuagcuguauga | 541 |
| dme-miR-10 acccuguagauccgaauuugu | 542 |
| dme-miR-11 caucacagucugaguucuugc | 543 |
| dme-miR-12 ugaguauuacaucaguacuggu | 544 |
| dme-miR-13a uaucacagccauuuugaugagu | 545 |
| dme-miR-13b uaucacagccauuuugacgagu | 546 |
| dme-miR-14 ucagucuuuuucucucuccua | 547 |
| dme-miR-263a guuaauggcacuggaagaauucac | 548 |
| dme-miR-184* ccuuaucauucucucgccccg | 549 |
| dme-miR-184 uggacggagaacugauaagggc | 550 |
| dme-miR-274 uuuugugaccgacacuaacggguaau | 551 |
| dme-miR-275 ucagguaccugaaguagcgcgcg | 552 |
| dme-miR-92a cauugcacuuguccccggccuau | 553 |
| dme-miR-219 ugauugcccaaacgcaauucuug | 554 |
| dme-miR-276a* cagcgagguauagaguuccuacg | 555 |
| dme-miR-276a uaggaacuucauaccgugcucu | 556 |
| dme-miR-277 uaaaugcacuaucugguacgaca | 557 |
| dme-miR-278 ucggugggacuuucguccguuu | 558 |
| dme-miR-133 uuggucccuucaaccagcugu | 559 |
| dme-miR-279 ugacuagauccacacucauuaa | 560 |
| dme-miR-33 aggugcauuguagucgcauug | 561 |
| dme-miR-280 uguauuuacguugcauaugaaaugaua | 562 |
| dme-miR-281-1* aagagagcuguccgucgacagu | 563 |
| dme-miR-281 ugucauggaauugcucucuuugu | 564 |
| dme-miR-282 aaucuagccucuacuaggcuuugucugu | 565 |
| dme-miR-283 uaaauaucagcugguaauucu | 566 |

TABLE 9-continued

| | SEQ ID NO: |
|---|---|
| dme-miR-284 ugaagucagcaacuugauuccagcaauug | 567 |
| dme-miR-281-2* aagagagcuauccgucgacagu | 568 |
| dme-miR-34 uggcagugugguuagcugguug | 569 |
| dme-miR-124 uaaggcacgcggugaaugccaag | 570 |
| dme-miR-79 uaaagcuagauuaccaaagcau | 571 |
| dme-miR-276b* cagcgaggauauagaguuccuacg | 572 |
| dme-miR-276b uaggaacuuaauaccgugucucu | 573 |
| dme-miR-210 uugugcgugugacagcggcua | 574 |
| dme-miR-285 uagcaccauucgaaaucagugc | 575 |
| dme-miR-100 aacccguaaauccgaacuugug | 576 |
| dme-miR-92b aauugcacuaguccccggccugc | 577 |
| dme-miR-286 ugacuagaccgaacacucgugcu | 578 |
| dme-miR-287 uguguugaaaaucguuugcac | 579 |
| dme-miR-87 uugagcaaaauuucaggugug | 580 |
| dme-miR-263b cuuggcacugggagaauucac | 581 |
| dme-miR-288 uuucaugucgauuucauuucaug | 582 |
| dme-miR-289 uaaauauuuaaguggagccugcgacu | 583 |
| dme-bantam ugagaucauuuugaaagcugauu | 584 |
| dme-miR-303 uuuagguuucacaggaaacuggu | 585 |
| dme-miR-31b uggcaagaugucggaauagcug | 586 |
| dme-miR-304 uaaucucaauuuguaaaugugag | 587 |
| dme-miR-305 auuguacuucaucaggugcucug | 588 |
| dme-miR-9c ucuuugguauucuagcuguaga | 589 |
| dme-miR-306 ucagguacuuagugacucucaa | 590 |
| dme-miR-306* gggggucacucugugccugugc | 591 |
| dme-miR-9b ucuuugguugauuuuagcuguaug | 592 |

TABLE 9-continued

| | SEQ ID NO: |
|---|---|
| dme-let-7 ugagguaguagguuguauagu | 593 |
| dme-miR-125 ucccugagacccuaacuuguga | 594 |
| dme-miR-307 ucacaaccuccuugagugag | 595 |
| dme-miR-308 aaucacaggauuauacugugag | 596 |
| dme-miR-31a uggcaagaugucggcauagcuga | 597 |
| dme-miR-309 gcacuggguaaaguuuguccua | 598 |
| dme-miR-310 uauugcacacuucccggccuuu | 599 |
| dme-miR-311 uauugcacauucaccggccuga | 600 |
| dme-miR-312 uauugcacuugagacggccuga | 601 |
| dme-miR-313 uauugcacuuuucacagcccga | 602 |
| dme-miR-314 uauucgagccaauaaguucgg | 603 |
| dme-miR-315 uuuugauuguugcucagaaagc | 604 |
| dme-miR-316 ugucuuuuccgcuuacuggcg | 605 |
| dme-miR-317 ugaacacagcuggugguauccagu | 606 |
| dme-miR-318 ucacuggggcuuuguuuaucuca | 607 |
| dme-miR-2c uaucacagccagcuuugauggc | 608 |
| dme-miR-iab-4-5p acguauacugaauguauaccuga | 609 |
| dme-miR-iab-4-3p cgguauaccuucaguauacguaac | 610 |
| rno-miR-322 aaacaugaagcgcugcaaca | 611 |
| rno-miR-323 gcacauuacacggucgaccucu | 612 |
| rno-miR-301 cagugcaauaguauugucaaagcau | 613 |
| rno-miR-324-5p cgcauccccuagggcauuggugu | 614 |
| rno-miR-324-3p ccacugccccaggugcugcugg | 615 |
| rno-miR-325 ccuaguaggugcucaguaagugu | 616 |
| rno-miR-326 ccucugggcccuuccuccagu | 617 |

TABLE 9-continued

| | SEQ ID NO: |
|---|---|
| rno-let-7d<br>agagguaguagguugcauagu | 618 |
| rno-let-7d*<br>cuauacgaccugcugccuuucu | 619 |
| rno-miR-328<br>cuggcccucucugcccuuccgu | 620 |
| rno-miR-329<br>aacacacccagcuaaccuuuuu | 621 |
| rno-miR-330<br>gcaaagcacagggccugcagaga | 622 |
| rno-miR-331<br>gccccugggccuauccuagaa | 623 |
| rno-miR-333<br>guggugugcuaguuacuuuu | 624 |
| rno-miR-140<br>agugguuuuacccuauggu ag | 625 |
| rno-miR-140*<br>uaccacaggguagaaccacggaca | 626 |
| rno-miR-336<br>ucacccuuccauaucuagucu | 627 |
| rno-miR-337<br>uucagcuccuauaugaugccuuu | 628 |
| rno-miR-148b<br>ucagugcaucacagaacuuugu | 629 |
| rno-miR-338<br>uccagcaucagugauuuuguuga | 630 |
| rno-miR-339<br>ucccuguccuccaggagcuca | 631 |
| rno-miR-341<br>ucgaucggucggucggucagu | 632 |
| rno-miR-342<br>ucucacacagaaaucgcacccguc | 633 |
| rno-miR-344<br>ugaucuagccaaagccugaccgu | 634 |
| rno-miR-345<br>ugcugaccccuaguccagugc | 635 |
| rno-miR-346<br>ugucugccugagugccugccucu | 636 |
| rno-miR-349<br>cagcccugcugucuuaaccucu | 637 |
| rno-miR-129<br>cuuuugcggucugggcuugcu | 638 |
| rno-miR-129*<br>aagcccuuaccccaaaaagcau | 639 |
| rno-miR-20<br>uaaagugcuuauagugcagguag | 640 |
| rno-miR-20*<br>acugcauuacgagcacuuaca | 641 |
| rno-miR-350<br>uucacaaagcccauacacuuucac | 642 |

TABLE 9-continued

| | SEQ ID NO: |
|---|---|
| rno-miR-7<br>uggaagacuagugauuuuguu | 643 |
| rno-miR-7*<br>caacaaaucacagucugccaua | 644 |
| rno-miR-351<br>ucccugaggagcccuuugagccug | 645 |
| rno-miR-135b<br>uauggcuuuucauuccuaugug | 646 |
| rno-miR-151*<br>ucgaggagcucacagucuagua | 647 |
| rno-miR-151<br>acuagacugaggcuccuugagg | 648 |
| rno-miR-101b<br>uacaguacugugauagcugaag | 649 |
| rno-let-7a<br>ugagguaguagguuguauaguu | 650 |
| rno-let-7b<br>ugagguaguagguugugugguu | 651 |
| rno-let-7c<br>ugagguaguagguuguaugguu | 652 |
| rno-let-7e<br>ugagguaggagguuguauagu | 653 |
| rno-let-7f<br>ugagguaguagauuguauaguu | 654 |
| rno-let-7i<br>ugagguaguaguuugugcu | 655 |
| rno-miR-7b<br>uggaagacuugugauuuuguu | 656 |
| rno-miR-9<br>ucuuugguuaucuagcuguauga | 657 |
| rno-miR-10a<br>uacccuguagauccgaauuugug | 658 |
| rno-miR-10b<br>uacccuguagaaccgaauuugu | 659 |
| rno-miR-15b<br>uagcagcacaucauggu uuaca | 660 |
| rno-miR-16<br>uagcagcacguaaauauuggcg | 661 |
| rno-miR-17<br>caaagugcuuacagugcagguagu | 662 |
| rno-miR-18<br>uaaggugcaucuagugcagaua | 663 |
| rno-miR-19b<br>ugugcaaauccaugcaaaacuga | 664 |
| rno-miR-19a<br>ugugcaaaucuaugcaaaacuga | 665 |
| rno-miR-21<br>uagcuuaucagacugauguuga | 666 |
| rno-miR-22<br>aagcugccaguugaagaacugu | 667 |
| rno-miR-23a<br>aucacauugccagggauuucc | 668 |

TABLE 9-continued

| | SEQ ID NO: |
|---|---|
| rno-miR-23b<br>aucacauugccagggauuaccac | 669 |
| rno-miR-24<br>uggcucaguucagcaggaacag | 670 |
| rno-miR-25<br>cauugcacuugucucggucuga | 671 |
| rno-miR-26a<br>uucaaguaauccaggauaggcu | 672 |
| rno-miR-26b<br>uucaaguaauucaggauagguu | 673 |
| rno-miR-27b<br>uucacaguggcuaaguucug | 674 |
| rno-miR-27a<br>uucacaguggcuaaguuccgc | 675 |
| rno-miR-28<br>aaggagcucacagucuauugag | 676 |
| rno-miR-29b<br>uagcaccauuugaaaucagugu | 677 |
| rno-miR-29a<br>cuagcaccaucugaaaucgguu | 678 |
| rno-miR-29c<br>uagcaccauuugaaaucgguua | 679 |
| rno-miR-30c<br>uguaaacauccuacacucucagc | 680 |
| rno-miR-30e<br>uguaaacauccuugacugga | 681 |
| rno-miR-30b<br>uguaaacauccuacacucagc | 682 |
| rno-miR-30d<br>uguaaacauccccgacuggaag | 683 |
| rno-miR-30a<br>cuuucagucggauguuugcagc | 684 |
| rno-miR-31<br>aggcaagaugcuggcauagcug | 685 |
| rno-miR-32<br>uauugcacauuacuaaguugc | 686 |
| rno-miR-33<br>gugcauuguaguugcauug | 687 |
| rno-miR-34b<br>uaggcaguguaauuagcugauug | 688 |
| rno-miR-34c<br>aggcaguguaguuagcugauugc | 689 |
| rno-miR-34a<br>uggcagugucuuagcugguuguu | 690 |
| rno-miR-92<br>uauugcacuugucccggccug | 691 |
| rno-miR-93<br>caaagugcuguucgugcagguag | 692 |
| rno-miR-96<br>uuuggcacuagcacauuuuugcu | 693 |
| rno-miR-98<br>ugagguaguaaguuguauuguu | 694 |

TABLE 9-continued

| | SEQ ID NO: |
|---|---|
| rno-miR-99a<br>aacccguagauccgaucuugug | 695 |
| rno-miR-99b<br>cacccguagaaccgaccuugcg | 696 |
| rno-miR-100<br>aacccguagauccgaacuugug | 697 |
| rno-miR-101<br>uacaguacugugauaacugaag | 698 |
| rno-miR-103<br>agcagcauuguacagggcuauga | 699 |
| rno-miR-106b<br>uaaagugcugacagugcagau | 700 |
| rno-miR-107<br>agcagcauuguacagggcuauca | 701 |
| rno-miR-122a<br>uggagugugacaaugguguuugu | 702 |
| rno-miR-124a<br>uuaaggcacgcggugaaugcca | 703 |
| rno-miR-125a<br>ucccugagacccuuuaaccugug | 704 |
| rno-miR-125b<br>ucccugagacccuaacuuguga | 705 |
| rno-miR-126*<br>cauuauuacuuuugguacgcg | 706 |
| rno-miR-126<br>ucguaccgugaguaauaaugc | 707 |
| rno-miR-127<br>ucggauccgucugagcuuggcu | 708 |
| rno-miR-128a<br>ucacagugaaccggucucuuuu | 709 |
| rno-miR-128b<br>ucacagugaaccggucucuuuc | 710 |
| rno-miR-130a<br>cagugcaauguuaaaagggc | 711 |
| rno-miR-130b<br>cagugcaaugaugaaagggcau | 712 |
| rno-miR-132<br>uaacagucuacagccauggucg | 713 |
| rno-miR-133a<br>uuggucccuucaaccagcugu | 714 |
| rno-miR-134<br>ugugacugguugaccagaggg | 715 |
| rno-miR-135a<br>uauggcuuuuuauuccuauguga | 716 |
| rno-miR-136<br>acuccauuuguuuugaugaugga | 717 |
| rno-miR-137<br>uauugcuuaagaauacgcguag | 718 |
| rno-miR-138<br>agcuggguguugugaauc | 719 |

TABLE 9-continued

| | SEQ ID NO: |
|---|---|
| rno-miR-139 ucuacagugcacgugucu | 720 |
| rno-miR-141 aacacugucugguaaagaugg | 721 |
| rno-miR-142-5p cauaaaguagaaagcacuac | 722 |
| rno-miR-142-3p uguaguguuuccuacuuuaugga | 723 |
| rno-miR-143 ugagaugaagcacuguagcuca | 724 |
| rno-miR-144 uacaguauagaugauguacuag | 725 |
| rno-miR-145 guccaguuuucccaggaaucccuu | 726 |
| rno-miR-146 ugagaacugaauuccauggguu | 727 |
| rno-miR-150 ucucccaacccuuguaccagug | 728 |
| rno-miR-152 ucagugcaugacagaacuugg | 729 |
| rno-miR-153 uugcauagucacaaaguga | 730 |
| rno-miR-154 uagguuauccguguugccuucg | 731 |
| rno-miR-181c aacauucaaccugucggugagu | 732 |
| rno-miR-181a aacauucaacgcugucggugagu | 733 |
| rno-miR-181b aacauucauugcugucgguggguu | 734 |
| rno-miR-183 uauggcacugguagaauucacug | 735 |
| rno-miR-184 uggacggagaacugauaagggu | 736 |
| rno-miR-185 uggagagaaaggcaguuc | 737 |
| rno-miR-186 caaagaauucuccuuuugggcuu | 738 |
| rno-miR-187 ucgugucuuguguugcagccg | 739 |
| rno-miR-190 ugauauguuugauauauuaggu | 740 |
| rno-miR-191 caacggaaucccaaaagcagcu | 741 |
| rno-miR-192 cugaccuaugaauugacagcc | 742 |
| rno-miR-193 aacuggccuacaaaguccag | 743 |
| rno-miR-194 uguaacagcaacuccauggga | 744 |

TABLE 9-continued

| | SEQ ID NO: |
|---|---|
| rno-miR-195 uagcagcacagaaauauuggc | 745 |
| rno-miR-196 uagguaguuucauguuguugg | 746 |
| rno-miR-199a cccaguguucagacuaccuguuc | 747 |
| rno-miR-200c aauacugccggguaaugaugga | 748 |
| rno-miR-200a uaacacugucugguaacgaugu | 749 |
| rno-miR-200b cucuaauacugccugguaaugaug | 750 |
| rno-miR-203 gugaaauguuuaggaccacuag | 751 |
| rno-miR-204 uucccuuugucauccuaugccu | 752 |
| rno-miR-205 uccuucauuccaccggagucug | 753 |
| rno-miR-206 uggaauguaaggaagugugugg | 754 |
| rno-miR-208 auaagacgagcaaaaagcuugu | 755 |
| rno-miR-210 cugugcgugugacagcggcug | 756 |
| rno-miR-211 uucccuuugucauccuuugccu | 757 |
| rno-miR-212 uaacagucuccagucacggcc | 758 |
| rno-miR-213 accaucgaccguugauuguacc | 759 |
| rno-miR-214 acagcaggcacagacaggcag | 760 |
| rno-miR-216 uaaucucagcuggcaacugug | 761 |
| rno-miR-217 uacugcaucaggaacugacuggau | 762 |
| rno-miR-218 uugugcuugaucuaaccaugu | 763 |
| rno-miR-219 ugauuguccaaacgcaauucu | 764 |
| rno-miR-221 agcuacauugucugcuggguuuc | 765 |
| rno-miR-222 agcuacaucuggcuacugggucuc | 766 |
| rno-miR-223 ugucaguuugucaaauacccc | 767 |
| rno-miR-290 cucaaacuauggggcacuuuuu | 768 |
| rno-miR-291-5p caucaaaguggaggcccucucu | 769 |
| rno-miR-291-3p aaagugcuuccacuuugugugcc | 770 |

TABLE 9-continued

| | SEQ ID NO: |
|---|---|
| rno-miR-292-5p acucaaacuggggcucuuuug | 771 |
| rno-miR-292-3p aagugccgccagguuuugagugu | 772 |
| rno-miR-296 agggccccccucaauccugu | 773 |
| rno-miR-297 auguaugugugcauguaugcaug | 774 |
| rno-miR-298 ggcagaggagggcuguucuucc | 775 |
| rno-miR-299 ugguuuaccgucccacauacau | 776 |

TABLE 9-continued

| | SEQ ID NO: |
|---|---|
| rno-miR-300 uaugcaagggcaagcucucuuc | 777 |
| rno-miR-320 aaaagcuggguugagagggcgaa | 778 |
| rno-miR-321 uaagccagggauguggguuc | 779 |

Although the disclosed teachings have been described with reference to various applications, methods, kits, and compositions, it will be appreciated that various changes and modifications may be made without departing from the teachings herein. The foregoing examples are provided to better illustrate the disclosed teachings and are not intended to limit the scope of the teachings herein.

We claim:

1. A composition comprising:
   (a) a nucleic acid sample;
   (b) a reverse transcriptase;
   (c) an unlabeled linker probe comprising a 3'target-specific portion, a stem, and a loop;
   (d) at least one primer; and
   (e) a detector probe, wherein at least a portion of said detector probe corresponds with said stem of said linker probe, wherein said detector probe is a different molecule from said linker probe and wherein said detector probe comprises a detectable label.

2. The composition of claim 1, wherein said nucleic acid sample is an RNA sample.

3. The composition of claim 1, further comprising at least one dNTP.

4. The composition of claim 3, wherein said dNTP is a dUTP.

5. The composition of claim 1, wherein said linker probe is designed to hybridize to a target polynucleotide of interest and can extend to form a reaction product that includes the stem.

6. The composition of claim 5, wherein the target polynucleotide of interest is a miRNA.

7. The composition of claim 1, wherein said linker probe further comprises an identifying portion.

8. The composition of claim 1, further comprising a DNA polymerase.

9. The composition of claim 6, wherein the composition comprises a forward primer specific for a miRNA and a universal reverse primer.

10. The composition of claim 9, wherein the universal reverse primer comprises a nucleotide of the loop of the linker probe.

11. The composition of claim 10, wherein the nucleic acid sample is a cell lysate.

12. The composition of claim 6, wherein the 3' target-specific portion is designed to hybridize to the 3' end region of the miRNA.

13. The composition of claim 1, wherein the loop comprises 14-18 nucleotides.

14. The composition of claim 1, wherein the 3' target specific portion comprises 5-8 nucleotides.

15. The composition of claim 1, wherein the detector probe comprises a universal base, a peptide nucleic acid (PNA), and/or a locked nucleic acid (LNA).

16. The composition of claim 1, wherein the detector probe comprises VIC or FAM.

17. The composition of claim 1, wherein the detector probe is a 5'-nuclease cleavable probe.

18. The composition of claim 1, wherein the target polynucleotide of interest is 18-25 nucleotides in length.

* * * * *

SEQUENCE LISTING

```
<160> NUMBER OF SEQ ID NOS: 783

<210> SEQ ID NO 1
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1
uagcagcacg uaaauauugg cg                                             22

<210> SEQ ID NO 2
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2
uaaagugcuu auagugcagg ua                                             22

<210> SEQ ID NO 3
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 3
uagcuuauca gacugauguu ga                                             22

<210> SEQ ID NO 4
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
aagcugccag uugaagaacu gu                                             22
```

<210> SEQ ID NO 5
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
uucaaguaau ccaggauagg cu                                              22

<210> SEQ ID NO 6
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
cuagcaccau cugaaaucgg uu                                              22

<210> SEQ ID NO 7
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
cuuucagucg gauguuugca gc                                              22

<210> SEQ ID NO 8
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
uggcaguguc uuagcugguu gu                                              22

<210> SEQ ID NO 9
<211> LENGTH: 24
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 9
cucuaauacu gccugguaau gaug                                            24

<210> SEQ ID NO 10
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 10
gcacauuaca cggucgaccu cu                                              22

```
<210> SEQ ID NO 11
<211> LENGTH: 23
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 11 cgcaucccu agggcauugg ugu                                            23

<210> SEQ ID NO 12
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 12
ugagguagua gguuguauag uu                                            22

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 13
gtcgtatcca gtgcagggtc cgaggtattc gcactggata cgaccgccaa              50

<210> SEQ ID NO 14
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 14
gtcgtatcca gtgcagggtc cgaggtattc gcactggata cgactacctg              50

<210> SEQ ID NO 15
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
gtcgtatcca gtgcagggtc cgaggtattc gcactggata cgactcaaca              50

<210> SEQ ID NO 16
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 16
gtcgtatcca gtgcagggtc cgaggtattc gcactggata cgacacagtt              50
```

```
<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 17
gtcgtatcca gtgcagggtc cgaggtattc gcactggata cgacagccta           50

<210> SEQ ID NO 18
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
gtcgtatcca gtgcagggtc cgaggtattc gcactggata cgacaaccga           50

<210> SEQ ID NO 19
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 19
gtcgtatcca gtgcagggtc cgaggtattc gcactggata cgacgctgca           50

<210> SEQ ID NO 20
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 20
gtcgtatcca gtgcagggtc cgaggtattc gcactggata cgacacaacc           50

<210> SEQ ID NO 21
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 21
gtcgtatcca gtgcagggtc cgaggtattc gcactggata cgaccatcat           50

<210> SEQ ID NO 22
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 22
gtcgtatcca gtgcagggtc cgaggtattc gcactggata cgacagaggt           50

<210> SEQ ID NO 23
```

```
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 23
gtcgtatcca gtgcagggtc cgaggtattc gcactggata cgacacacca                50

<210> SEQ ID NO 24
<211> LENGTH: 50
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 24
gtcgtatcca gtgcagggtc cgaggtattc gcactggata cgacaactat                50

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgcgctagca gcacgtaaat                                                 20

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gccgctaaag tgcttatagt gc                                              22

<210> SEQ ID NO 27
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcccgctagc ttatcagact gatg                                            24

<210> SEQ ID NO 28
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcctgaagct gccagttga                                                  19

<210> SEQ ID NO 29
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccggcgttca agtaatccag ga                                              22

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
gccgctagca ccatctgaaa                                                 20

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
gcccctttca gtcggatgtt t                                               21

<210> SEQ ID NO 32
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gcccgtggca gtgtcttag                                                  19

<210> SEQ ID NO 33
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gcccctctaa tactgcctgg                                                 20

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
gccacgcaca ttacacggtc                                                 20

<210> SEQ ID NO 35
<211> LENGTH: 18
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 35
gccaccatcc cctagggc                                                 18

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gccgctgagg tagtaggttg t                                             21

<210> SEQ ID NO 37
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 37
atacgaccgc caatat                                                   16

<210> SEQ ID NO 38
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 38
ctggatacga ctacctg                                                  17

<210> SEQ ID NO 39
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 39
ctggatacga ctcaaca                                                  17

<210> SEQ ID NO 40
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 40
tggatacgac acagttct                                                 18

<210> SEQ ID NO 41
<211> LENGTH: 18
<212> TYPE: DNA
<213> ORGANISM: Artificial Sequence
```

```
<220> FEATURE:
<223> OTHER INFORMATION: Description of Artificial Sequence: Synthetic
      probe

<400> SEQUENCE: 41
tggatacgac agcctatc                                                        18

<210> SEQ ID NO 42
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 42
tggatacgac aaccgat                                                         17

<210> SEQ ID NO 43
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 43
ctggatacga cgctgc                                                          16

<210> SEQ ID NO 44
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 44
atacgacaca accagc                                                          16

<210> SEQ ID NO 45
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 45
atacgaccat cattacc                                                         17

<210> SEQ ID NO 46
<211> LENGTH: 17
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 46
ctggatacga cagaggt                                                         17

<210> SEQ ID NO 47
<211> LENGTH: 17
<212> TYPE: DNA
<213> ORGANISM: Artificial Sequence
<220> FEATURE:
```

```
<223> OTHER INFORMATION: Description of Artificial Sequence: Synthetic
      probe

<400> SEQUENCE: 47
atacgacaca ccaatgc                                                    17

<210> SEQ ID NO 48
<211> LENGTH: 18
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 48
tggatacgac aactatac                                                   18

<210> SEQ ID NO 49
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
gtgcagggtc cgaggt                                                     16

<210> SEQ ID NO 50
<211> LENGTH: 22
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 50
ugagguagua gguuguauag uu                                              22

<210> SEQ ID NO 51
<211> LENGTH: 74
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 51
gggugaggua guagguugua aguuuggggg cucugcccug cuaugggaua acuauacaau      60
cuacugucuu uccu                                                       74

<210> SEQ ID NO 52
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 52
uucaaguaau ucaggauagg u                                               21

<210> SEQ ID NO 53
<211> LENGTH: 77
<212> TYPE: RNA
<213> ORGANISM: Artificial Sequence
```

```
<220> FEATURE:
<223> OTHER INFORMATION: Description of Artificial Sequence: Synthetic
      oligonucleotide

<400> SEQUENCE: 53
ccgggaccca guucaaguaa uucaggauag guugugugcu guccagccug uucuccauua    60
cuuggcucgg ggaccgg                                                   77

<210> SEQ ID NO 54
<211> LENGTH: 22
<212> TYPE: RNA
<213> ORGANISM: Caenorhabditis elegans

<400> SEQUENCE: 54
ugagguagua gguuguauag uu                                             22

<210> SEQ ID NO 55
<211> LENGTH: 21
<212> TYPE: RNA
<213> ORGANISM: Caenorhabditis elegans

<400> SEQUENCE: 55
ucccugagac cucaagugug a                                              21

<210> SEQ ID NO 56
<211> LENGTH: 21
<212> TYPE: RNA
<213> ORGANISM: Caenorhabditis elegans

<400> SEQUENCE: 56
uggaauguaa agaaguaugu a                                              21

<210> SEQ ID NO 57
<211> LENGTH: 23
<212> TYPE: RNA
<213> ORGANISM: Caenorhabditis elegans

<400> SEQUENCE: 57
uaucacagcc agcuuugaug ugc                                            23

<210> SEQ ID NO 58
<211> LENGTH: 22
<212> TYPE: RNA
<213> ORGANISM: Caenorhabditis elegans

<400> SEQUENCE: 58
aggcagugug guuagcuggu ug                                             22

<210> SEQ ID NO 59
<211> LENGTH: 22
<212> TYPE: RNA
<213> ORGANISM: Caenorhabditis elegans

<400> SEQUENCE: 59
ucaccggaug gaaacuagca gu                                             22

<210> SEQ ID NO 60
<211> LENGTH: 22
<212> TYPE: RNA
<213> ORGANISM: Caenorhabditis elegans

<400> SEQUENCE: 60
ucaccgggug aaaauucgca ug                                             22
```

<210> SEQ ID NO 61
<211> LENGTH: 22
<212> TYPE: RNA
<213> ORGANISM: Caenorhabditis elegans

<400> SEQUENCE: 61
ucaccgggug aacacuugca gu                                        22

<210> SEQ ID NO 62
<211> LENGTH: 22
<212> TYPE: RNA
<213> ORGANISM: Caenorhabditis elegans

<400> SEQUENCE: 62
ucaccgggag aaaaacugga gu                                        22

<210> SEQ ID NO 63
<211> LENGTH: 22
<212> TYPE: RNA
<213> ORGANISM: Caenorhabditis elegans

<400> SEQUENCE: 63
ucaccgggug uaaaucagcu ug                                        22

<210> SEQ ID NO 64
<211> LENGTH: 22
<212> TYPE: RNA
<213> ORGANISM: Caenorhabditis elegans

<400> SEQUENCE: 64
ucaccgggug uacaucagcu aa                                        22

<210> SEQ ID NO 65
<211> LENGTH: 22
<212> TYPE: RNA
<213> ORGANISM: Caenorhabditis elegans

<400> SEQUENCE: 65
ucaccgggug aaaaaucacc ua                                        22

<210> SEQ ID NO 66
<211> LENGTH: 20
<212> TYPE: RNA
<213> ORGANISM: Caenorhabditis elegans

<400> SEQUENCE: 66
caccggguua acaucuacag                                           20

<210> SEQ ID NO 67
<211> LENGTH: 23
<212> TYPE: RNA
<213> ORGANISM: Caenorhabditis elegans

<400> SEQUENCE: 67
uaucacaguu uacuugcugu cgc                                       23

<210> SEQ ID NO 68
<211> LENGTH: 21
<212> TYPE: RNA
<213> ORGANISM: Caenorhabditis elegans

<400> SEQUENCE: 68
ugacuagaga cacauucagc u          21

<210> SEQ ID NO 69
<211> LENGTH: 21
<212> TYPE: RNA
<213> ORGANISM: Caenorhabditis elegans

<400> SEQUENCE: 69
ugacuagaga cacauucagc u          21

<210> SEQ ID NO 70
<211> LENGTH: 22
<212> TYPE: RNA
<213> ORGANISM: Caenorhabditis elegans

<400> SEQUENCE: 70
ugucauggag ucgcucucuu ca          22

<210> SEQ ID NO 71
<211> LENGTH: 22
<212> TYPE: RNA
<213> ORGANISM: Caenorhabditis elegans

<400> SEQUENCE: 71
ugucauggag gcgcucucuu ca          22

<210> SEQ ID NO 72
<211> LENGTH: 23
<212> TYPE: RNA
<213> ORGANISM: Caenorhabditis elegans

<400> SEQUENCE: 72
ugagguaggc ucaguagaug cga          23

<210> SEQ ID NO 73
<211> LENGTH: 22
<212> TYPE: RNA
<213> ORGANISM: Caenorhabditis elegans

<400> SEQUENCE: 73
aagcaccacg agaagcugca ga          22

<210> SEQ ID NO 74
<211> LENGTH: 24
<212> TYPE: RNA
<213> ORGANISM: Caenorhabditis elegans

<400> SEQUENCE: 74
ugauaugucu gguauucuug gguu          24

<210> SEQ ID NO 75
<211> LENGTH: 23
<212> TYPE: RNA
<213> ORGANISM: Caenorhabditis elegans

<400> SEQUENCE: 75
uacccguagc uccuauccau guu          23

<210> SEQ ID NO 76
<211> LENGTH: 24
<212> TYPE: RNA
<213> ORGANISM: Caenorhabditis elegans

<400> SEQUENCE: 76
cacccguaca uauguuuccg ugcu                                           24

<210> SEQ ID NO 77
<211> LENGTH: 24
<212> TYPE: RNA
<213> ORGANISM: Caenorhabditis elegans

<400> SEQUENCE: 77
cacccguaca uuuguuuccg ugcu                                           24

<210> SEQ ID NO 78
<211> LENGTH: 24
<212> TYPE: RNA
<213> ORGANISM: Caenorhabditis elegans

<400> SEQUENCE: 78
uacccguaau cuucauaauc cgag                                           24

<210> SEQ ID NO 79
<211> LENGTH: 23
<212> TYPE: RNA
<213> ORGANISM: Caenorhabditis elegans

<400> SEQUENCE: 79
uacccguaua aguuucugcu gag                                            23

<210> SEQ ID NO 80
<211> LENGTH: 23
<212> TYPE: RNA
<213> ORGANISM: Caenorhabditis elegans

<400> SEQUENCE: 80
uggcggaucc auuuuggguu gua                                            23

<210> SEQ ID NO 81
<211> LENGTH: 22
<212> TYPE: RNA
<213> ORGANISM: Caenorhabditis elegans

<400> SEQUENCE: 81
uacccguaau guuuccgcug ag                                             22

<210> SEQ ID NO 82
<211> LENGTH: 24
<212> TYPE: RNA
<213> ORGANISM: Caenorhabditis elegans

<400> SEQUENCE: 82
uacccuguag aucgagcugu gugu                                           24

<210> SEQ ID NO 83
<211> LENGTH: 22
<212> TYPE: RNA
<213> ORGANISM: Caenorhabditis elegans

<400> SEQUENCE: 83
ugagaucguu caguacggca au                                             22

<210> SEQ ID NO 84
<211> LENGTH: 23
<212> TYPE: RNA
<213> ORGANISM: Caenorhabditis elegans

```
<400> SEQUENCE: 84
ucgaaucguu uaucaggaug aug                                              23

<210> SEQ ID NO 85
<211> LENGTH: 23
<212> TYPE: RNA
<213> ORGANISM: Caenorhabditis elegans

<400> SEQUENCE: 85
uauuaugcac auuuucuagu uca                                              23

<210> SEQ ID NO 86
<211> LENGTH: 23
<212> TYPE: RNA
<213> ORGANISM: Caenorhabditis elegans

<400> SEQUENCE: 86
ugacuagaac cguuacucau cuc                                              23

<210> SEQ ID NO 87
<211> LENGTH: 22
<212> TYPE: RNA
<213> ORGANISM: Caenorhabditis elegans

<400> SEQUENCE: 87
ugauauguaa ucuagcuuac ag                                               22

<210> SEQ ID NO 88
<211> LENGTH: 24
<212> TYPE: RNA
<213> ORGANISM: Caenorhabditis elegans

<400> SEQUENCE: 88
uaugacacug aagcgaguug gaaa                                             24

<210> SEQ ID NO 89
<211> LENGTH: 23
<212> TYPE: RNA
<213> ORGANISM: Caenorhabditis elegans

<400> SEQUENCE: 89
uaugacacug aagcguuacc gaa                                              23

<210> SEQ ID NO 90
<211> LENGTH: 23
<212> TYPE: RNA
<213> ORGANISM: Caenorhabditis elegans

<400> SEQUENCE: 90
uaugacacug aagcguaacc gaa                                              23

<210> SEQ ID NO 91
<211> LENGTH: 23
<212> TYPE: RNA
<213> ORGANISM: Caenorhabditis elegans

<400> SEQUENCE: 91
caugacacug auuagggaug uga                                              23

<210> SEQ ID NO 92
<211> LENGTH: 24
<212> TYPE: RNA
<213> ORGANISM: Caenorhabditis elegans
```

-continued

<400> SEQUENCE: 92
ucacaaccuc cuagaaagag uaga                                                24

<210> SEQ ID NO 93
<211> LENGTH: 21
<212> TYPE: RNA
<213> ORGANISM: Caenorhabditis elegans

<400> SEQUENCE: 93
ucgaagacuc aaaaguguag a                                                  21

<210> SEQ ID NO 94
<211> LENGTH: 21
<212> TYPE: RNA
<213> ORGANISM: Caenorhabditis elegans

<400> SEQUENCE: 94
ucgaaaauua aaaguguag a                                                   21

<210> SEQ ID NO 95
<211> LENGTH: 23
<212> TYPE: RNA
<213> ORGANISM: Caenorhabditis elegans

<400> SEQUENCE: 95
uaauacgucg uugguguuuc cau                                                23

<210> SEQ ID NO 96
<211> LENGTH: 19
<212> TYPE: RNA
<213> ORGANISM: Caenorhabditis elegans

<400> SEQUENCE: 96
ugaaagacau ggguaguga                                                     19

<210> SEQ ID NO 97
<211> LENGTH: 20
<212> TYPE: RNA
<213> ORGANISM: Caenorhabditis elegans

<400> SEQUENCE: 97
aggcaagaug uuggcauagc                                                    20

<210> SEQ ID NO 98
<211> LENGTH: 23
<212> TYPE: RNA
<213> ORGANISM: Caenorhabditis elegans

<400> SEQUENCE: 98
uggcaagaug uaggcaguuc agu                                                23

<210> SEQ ID NO 99
<211> LENGTH: 22
<212> TYPE: RNA
<213> ORGANISM: Caenorhabditis elegans

<400> SEQUENCE: 99
uggcaagaaa uggcagucua ca                                                 22

<210> SEQ ID NO 100
<211> LENGTH: 22
<212> TYPE: RNA

<213> ORGANISM: Caenorhabditis elegans

<400> SEQUENCE: 100
uuaaagcuac caaccggcuu ca                                    22

<210> SEQ ID NO 101
<211> LENGTH: 22
<212> TYPE: RNA
<213> ORGANISM: Caenorhabditis elegans

<400> SEQUENCE: 101
uucguuguug augaagccuu ga                                    22

<210> SEQ ID NO 102
<211> LENGTH: 22
<212> TYPE: RNA
<213> ORGANISM: Caenorhabditis elegans

<400> SEQUENCE: 102
uucaucaggc cauagcuguc ca                                    22

<210> SEQ ID NO 103
<211> LENGTH: 21
<212> TYPE: RNA
<213> ORGANISM: Caenorhabditis elegans

<400> SEQUENCE: 103
uggaggccug guuguuugug c                                     21

<210> SEQ ID NO 104
<211> LENGTH: 22
<212> TYPE: RNA
<213> ORGANISM: Caenorhabditis elegans

<400> SEQUENCE: 104
auaaagcuag guuaccaaag cu                                    22

<210> SEQ ID NO 105
<211> LENGTH: 22
<212> TYPE: RNA
<213> ORGANISM: Caenorhabditis elegans

<400> SEQUENCE: 105
agcuuucgac augauucuga ac                                    22

<210> SEQ ID NO 106
<211> LENGTH: 23
<212> TYPE: RNA
<213> ORGANISM: Caenorhabditis elegans

<400> SEQUENCE: 106
ugagaucauu aguugaaagc cga                                   23

<210> SEQ ID NO 107
<211> LENGTH: 22
<212> TYPE: RNA
<213> ORGANISM: Caenorhabditis elegans

<400> SEQUENCE: 107
ugagaucauc gugaaagcua gu                                    22

<210> SEQ ID NO 108
<211> LENGTH: 22

<212> TYPE: RNA
<213> ORGANISM: Caenorhabditis elegans

<400> SEQUENCE: 108
ugagaucauc gugaaagcca gu                                        22

<210> SEQ ID NO 109
<211> LENGTH: 22
<212> TYPE: RNA
<213> ORGANISM: Caenorhabditis elegans

<400> SEQUENCE: 109
uagcaccaua uaaauucagu aa                                        22

<210> SEQ ID NO 110
<211> LENGTH: 22
<212> TYPE: RNA
<213> ORGANISM: Caenorhabditis elegans

<400> SEQUENCE: 110
ugagguagua uguaauauug ua                                        22

<210> SEQ ID NO 111
<211> LENGTH: 24
<212> TYPE: RNA
<213> ORGANISM: Caenorhabditis elegans

<400> SEQUENCE: 111
uacaaaguau uugaaaaguc gugc                                      24

<210> SEQ ID NO 112
<211> LENGTH: 23
<212> TYPE: RNA
<213> ORGANISM: Caenorhabditis elegans

<400> SEQUENCE: 112
uaagugaaug cuuugccaca guc                                       23

<210> SEQ ID NO 113
<211> LENGTH: 20
<212> TYPE: RNA
<213> ORGANISM: Caenorhabditis elegans

<400> SEQUENCE: 113
gugagcaaag uuucaggugu                                           20

<210> SEQ ID NO 114
<211> LENGTH: 22
<212> TYPE: RNA
<213> ORGANISM: Caenorhabditis elegans

<400> SEQUENCE: 114
ugauauguug uuugaaugcc cc                                        22

<210> SEQ ID NO 115
<211> LENGTH: 21
<212> TYPE: RNA
<213> ORGANISM: Caenorhabditis elegans

<400> SEQUENCE: 115
uaaggcacgc ggugaaugcc a                                         21

<210> SEQ ID NO 116

```
<211> LENGTH: 23
<212> TYPE: RNA
<213> ORGANISM: Caenorhabditis elegans

<400> SEQUENCE: 116
aauggcacug caugaauuca cgg                                              23

<210> SEQ ID NO 117
<211> LENGTH: 27
<212> TYPE: RNA
<213> ORGANISM: Caenorhabditis elegans

<400> SEQUENCE: 117
aaugacacug guuaucuuuu ccaucgu                                          27

<210> SEQ ID NO 118
<211> LENGTH: 23
<212> TYPE: RNA
<213> ORGANISM: Caenorhabditis elegans

<400> SEQUENCE: 118
guauuaguug ugcgaccagg aga                                              23

<210> SEQ ID NO 119
<211> LENGTH: 24
<212> TYPE: RNA
<213> ORGANISM: Caenorhabditis elegans

<400> SEQUENCE: 119
uaagcucgug aucaacaggc agaa                                             24

<210> SEQ ID NO 120
<211> LENGTH: 23
<212> TYPE: RNA
<213> ORGANISM: Caenorhabditis elegans

<400> SEQUENCE: 120
uaaaugcauc uuaacugcgg uga                                              23

<210> SEQ ID NO 121
<211> LENGTH: 23
<212> TYPE: RNA
<213> ORGANISM: Caenorhabditis elegans

<400> SEQUENCE: 121
uugagcaaug cgcaugugcg gga                                              23

<210> SEQ ID NO 122
<211> LENGTH: 21
<212> TYPE: RNA
<213> ORGANISM: Caenorhabditis elegans

<400> SEQUENCE: 122
uuauugcucg agaauacccu u                                                21

<210> SEQ ID NO 123
<211> LENGTH: 22
<212> TYPE: RNA
<213> ORGANISM: Caenorhabditis elegans

<400> SEQUENCE: 123
uauugcacuc uccccggccu ga                                               22
```

```
<210> SEQ ID NO 124
<211> LENGTH: 23
<212> TYPE: RNA
<213> ORGANISM: Caenorhabditis elegans

<400> SEQUENCE: 124
uaauacuguc agguaaugac gcu                                           23

<210> SEQ ID NO 125
<211> LENGTH: 24
<212> TYPE: RNA
<213> ORGANISM: Caenorhabditis elegans

<400> SEQUENCE: 125
ucccugagaa uucucgaaca gcuu                                          24

<210> SEQ ID NO 126
<211> LENGTH: 23
<212> TYPE: RNA
<213> ORGANISM: Caenorhabditis elegans

<400> SEQUENCE: 126
uuuguacucc gaugccauuc aga                                           23

<210> SEQ ID NO 127
<211> LENGTH: 23
<212> TYPE: RNA
<213> ORGANISM: Caenorhabditis elegans

<400> SEQUENCE: 127
uuuguacuac acauagguac ugg                                           23

<210> SEQ ID NO 128
<211> LENGTH: 21
<212> TYPE: RNA
<213> ORGANISM: Caenorhabditis elegans

<400> SEQUENCE: 128
uuguacuaca caaaaguacu g                                             21

<210> SEQ ID NO 129
<211> LENGTH: 22
<212> TYPE: RNA
<213> ORGANISM: Caenorhabditis elegans

<400> SEQUENCE: 129
uacuggcccc caaaucuucg cu                                            22

<210> SEQ ID NO 130
<211> LENGTH: 21
<212> TYPE: RNA
<213> ORGANISM: Caenorhabditis elegans

<400> SEQUENCE: 130
ugagguaggu gcgagaaaug a                                             21

<210> SEQ ID NO 131
<211> LENGTH: 21
<212> TYPE: RNA
<213> ORGANISM: Caenorhabditis elegans

<400> SEQUENCE: 131
uugcguaggc cuuugcuucg a                                             21
```

```
<210> SEQ ID NO 132
<211> LENGTH: 23
<212> TYPE: RNA
<213> ORGANISM: Caenorhabditis elegans

<400> SEQUENCE: 132
cgguacgauc gcggcgggau auc                                            23

<210> SEQ ID NO 133
<211> LENGTH: 24
<212> TYPE: RNA
<213> ORGANISM: Caenorhabditis elegans

<400> SEQUENCE: 133
ucuuugguug uacaaagugg uaug                                           24

<210> SEQ ID NO 134
<211> LENGTH: 22
<212> TYPE: RNA
<213> ORGANISM: Caenorhabditis elegans

<400> SEQUENCE: 134
auuggucccc uccaaguagc uc                                             22

<210> SEQ ID NO 135
<211> LENGTH: 22
<212> TYPE: RNA
<213> ORGANISM: Caenorhabditis elegans

<400> SEQUENCE: 135
uuacauguuu cggguaggag cu                                             22

<210> SEQ ID NO 136
<211> LENGTH: 23
<212> TYPE: RNA
<213> ORGANISM: Caenorhabditis elegans

<400> SEQUENCE: 136
ugacuagagc cuauucucuu cuu                                            23

<210> SEQ ID NO 137
<211> LENGTH: 23
<212> TYPE: RNA
<213> ORGANISM: Caenorhabditis elegans

<400> SEQUENCE: 137
uacacgugca cggauaacgc uca                                            23

<210> SEQ ID NO 138
<211> LENGTH: 22
<212> TYPE: RNA
<213> ORGANISM: Caenorhabditis elegans

<400> SEQUENCE: 138
ucacaggacu uuugagcguu gc                                             22

<210> SEQ ID NO 139
<211> LENGTH: 22
<212> TYPE: RNA
<213> ORGANISM: Caenorhabditis elegans

<400> SEQUENCE: 139
ucacagucaa cuguuggcau gg                                             22
```

```
<210> SEQ ID NO 140
<211> LENGTH: 24
<212> TYPE: RNA
<213> ORGANISM: Caenorhabditis elegans

<400> SEQUENCE: 140
uuaaguagug gugccgcucu uauu                                              24

<210> SEQ ID NO 141
<211> LENGTH: 23
<212> TYPE: RNA
<213> ORGANISM: Caenorhabditis elegans

<400> SEQUENCE: 141
uaaguaguag ugccgcaggu aac                                               23

<210> SEQ ID NO 142
<211> LENGTH: 21
<212> TYPE: RNA
<213> ORGANISM: Caenorhabditis elegans

<400> SEQUENCE: 142
cacaccucac uaacacugac c                                                 21

<210> SEQ ID NO 143
<211> LENGTH: 23
<212> TYPE: RNA
<213> ORGANISM: Caenorhabditis elegans

<400> SEQUENCE: 143
ugcaaaucuu ucgcgacugu agg                                               23

<210> SEQ ID NO 144
<211> LENGTH: 21
<212> TYPE: RNA
<213> ORGANISM: Caenorhabditis elegans

<400> SEQUENCE: 144
uggaaugcau agaagacugu a                                                 21

<210> SEQ ID NO 145
<211> LENGTH: 22
<212> TYPE: RNA
<213> ORGANISM: Caenorhabditis elegans

<400> SEQUENCE: 145
gaguaucagg aguacccagu ga                                                22

<210> SEQ ID NO 146
<211> LENGTH: 21
<212> TYPE: RNA
<213> ORGANISM: Caenorhabditis elegans

<400> SEQUENCE: 146
gguuuugaga ggaauccuuu u                                                 21

<210> SEQ ID NO 147
<211> LENGTH: 21
<212> TYPE: RNA
<213> ORGANISM: Caenorhabditis elegans

<400> SEQUENCE: 147
```

```
aaaucucauc cuaaucuggu a                                              21

<210> SEQ ID NO 148
<211> LENGTH: 20
<212> TYPE: RNA
<213> ORGANISM: Caenorhabditis elegans

<400> SEQUENCE: 148
gugaugucga acucuuguag                                                20

<210> SEQ ID NO 149
<211> LENGTH: 19
<212> TYPE: RNA
<213> ORGANISM: Caenorhabditis elegans

<400> SEQUENCE: 149
uagcuuuuua guuuucacg                                                 19

<210> SEQ ID NO 150
<211> LENGTH: 20
<212> TYPE: RNA
<213> ORGANISM: Caenorhabditis elegans

<400> SEQUENCE: 150
guuucucgau guuuucugau                                                20

<210> SEQ ID NO 151
<211> LENGTH: 20
<212> TYPE: RNA
<213> ORGANISM: Caenorhabditis elegans

<400> SEQUENCE: 151
ggcggguggu uguuguuaug                                                20

<210> SEQ ID NO 152
<211> LENGTH: 20
<212> TYPE: RNA
<213> ORGANISM: Caenorhabditis elegans

<400> SEQUENCE: 152
ugagggagga aggugguau                                                 20

<210> SEQ ID NO 153
<211> LENGTH: 20
<212> TYPE: RNA
<213> ORGANISM: Caenorhabditis elegans

<400> SEQUENCE: 153
aggcaagacu uuggcaaagc                                                20

<210> SEQ ID NO 154
<211> LENGTH: 20
<212> TYPE: RNA
<213> ORGANISM: Caenorhabditis elegans

<400> SEQUENCE: 154
cccgugaagu gucugcugca                                                20

<210> SEQ ID NO 155
<211> LENGTH: 24
<212> TYPE: RNA
<213> ORGANISM: Caenorhabditis elegans

<400> SEQUENCE: 155
```
ggcaagaauu agaagcaguu uggu                                          24

<210> SEQ ID NO 156
<211> LENGTH: 20
<212> TYPE: RNA
<213> ORGANISM: Caenorhabditis elegans

<400> SEQUENCE: 156
ggcaagacuc uggcaaaacu                                               20

<210> SEQ ID NO 157
<211> LENGTH: 20
<212> TYPE: RNA
<213> ORGANISM: Caenorhabditis elegans

<400> SEQUENCE: 157
ggcaugaugu agcaguggag                                               20

<210> SEQ ID NO 158
<211> LENGTH: 20
<212> TYPE: RNA
<213> ORGANISM: Caenorhabditis elegans

<400> SEQUENCE: 158
ucgccgggug ggaaagcauu                                               20

<210> SEQ ID NO 159
<211> LENGTH: 18
<212> TYPE: RNA
<213> ORGANISM: Caenorhabditis elegans

<400> SEQUENCE: 159
uguaggcaug gguguuug                                                 18

<210> SEQ ID NO 160
<211> LENGTH: 20
<212> TYPE: RNA
<213> ORGANISM: Caenorhabditis elegans

<400> SEQUENCE: 160
ugcccguacu gugucggcug                                               20

<210> SEQ ID NO 161
<211> LENGTH: 21
<212> TYPE: RNA
<213> ORGANISM: Caenorhabditis elegans

<400> SEQUENCE: 161
caauugccau guguugguau u                                             21

<210> SEQ ID NO 162
<211> LENGTH: 21
<212> TYPE: RNA
<213> ORGANISM: Caenorhabditis elegans

<400> SEQUENCE: 162
accuuguuug uugcugcucc u                                             21

<210> SEQ ID NO 163
<211> LENGTH: 21
<212> TYPE: RNA
<213> ORGANISM: Caenorhabditis elegans

```
<400> SEQUENCE: 163
uuuguuuuag ccugagcuau g                                            21

<210> SEQ ID NO 164
<211> LENGTH: 21
<212> TYPE: RNA
<213> ORGANISM: Caenorhabditis elegans

<400> SEQUENCE: 164
uugagcaacg cgaacaaauc a                                            21

<210> SEQ ID NO 165
<211> LENGTH: 21
<212> TYPE: RNA
<213> ORGANISM: Caenorhabditis elegans

<400> SEQUENCE: 165
uaaaugccag ucguugcagg a                                            21

<210> SEQ ID NO 166
<211> LENGTH: 21
<212> TYPE: RNA
<213> ORGANISM: Caenorhabditis elegans

<400> SEQUENCE: 166
caauugguau cccugucaag g                                            21

<210> SEQ ID NO 167
<211> LENGTH: 21
<212> TYPE: RNA
<213> ORGANISM: Caenorhabditis elegans

<400> SEQUENCE: 167
ucacuggucu uucucugacg a                                            21

<210> SEQ ID NO 168
<211> LENGTH: 21
<212> TYPE: RNA
<213> ORGANISM: Caenorhabditis elegans

<400> SEQUENCE: 168
ugaccguaau cccguucaca a                                            21

<210> SEQ ID NO 169
<211> LENGTH: 21
<212> TYPE: RNA
<213> ORGANISM: Caenorhabditis elegans

<400> SEQUENCE: 169
uuuuguauga gacgcauuuc g                                            21

<210> SEQ ID NO 170
<211> LENGTH: 22
<212> TYPE: RNA
<213> ORGANISM: Caenorhabditis elegans

<400> SEQUENCE: 170
uaucaucgau cacgugugau ga                                           22

<210> SEQ ID NO 171
<211> LENGTH: 22
<212> TYPE: RNA
<213> ORGANISM: Homo sapiens
```

```
<400> SEQUENCE: 171
ugagguagua gguuguauag uu                                          22

<210> SEQ ID NO 172
<211> LENGTH: 22
<212> TYPE: RNA
<213> ORGANISM: Homo sapiens

<400> SEQUENCE: 172
ugagguagua gguugugugg uu                                          22

<210> SEQ ID NO 173
<211> LENGTH: 22
<212> TYPE: RNA
<213> ORGANISM: Homo sapiens

<400> SEQUENCE: 173
ugagguagua gguuguaugg uu                                          22

<210> SEQ ID NO 174
<211> LENGTH: 21
<212> TYPE: RNA
<213> ORGANISM: Homo sapiens

<400> SEQUENCE: 174
agagguagua gguugcauag u                                           21

<210> SEQ ID NO 175
<211> LENGTH: 21
<212> TYPE: RNA
<213> ORGANISM: Homo sapiens

<400> SEQUENCE: 175
ugagguagga gguuguauag u                                           21

<210> SEQ ID NO 176
<211> LENGTH: 22
<212> TYPE: RNA
<213> ORGANISM: Homo sapiens

<400> SEQUENCE: 176
ugagguagua gauuguauag uu                                          22

<210> SEQ ID NO 177
<211> LENGTH: 22
<212> TYPE: RNA
<213> ORGANISM: Homo sapiens

<400> SEQUENCE: 177
uagcagcaca uaaugguuug ug                                          22

<210> SEQ ID NO 178
<211> LENGTH: 22
<212> TYPE: RNA
<213> ORGANISM: Homo sapiens

<400> SEQUENCE: 178
uagcagcacg uaaauauugg cg                                          22

<210> SEQ ID NO 179
<211> LENGTH: 24
<212> TYPE: RNA
```

```
<213> ORGANISM: Homo sapiens

<400> SEQUENCE: 179
caaagugcuu acagugcagg uagu                                          24

<210> SEQ ID NO 180
<211> LENGTH: 20
<212> TYPE: RNA
<213> ORGANISM: Homo sapiens

<400> SEQUENCE: 180
acugcaguga aggcacuugu                                               20

<210> SEQ ID NO 181
<211> LENGTH: 22
<212> TYPE: RNA
<213> ORGANISM: Homo sapiens

<400> SEQUENCE: 181
uaaggugcau cuagugcaga ua                                            22

<210> SEQ ID NO 182
<211> LENGTH: 23
<212> TYPE: RNA
<213> ORGANISM: Homo sapiens

<400> SEQUENCE: 182
ugugcaaauc uaugcaaaac uga                                           23

<210> SEQ ID NO 183
<211> LENGTH: 23
<212> TYPE: RNA
<213> ORGANISM: Homo sapiens

<400> SEQUENCE: 183
ugugcaaauc caugcaaaac uga                                           23

<210> SEQ ID NO 184
<211> LENGTH: 22
<212> TYPE: RNA
<213> ORGANISM: Homo sapiens

<400> SEQUENCE: 184
uaaagugcuu auagugcagg ua                                            22

<210> SEQ ID NO 185
<211> LENGTH: 22
<212> TYPE: RNA
<213> ORGANISM: Homo sapiens

<400> SEQUENCE: 185
uagcuuauca gacugauguu ga                                            22

<210> SEQ ID NO 186
<211> LENGTH: 22
<212> TYPE: RNA
<213> ORGANISM: Homo sapiens

<400> SEQUENCE: 186
aagcugccag uugaagaacu gu                                            22

<210> SEQ ID NO 187
<211> LENGTH: 21
```

<212> TYPE: RNA
<213> ORGANISM: Homo sapiens

<400> SEQUENCE: 187
aucacauugc cagggauuuc c                                              21

<210> SEQ ID NO 188
<211> LENGTH: 23
<212> TYPE: RNA
<213> ORGANISM: Homo sapiens

<400> SEQUENCE: 188
gugccuacug agcugauauc agu                                            23

<210> SEQ ID NO 189
<211> LENGTH: 22
<212> TYPE: RNA
<213> ORGANISM: Homo sapiens

<400> SEQUENCE: 189
uggcucaguu cagcaggaac ag                                             22

<210> SEQ ID NO 190
<211> LENGTH: 22
<212> TYPE: RNA
<213> ORGANISM: Homo sapiens

<400> SEQUENCE: 190
cauugcacuu gucucggucu ga                                             22

<210> SEQ ID NO 191
<211> LENGTH: 22
<212> TYPE: RNA
<213> ORGANISM: Homo sapiens

<400> SEQUENCE: 191
uucaaguaau ccaggauagg cu                                             22

<210> SEQ ID NO 192
<211> LENGTH: 21
<212> TYPE: RNA
<213> ORGANISM: Homo sapiens

<400> SEQUENCE: 192
uucaaguaau ucaggauagg u                                              21

<210> SEQ ID NO 193
<211> LENGTH: 22
<212> TYPE: RNA
<213> ORGANISM: Homo sapiens

<400> SEQUENCE: 193
uucacagugg cuaaguuccg cc                                             22

<210> SEQ ID NO 194
<211> LENGTH: 22
<212> TYPE: RNA
<213> ORGANISM: Homo sapiens

<400> SEQUENCE: 194
aaggagcuca cagucuauug ag                                             22

<210> SEQ ID NO 195

```
<211> LENGTH: 22
<212> TYPE: RNA
<213> ORGANISM: Homo sapiens

<400> SEQUENCE: 195
cuagcaccau cugaaaucgg uu                                             22

<210> SEQ ID NO 196
<211> LENGTH: 23
<212> TYPE: RNA
<213> ORGANISM: Homo sapiens

<400> SEQUENCE: 196
uguaaacauc cucgacugga agc                                            23

<210> SEQ ID NO 197
<211> LENGTH: 22
<212> TYPE: RNA
<213> ORGANISM: Homo sapiens

<400> SEQUENCE: 197
cuuucagucg gauguuugca gc                                             22

<210> SEQ ID NO 198
<211> LENGTH: 21
<212> TYPE: RNA
<213> ORGANISM: Homo sapiens

<400> SEQUENCE: 198
ggcaagaugc uggcauagcu g                                              21

<210> SEQ ID NO 199
<211> LENGTH: 21
<212> TYPE: RNA
<213> ORGANISM: Homo sapiens

<400> SEQUENCE: 199
uauugcacau uacuaaguug c                                              21

<210> SEQ ID NO 200
<211> LENGTH: 19
<212> TYPE: RNA
<213> ORGANISM: Homo sapiens

<400> SEQUENCE: 200
gugcauugua guugcauug                                                 19

<210> SEQ ID NO 201
<211> LENGTH: 22
<212> TYPE: RNA
<213> ORGANISM: Homo sapiens

<400> SEQUENCE: 201
uauugcacuu gucccggccu gu                                             22

<210> SEQ ID NO 202
<211> LENGTH: 22
<212> TYPE: RNA
<213> ORGANISM: Homo sapiens

<400> SEQUENCE: 202
aaagugcugu ucgugcaggu ag                                             22
```

```
<210> SEQ ID NO 203
<211> LENGTH: 22
<212> TYPE: RNA
<213> ORGANISM: Homo sapiens

<400> SEQUENCE: 203 uucaacggguu auuuauugag ca                                          22

<210> SEQ ID NO 204
<211> LENGTH: 22
<212> TYPE: RNA
<213> ORGANISM: Homo sapiens

<400> SEQUENCE: 204
uuuggcacua gcacauuuuu gc                                           22

<210> SEQ ID NO 205
<211> LENGTH: 22
<212> TYPE: RNA
<213> ORGANISM: Homo sapiens

<400> SEQUENCE: 205
ugagguagua aguuguauug uu                                           22

<210> SEQ ID NO 206
<211> LENGTH: 22
<212> TYPE: RNA
<213> ORGANISM: Homo sapiens

<400> SEQUENCE: 206
aacccguaga uccgaucuug ug                                           22

<210> SEQ ID NO 207
<211> LENGTH: 22
<212> TYPE: RNA
<213> ORGANISM: Homo sapiens

<400> SEQUENCE: 207
aacccguaga uccgaacuug ug                                           22

<210> SEQ ID NO 208
<211> LENGTH: 22
<212> TYPE: RNA
<213> ORGANISM: Homo sapiens

<400> SEQUENCE: 208
uacaguacug ugauaacuga ag                                           22

<210> SEQ ID NO 209
<211> LENGTH: 20
<212> TYPE: RNA
<213> ORGANISM: Homo sapiens

<400> SEQUENCE: 209
uagcaccauu ugaaaucagu                                              20

<210> SEQ ID NO 210
<211> LENGTH: 23
<212> TYPE: RNA
<213> ORGANISM: Homo sapiens

<400> SEQUENCE: 210
agcagcauug uacagggcua uga                                          23
```

<210> SEQ ID NO 211
<211> LENGTH: 20
<212> TYPE: RNA
<213> ORGANISM: Homo sapiens

<400> SEQUENCE: 211
ucaaaugcuc agacuccugu                                                    20

<210> SEQ ID NO 212
<211> LENGTH: 24
<212> TYPE: RNA
<213> ORGANISM: Homo sapiens

<400> SEQUENCE: 212
aaaagugcuu acagugcagg uagc                                               24

<210> SEQ ID NO 213
<211> LENGTH: 23
<212> TYPE: RNA
<213> ORGANISM: Homo sapiens

<400> SEQUENCE: 213
agcagcauug uacagggcua uca                                                23

<210> SEQ ID NO 214
<211> LENGTH: 21
<212> TYPE: RNA
<213> ORGANISM: Homo sapiens

<400> SEQUENCE: 214
cugaccuaug aauugacagc c                                                  21

<210> SEQ ID NO 215
<211> LENGTH: 21
<212> TYPE: RNA
<213> ORGANISM: Homo sapiens

<400> SEQUENCE: 215
uagguaguuu cauguuguug g                                                  21

<210> SEQ ID NO 216
<211> LENGTH: 22
<212> TYPE: RNA
<213> ORGANISM: Homo sapiens

<400> SEQUENCE: 216
uucaccaccu ucuccaccca gc                                                 22

<210> SEQ ID NO 217
<211> LENGTH: 19
<212> TYPE: RNA
<213> ORGANISM: Homo sapiens

<400> SEQUENCE: 217
gguccagagg ggagauagg                                                     19

<210> SEQ ID NO 218
<211> LENGTH: 23
<212> TYPE: RNA
<213> ORGANISM: Homo sapiens

<400> SEQUENCE: 218
cccaguguuc agacuaccug uuc                                                23

<210> SEQ ID NO 219
<211> LENGTH: 22
<212> TYPE: RNA
<213> ORGANISM: Homo sapiens

<400> SEQUENCE: 219
uacaguaguc ugcacauugg uu                                              22

<210> SEQ ID NO 220
<211> LENGTH: 22
<212> TYPE: RNA
<213> ORGANISM: Homo sapiens

<400> SEQUENCE: 220
auaagacgag caaaaagcuu gu                                              22

<210> SEQ ID NO 221
<211> LENGTH: 22
<212> TYPE: RNA
<213> ORGANISM: Homo sapiens

<400> SEQUENCE: 221
ucagugcacu acagaacuuu gu                                              22

<210> SEQ ID NO 222
<211> LENGTH: 23
<212> TYPE: RNA
<213> ORGANISM: Homo sapiens

<400> SEQUENCE: 222
uguaaacauc cuacacucuc agc                                             23

<210> SEQ ID NO 223
<211> LENGTH: 22
<212> TYPE: RNA
<213> ORGANISM: Homo sapiens

<400> SEQUENCE: 223
uguaaacauc cccgacugga ag                                              22

<210> SEQ ID NO 224
<211> LENGTH: 18
<212> TYPE: RNA
<213> ORGANISM: Homo sapiens

<400> SEQUENCE: 224
ucuacagugc acgugucu                                                   18

<210> SEQ ID NO 225
<211> LENGTH: 20
<212> TYPE: RNA
<213> ORGANISM: Homo sapiens

<400> SEQUENCE: 225
guguguggaa augcuucugc                                                 20

<210> SEQ ID NO 226
<211> LENGTH: 21
<212> TYPE: RNA
<213> ORGANISM: Homo sapiens

<400> SEQUENCE: 226

```
uggaagacua gugauuuugu u                                                21

<210> SEQ ID NO 227
<211> LENGTH: 23
<212> TYPE: RNA
<213> ORGANISM: Homo sapiens

<400> SEQUENCE: 227
uacccuguag auccgaauuu gug                                              23

<210> SEQ ID NO 228
<211> LENGTH: 22
<212> TYPE: RNA
<213> ORGANISM: Homo sapiens

<400> SEQUENCE: 228
uacccuguag aaccgaauuu gu                                               22

<210> SEQ ID NO 229
<211> LENGTH: 22
<212> TYPE: RNA
<213> ORGANISM: Homo sapiens

<400> SEQUENCE: 229
uggcaguguc uuagcugguu gu                                               22

<210> SEQ ID NO 230
<211> LENGTH: 23
<212> TYPE: RNA
<213> ORGANISM: Homo sapiens

<400> SEQUENCE: 230
aacauucaac gcugucggug agu                                              23

<210> SEQ ID NO 231
<211> LENGTH: 24
<212> TYPE: RNA
<213> ORGANISM: Homo sapiens

<400> SEQUENCE: 231
aacauucauu gcugucggug gguu                                             24

<210> SEQ ID NO 232
<211> LENGTH: 22
<212> TYPE: RNA
<213> ORGANISM: Homo sapiens

<400> SEQUENCE: 232
aacauucaac cugucgguga gu                                               22

<210> SEQ ID NO 233
<211> LENGTH: 22
<212> TYPE: RNA
<213> ORGANISM: Homo sapiens

<400> SEQUENCE: 233
uuuggcaaug guagaacuca ca                                               22

<210> SEQ ID NO 234
<211> LENGTH: 21
<212> TYPE: RNA
<213> ORGANISM: Homo sapiens

<400> SEQUENCE: 234
```

-continued ugguucuaga cuugccaacu a                                    21

<210> SEQ ID NO 235
<211> LENGTH: 23
<212> TYPE: RNA
<213> ORGANISM: Homo sapiens

<400> SEQUENCE: 235
uauggcacug guagaauuca cug                                  23

<210> SEQ ID NO 236
<211> LENGTH: 21
<212> TYPE: RNA
<213> ORGANISM: Homo sapiens

<400> SEQUENCE: 236
ucgugucuug uguugcagcc g                                    21

<210> SEQ ID NO 237
<211> LENGTH: 23
<212> TYPE: RNA
<213> ORGANISM: Homo sapiens

<400> SEQUENCE: 237
cccaguguuu agacuaucug uuc                                  23

<210> SEQ ID NO 238
<211> LENGTH: 22
<212> TYPE: RNA
<213> ORGANISM: Homo sapiens

<400> SEQUENCE: 238
gugaaauguu uaggaccacu ag                                   22

<210> SEQ ID NO 239
<211> LENGTH: 22
<212> TYPE: RNA
<213> ORGANISM: Homo sapiens

<400> SEQUENCE: 239
uucccuuugu cauccuaugc cu                                   22

<210> SEQ ID NO 240
<211> LENGTH: 22
<212> TYPE: RNA
<213> ORGANISM: Homo sapiens

<400> SEQUENCE: 240
uccuucauuc caccggaguc ug                                   22

<210> SEQ ID NO 241
<211> LENGTH: 21
<212> TYPE: RNA
<213> ORGANISM: Homo sapiens

<400> SEQUENCE: 241
cugugcgugu gacagcggcu g                                    21

<210> SEQ ID NO 242
<211> LENGTH: 22
<212> TYPE: RNA
<213> ORGANISM: Homo sapiens

```
<400> SEQUENCE: 242
uucccuuugu cauccuucgc cu                                        22

<210> SEQ ID NO 243
<211> LENGTH: 21
<212> TYPE: RNA
<213> ORGANISM: Homo sapiens

<400> SEQUENCE: 243
uaacagucuc cagucacggc c                                         21

<210> SEQ ID NO 244
<211> LENGTH: 22
<212> TYPE: RNA
<213> ORGANISM: Homo sapiens

<400> SEQUENCE: 244
accaucgacc guugauugua cc                                        22

<210> SEQ ID NO 245
<211> LENGTH: 21
<212> TYPE: RNA
<213> ORGANISM: Homo sapiens

<400> SEQUENCE: 245
acagcaggca cagacaggca g                                         21

<210> SEQ ID NO 246
<211> LENGTH: 21
<212> TYPE: RNA
<213> ORGANISM: Homo sapiens

<400> SEQUENCE: 246
augaccuaug aauugacaga c                                         21

<210> SEQ ID NO 247
<211> LENGTH: 21
<212> TYPE: RNA
<213> ORGANISM: Homo sapiens

<400> SEQUENCE: 247
uaaucucagc uggcaacugu g                                         21

<210> SEQ ID NO 248
<211> LENGTH: 24
<212> TYPE: RNA
<213> ORGANISM: Homo sapiens

<400> SEQUENCE: 248
uacugcauca ggaacugauu ggau                                      24

<210> SEQ ID NO 249
<211> LENGTH: 21
<212> TYPE: RNA
<213> ORGANISM: Homo sapiens

<400> SEQUENCE: 249
uugugcuuga ucuaaccaug u                                         21

<210> SEQ ID NO 250
<211> LENGTH: 21
<212> TYPE: RNA
<213> ORGANISM: Homo sapiens
```

-continued

<400> SEQUENCE: 250
ugauugucca aacgcaauuc u					21

<210> SEQ ID NO 251
<211> LENGTH: 21
<212> TYPE: RNA
<213> ORGANISM: Homo sapiens

<400> SEQUENCE: 251
ccacaccgua ucugacacuu u					21

<210> SEQ ID NO 252
<211> LENGTH: 23
<212> TYPE: RNA
<213> ORGANISM: Homo sapiens

<400> SEQUENCE: 252
agcuacauug ucugcugggu uuc				23

<210> SEQ ID NO 253
<211> LENGTH: 24
<212> TYPE: RNA
<213> ORGANISM: Homo sapiens

<400> SEQUENCE: 253
agcuacaucu ggcuacuggg ucuc				24

<210> SEQ ID NO 254
<211> LENGTH: 21
<212> TYPE: RNA
<213> ORGANISM: Homo sapiens

<400> SEQUENCE: 254
ugucaguuug ucaaauaccc c					21

<210> SEQ ID NO 255
<211> LENGTH: 23
<212> TYPE: RNA
<213> ORGANISM: Homo sapiens

<400> SEQUENCE: 255
caagucacua gugguuccgu uua				23

<210> SEQ ID NO 256
<211> LENGTH: 24
<212> TYPE: RNA
<213> ORGANISM: Homo sapiens

<400> SEQUENCE: 256
cucuaauacu gccugguaau gaug				24

<210> SEQ ID NO 257
<211> LENGTH: 21
<212> TYPE: RNA
<213> ORGANISM: Homo sapiens

<400> SEQUENCE: 257
ugagguagua guuuguacag u					21

<210> SEQ ID NO 258
<211> LENGTH: 19
<212> TYPE: RNA

<213> ORGANISM: Homo sapiens

<400> SEQUENCE: 258
ugagguagua guuugugcu                                                    19

<210> SEQ ID NO 259
<211> LENGTH: 21
<212> TYPE: RNA
<213> ORGANISM: Homo sapiens

<400> SEQUENCE: 259
uggaauguaa agaaguaugu a                                                 21

<210> SEQ ID NO 260
<211> LENGTH: 22
<212> TYPE: RNA
<213> ORGANISM: Homo sapiens

<400> SEQUENCE: 260
uagcagcaca ucaugguuua ca                                                22

<210> SEQ ID NO 261
<211> LENGTH: 23
<212> TYPE: RNA
<213> ORGANISM: Homo sapiens

<400> SEQUENCE: 261
aucacauugc cagggauuac cac                                               23

<210> SEQ ID NO 262
<211> LENGTH: 20
<212> TYPE: RNA
<213> ORGANISM: Homo sapiens

<400> SEQUENCE: 262
uucacagugg cuaaguucug                                                   20

<210> SEQ ID NO 263
<211> LENGTH: 21
<212> TYPE: RNA
<213> ORGANISM: Homo sapiens

<400> SEQUENCE: 263
uguaaacauc cuacacucag c                                                 21

<210> SEQ ID NO 264
<211> LENGTH: 23
<212> TYPE: RNA
<213> ORGANISM: Homo sapiens

<400> SEQUENCE: 264
uggaguguga caaugguguu ugu                                               23

<210> SEQ ID NO 265
<211> LENGTH: 22
<212> TYPE: RNA
<213> ORGANISM: Homo sapiens

<400> SEQUENCE: 265
uuaaggcacg cggugaaugc ca                                                22

<210> SEQ ID NO 266
<211> LENGTH: 22

```
<212> TYPE: RNA
<213> ORGANISM: Homo sapiens

<400> SEQUENCE: 266
ucccugagac ccuaacuugu ga                                          22

<210> SEQ ID NO 267
<211> LENGTH: 22
<212> TYPE: RNA
<213> ORGANISM: Homo sapiens

<400> SEQUENCE: 267
ucacagugaa ccggucucuu uu                                          22

<210> SEQ ID NO 268
<211> LENGTH: 20
<212> TYPE: RNA
<213> ORGANISM: Homo sapiens

<400> SEQUENCE: 268
cagugcaaug uuaaaagggc                                             20

<210> SEQ ID NO 269
<211> LENGTH: 22
<212> TYPE: RNA
<213> ORGANISM: Homo sapiens

<400> SEQUENCE: 269
uaacagucua cagccauggu cg                                          22

<210> SEQ ID NO 270
<211> LENGTH: 22
<212> TYPE: RNA
<213> ORGANISM: Homo sapiens

<400> SEQUENCE: 270
uugguccccu ucaaccagcu gu                                          22

<210> SEQ ID NO 271
<211> LENGTH: 23
<212> TYPE: RNA
<213> ORGANISM: Homo sapiens

<400> SEQUENCE: 271
uauggcuuuu uauuccuaug uga                                         23

<210> SEQ ID NO 272
<211> LENGTH: 22
<212> TYPE: RNA
<213> ORGANISM: Homo sapiens

<400> SEQUENCE: 272
uauugcuuaa gaauacgcgu ag                                          22

<210> SEQ ID NO 273
<211> LENGTH: 17
<212> TYPE: RNA
<213> ORGANISM: Homo sapiens

<400> SEQUENCE: 273
agcugguguu gugaauc                                                17

<210> SEQ ID NO 274
```

```
<211> LENGTH: 21
<212> TYPE: RNA
<213> ORGANISM: Homo sapiens

<400> SEQUENCE: 274
agugguuuua cccauggua g                                          21

<210> SEQ ID NO 275
<211> LENGTH: 21
<212> TYPE: RNA
<213> ORGANISM: Homo sapiens

<400> SEQUENCE: 275
aacacugucu gguaaagaug g                                         21

<210> SEQ ID NO 276
<211> LENGTH: 20
<212> TYPE: RNA
<213> ORGANISM: Homo sapiens

<400> SEQUENCE: 276
cauaaaguag aaagcacuac                                           20

<210> SEQ ID NO 277
<211> LENGTH: 23
<212> TYPE: RNA
<213> ORGANISM: Homo sapiens

<400> SEQUENCE: 277
uguaguguuu ccuacuuuau gga                                       23

<210> SEQ ID NO 278
<211> LENGTH: 22
<212> TYPE: RNA
<213> ORGANISM: Homo sapiens

<400> SEQUENCE: 278
ugagaugaag cacguagcu ca                                         22

<210> SEQ ID NO 279
<211> LENGTH: 22
<212> TYPE: RNA
<213> ORGANISM: Homo sapiens

<400> SEQUENCE: 279
uacaguauag augauguacu ag                                        22

<210> SEQ ID NO 280
<211> LENGTH: 24
<212> TYPE: RNA
<213> ORGANISM: Homo sapiens

<400> SEQUENCE: 280
guccaguuuu cccaggaauc ccuu                                      24

<210> SEQ ID NO 281
<211> LENGTH: 21
<212> TYPE: RNA
<213> ORGANISM: Homo sapiens

<400> SEQUENCE: 281
ucagugcaug acagaacuug g                                         21
```

```
<210> SEQ ID NO 282
<211> LENGTH: 20
<212> TYPE: RNA
<213> ORGANISM: Homo sapiens

<400> SEQUENCE: 282
uugcauaguc acaaaaguga                                              20

<210> SEQ ID NO 283
<211> LENGTH: 22
<212> TYPE: RNA
<213> ORGANISM: Homo sapiens

<400> SEQUENCE: 283
caacggaauc ccaaaagcag cu                                           22

<210> SEQ ID NO 284
<211> LENGTH: 23
<212> TYPE: RNA
<213> ORGANISM: Homo sapiens

<400> SEQUENCE: 284
ucuuugguua ucuagcugua uga                                          23

<210> SEQ ID NO 285
<211> LENGTH: 21
<212> TYPE: RNA
<213> ORGANISM: Homo sapiens

<400> SEQUENCE: 285
uaaagcuaga uaaccgaaag u                                            21

<210> SEQ ID NO 286
<211> LENGTH: 23
<212> TYPE: RNA
<213> ORGANISM: Homo sapiens

<400> SEQUENCE: 286
ucccugagac ccuuuaaccu gug                                          23

<210> SEQ ID NO 287
<211> LENGTH: 21
<212> TYPE: RNA
<213> ORGANISM: Homo sapiens

<400> SEQUENCE: 287
cauuauuacu uuugguacgc g                                            21

<210> SEQ ID NO 288
<211> LENGTH: 21
<212> TYPE: RNA
<213> ORGANISM: Homo sapiens

<400> SEQUENCE: 288
ucguaccgug aguaauaaug c                                            21

<210> SEQ ID NO 289
<211> LENGTH: 22
<212> TYPE: RNA
<213> ORGANISM: Homo sapiens

<400> SEQUENCE: 289
ucggauccgu cugagcuugg cu                                           22
```

```
<210> SEQ ID NO 290
<211> LENGTH: 21
<212> TYPE: RNA
<213> ORGANISM: Homo sapiens

<400> SEQUENCE: 290
cuuuuugcgg ucugggcuug c                                           21

<210> SEQ ID NO 291
<211> LENGTH: 21
<212> TYPE: RNA
<213> ORGANISM: Homo sapiens

<400> SEQUENCE: 291
ugugacuggu ugaccagagg g                                           21

<210> SEQ ID NO 292
<211> LENGTH: 23
<212> TYPE: RNA
<213> ORGANISM: Homo sapiens

<400> SEQUENCE: 292
acuccauuug uuuugaugau gga                                         23

<210> SEQ ID NO 293
<211> LENGTH: 22
<212> TYPE: RNA
<213> ORGANISM: Homo sapiens

<400> SEQUENCE: 293
ugagaacuga auuccauggg uu                                          22

<210> SEQ ID NO 294
<211> LENGTH: 22
<212> TYPE: RNA
<213> ORGANISM: Homo sapiens

<400> SEQUENCE: 294
ucuggcuccg ugucuucacu cc                                          22

<210> SEQ ID NO 295
<211> LENGTH: 22
<212> TYPE: RNA
<213> ORGANISM: Homo sapiens

<400> SEQUENCE: 295
ucucccaacc cuuguaccag ug                                          22

<210> SEQ ID NO 296
<211> LENGTH: 22
<212> TYPE: RNA
<213> ORGANISM: Homo sapiens

<400> SEQUENCE: 296
uagguuaucc guguugccuu cg                                          22

<210> SEQ ID NO 297
<211> LENGTH: 22
<212> TYPE: RNA
<213> ORGANISM: Homo sapiens

<400> SEQUENCE: 297
uggacggaga acugauaagg gu                                          22
```

```
<210> SEQ ID NO 298
<211> LENGTH: 18
<212> TYPE: RNA
<213> ORGANISM: Homo sapiens

<400> SEQUENCE: 298
uggagagaaa ggcaguuc                                                   18

<210> SEQ ID NO 299
<211> LENGTH: 23
<212> TYPE: RNA
<213> ORGANISM: Homo sapiens

<400> SEQUENCE: 299
caaagaauuc uccuuuuggg cuu                                             23

<210> SEQ ID NO 300
<211> LENGTH: 22
<212> TYPE: RNA
<213> ORGANISM: Homo sapiens

<400> SEQUENCE: 300
caucccuugc augguggagg gu                                              22

<210> SEQ ID NO 301
<211> LENGTH: 22
<212> TYPE: RNA
<213> ORGANISM: Homo sapiens

<400> SEQUENCE: 301
ugauauguuu gauauauuag gu                                              22

<210> SEQ ID NO 302
<211> LENGTH: 21
<212> TYPE: RNA
<213> ORGANISM: Homo sapiens

<400> SEQUENCE: 302
aacuggccua caaaguccca g                                               21

<210> SEQ ID NO 303
<211> LENGTH: 22
<212> TYPE: RNA
<213> ORGANISM: Homo sapiens

<400> SEQUENCE: 303
uguaacagca acuccaugug ga                                              22

<210> SEQ ID NO 304
<211> LENGTH: 21
<212> TYPE: RNA
<213> ORGANISM: Homo sapiens

<400> SEQUENCE: 304
uagcagcaca gaaauauugg c                                               21

<210> SEQ ID NO 305
<211> LENGTH: 22
<212> TYPE: RNA
<213> ORGANISM: Homo sapiens

<400> SEQUENCE: 305
```

```
uggaauguaa ggaagugugu gg                                              22

<210> SEQ ID NO 306
<211> LENGTH: 23
<212> TYPE: RNA
<213> ORGANISM: Homo sapiens

<400> SEQUENCE: 306
aaaagcuggg uugagagggc gaa                                             23

<210> SEQ ID NO 307
<211> LENGTH: 21
<212> TYPE: RNA
<213> ORGANISM: Homo sapiens

<400> SEQUENCE: 307
uaagccaggg auguggguu c                                                21

<210> SEQ ID NO 308
<211> LENGTH: 22
<212> TYPE: RNA
<213> ORGANISM: Homo sapiens

<400> SEQUENCE: 308
aauacugccg gguaaugaug ga                                              22

<210> SEQ ID NO 309
<211> LENGTH: 22
<212> TYPE: RNA
<213> ORGANISM: Homo sapiens

<400> SEQUENCE: 309
uuaaugcuaa ucgugauagg gg                                              22

<210> SEQ ID NO 310
<211> LENGTH: 22
<212> TYPE: RNA
<213> ORGANISM: Homo sapiens

<400> SEQUENCE: 310
ucacagugaa ccggucucuu uc                                              22

<210> SEQ ID NO 311
<211> LENGTH: 21
<212> TYPE: RNA
<213> ORGANISM: Homo sapiens

<400> SEQUENCE: 311
uaaagugcug acagugcaga u                                               21

<210> SEQ ID NO 312
<211> LENGTH: 22
<212> TYPE: RNA
<213> ORGANISM: Homo sapiens

<400> SEQUENCE: 312
uagcaccauu ugaaaucggu ua                                              22

<210> SEQ ID NO 313
<211> LENGTH: 22
<212> TYPE: RNA
<213> ORGANISM: Homo sapiens

<400> SEQUENCE: 313
```

```
uaacacuguc ugguaacgau gu                                               22

<210> SEQ ID NO 314
<211> LENGTH: 23
<212> TYPE: RNA
<213> ORGANISM: Homo sapiens

<400> SEQUENCE: 314
uaagugcuuc cauguuuugg uga                                              23

<210> SEQ ID NO 315
<211> LENGTH: 22
<212> TYPE: RNA
<213> ORGANISM: Homo sapiens

<400> SEQUENCE: 315
aggcaguguc auuagcugau ug                                               22

<210> SEQ ID NO 316
<211> LENGTH: 22
<212> TYPE: RNA
<213> ORGANISM: Homo sapiens

<400> SEQUENCE: 316
aggcagugua guuagcugau ug                                               22

<210> SEQ ID NO 317
<211> LENGTH: 22
<212> TYPE: RNA
<213> ORGANISM: Homo sapiens

<400> SEQUENCE: 317
ugguuuaccg ucccacauac au                                               22

<210> SEQ ID NO 318
<211> LENGTH: 23
<212> TYPE: RNA
<213> ORGANISM: Homo sapiens

<400> SEQUENCE: 318
cagugcaaua guauugucaa agc                                              23

<210> SEQ ID NO 319
<211> LENGTH: 22
<212> TYPE: RNA
<213> ORGANISM: Homo sapiens

<400> SEQUENCE: 319
cacccguaga accgaccuug cg                                               22

<210> SEQ ID NO 320
<211> LENGTH: 21
<212> TYPE: RNA
<213> ORGANISM: Homo sapiens

<400> SEQUENCE: 320
agggcccccc cucaauccug u                                                21

<210> SEQ ID NO 321
<211> LENGTH: 22
<212> TYPE: RNA
<213> ORGANISM: Homo sapiens
```

```
<400> SEQUENCE: 321
cagugcaaug augaaagggc au                                        22

<210> SEQ ID NO 322
<211> LENGTH: 20
<212> TYPE: RNA
<213> ORGANISM: Homo sapiens

<400> SEQUENCE: 322
uguaaacauc cuugacugga                                           20

<210> SEQ ID NO 323
<211> LENGTH: 23
<212> TYPE: RNA
<213> ORGANISM: Homo sapiens

<400> SEQUENCE: 323
uccgucucag uuacuuuaua gcc                                       23

<210> SEQ ID NO 324
<211> LENGTH: 23
<212> TYPE: RNA
<213> ORGANISM: Homo sapiens

<400> SEQUENCE: 324
gcaaagcaca cggccugcag aga                                       23

<210> SEQ ID NO 325
<211> LENGTH: 22
<212> TYPE: RNA
<213> ORGANISM: Homo sapiens

<400> SEQUENCE: 325
cuggcccucu cugcccuucc gu                                        22

<210> SEQ ID NO 326
<211> LENGTH: 24
<212> TYPE: RNA
<213> ORGANISM: Homo sapiens

<400> SEQUENCE: 326
ucucacacag aaaucgcacc cguc                                      24

<210> SEQ ID NO 327
<211> LENGTH: 23
<212> TYPE: RNA
<213> ORGANISM: Homo sapiens

<400> SEQUENCE: 327
uccagcuccu auaugaugcc uuu                                       23

<210> SEQ ID NO 328
<211> LENGTH: 22
<212> TYPE: RNA
<213> ORGANISM: Homo sapiens

<400> SEQUENCE: 328
gcacauuaca cggucgaccu cu                                        22

<210> SEQ ID NO 329
<211> LENGTH: 20
<212> TYPE: RNA
<213> ORGANISM: Homo sapiens
```

```
<400> SEQUENCE: 329
ccucuggscc cuuccuccag                                        20

<210> SEQ ID NO 330
<211> LENGTH: 22
<212> TYPE: RNA
<213> ORGANISM: Homo sapiens

<400> SEQUENCE: 330
acuagacuga agcuccuuga gg                                     22

<210> SEQ ID NO 331
<211> LENGTH: 22
<212> TYPE: RNA
<213> ORGANISM: Homo sapiens

<400> SEQUENCE: 331
uauggcuuuu cauuccuaug ug                                     22

<210> SEQ ID NO 332
<211> LENGTH: 22
<212> TYPE: RNA
<213> ORGANISM: Homo sapiens

<400> SEQUENCE: 332
ucagugcauc acagaacuuu gu                                     22

<210> SEQ ID NO 333
<211> LENGTH: 21
<212> TYPE: RNA
<213> ORGANISM: Homo sapiens

<400> SEQUENCE: 333
gccccugggc cuauccuaga a                                      21

<210> SEQ ID NO 334
<211> LENGTH: 23
<212> TYPE: RNA
<213> ORGANISM: Homo sapiens

<400> SEQUENCE: 334
cgcauccccu agggcauugg ugu                                    23

<210> SEQ ID NO 335
<211> LENGTH: 22
<212> TYPE: RNA
<213> ORGANISM: Homo sapiens

<400> SEQUENCE: 335
ccacugcccc aggugcugcu gg                                     22

<210> SEQ ID NO 336
<211> LENGTH: 23
<212> TYPE: RNA
<213> ORGANISM: Homo sapiens

<400> SEQUENCE: 336
uccagcauca gugauuuugu uga                                    23

<210> SEQ ID NO 337
<211> LENGTH: 21
<212> TYPE: RNA
```

```
<213> ORGANISM: Homo sapiens

<400> SEQUENCE: 337
ucccuguccu ccaggagcuc a                                              21

<210> SEQ ID NO 338
<211> LENGTH: 23
<212> TYPE: RNA
<213> ORGANISM: Homo sapiens

<400> SEQUENCE: 338
ucaagagcaa uaacgaaaaa ugu                                            23

<210> SEQ ID NO 339
<211> LENGTH: 21
<212> TYPE: RNA
<213> ORGANISM: Homo sapiens

<400> SEQUENCE: 339
uugguccccu ucaaccagcu a                                              21

<210> SEQ ID NO 340
<211> LENGTH: 20
<212> TYPE: RNA
<213> ORGANISM: Oryza sp.

<400> SEQUENCE: 340
ugacagaaga gagugagcac                                                20

<210> SEQ ID NO 341
<211> LENGTH: 21
<212> TYPE: RNA
<213> ORGANISM: Oryza sp.

<400> SEQUENCE: 341
ugccuggcuc ccuguaugcc a                                              21

<210> SEQ ID NO 342
<211> LENGTH: 21
<212> TYPE: RNA
<213> ORGANISM: Oryza sp.

<400> SEQUENCE: 342
ucgauaaacc ucugcaucca g                                              21

<210> SEQ ID NO 343
<211> LENGTH: 21
<212> TYPE: RNA
<213> ORGANISM: Oryza sp.

<400> SEQUENCE: 343
uggagaagca gggcacgugc a                                              21

<210> SEQ ID NO 344
<211> LENGTH: 21
<212> TYPE: RNA
<213> ORGANISM: Oryza sp.

<400> SEQUENCE: 344
ucggaccagg cuucauuccc c                                              21

<210> SEQ ID NO 345
<211> LENGTH: 21
```

```
<212> TYPE: RNA
<213> ORGANISM: Oryza sp.

<400> SEQUENCE: 345
ugaagcugcc agcaugaucu a                                              21

<210> SEQ ID NO 346
<211> LENGTH: 21
<212> TYPE: RNA
<213> ORGANISM: Oryza sp.

<400> SEQUENCE: 346
cagccaagga ugacuugccg a                                              21

<210> SEQ ID NO 347
<211> LENGTH: 21
<212> TYPE: RNA
<213> ORGANISM: Oryza sp.

<400> SEQUENCE: 347
ugauugagcc gcgccaauau c                                              21

<210> SEQ ID NO 348
<211> LENGTH: 21
<212> TYPE: RNA
<213> ORGANISM: Mus sp.

<400> SEQUENCE: 348
ugagguagua guuuguacag u                                              21

<210> SEQ ID NO 349
<211> LENGTH: 19
<212> TYPE: RNA
<213> ORGANISM: Mus sp.

<400> SEQUENCE: 349
ugagguagua guuugugcu                                                 19

<210> SEQ ID NO 350
<211> LENGTH: 21
<212> TYPE: RNA
<213> ORGANISM: Mus sp.

<400> SEQUENCE: 350
uggaauguaa agaaguaugu a                                              21

<210> SEQ ID NO 351
<211> LENGTH: 22
<212> TYPE: RNA
<213> ORGANISM: Mus sp.

<400> SEQUENCE: 351
uagcagcaca ucaugguuua ca                                             22

<210> SEQ ID NO 352
<211> LENGTH: 23
<212> TYPE: RNA
<213> ORGANISM: Mus sp.

<400> SEQUENCE: 352
aucacauugc cagggauuac cac                                            23

<210> SEQ ID NO 353
```

```
<211> LENGTH: 20
<212> TYPE: RNA
<213> ORGANISM: Mus sp.

<400> SEQUENCE: 353
uucacagugg cuaaguucug                                              20

<210> SEQ ID NO 354
<211> LENGTH: 22
<212> TYPE: RNA
<213> ORGANISM: Mus sp.

<400> SEQUENCE: 354
uagcaccauu ugaaaucagu gu                                           22

<210> SEQ ID NO 355
<211> LENGTH: 23
<212> TYPE: RNA
<213> ORGANISM: Mus sp.

<400> SEQUENCE: 355
uguaaacauc cucgacugga agc                                          23

<210> SEQ ID NO 356
<211> LENGTH: 22
<212> TYPE: RNA
<213> ORGANISM: Mus sp.

<400> SEQUENCE: 356
cuuucagucg gauguuugca gc                                           22

<210> SEQ ID NO 357
<211> LENGTH: 21
<212> TYPE: RNA
<213> ORGANISM: Mus sp.

<400> SEQUENCE: 357
uguaaacauc cuacacucag c                                            21

<210> SEQ ID NO 358
<211> LENGTH: 20
<212> TYPE: RNA
<213> ORGANISM: Mus sp.

<400> SEQUENCE: 358
acccguagau ccgaucuugu                                              20

<210> SEQ ID NO 359
<211> LENGTH: 22
<212> TYPE: RNA
<213> ORGANISM: Mus sp.

<400> SEQUENCE: 359
cacccguaga accgaccuug cg                                           22

<210> SEQ ID NO 360
<211> LENGTH: 20
<212> TYPE: RNA
<213> ORGANISM: Mus sp.

<400> SEQUENCE: 360
uacaguacug ugauaacuga                                              20
```

```
<210> SEQ ID NO 361
<211> LENGTH: 22
<212> TYPE: RNA
<213> ORGANISM: Mus sp.

<400> SEQUENCE: 361
uuaaggcacg cggugaaugc ca                                              22

<210> SEQ ID NO 362
<211> LENGTH: 23
<212> TYPE: RNA
<213> ORGANISM: Mus sp.

<400> SEQUENCE: 362
ucccugagac ccuuuaaccu gug                                             23

<210> SEQ ID NO 363
<211> LENGTH: 22
<212> TYPE: RNA
<213> ORGANISM: Mus sp.

<400> SEQUENCE: 363
ucccugagac ccuaacuugu ga                                              22

<210> SEQ ID NO 364
<211> LENGTH: 21
<212> TYPE: RNA
<213> ORGANISM: Mus sp.

<400> SEQUENCE: 364
cauuauuacu uuugguacgc g                                               21

<210> SEQ ID NO 365
<211> LENGTH: 21
<212> TYPE: RNA
<213> ORGANISM: Mus sp.

<400> SEQUENCE: 365
ucguaccgug aguaauaaug c                                               21

<210> SEQ ID NO 366
<211> LENGTH: 22
<212> TYPE: RNA
<213> ORGANISM: Mus sp.

<400> SEQUENCE: 366
ucggauccgu cugagcuugg cu                                              22

<210> SEQ ID NO 367
<211> LENGTH: 22
<212> TYPE: RNA
<213> ORGANISM: Mus sp.

<400> SEQUENCE: 367
ucacagugaa ccggucucuu uu                                              22

<210> SEQ ID NO 368
<211> LENGTH: 20
<212> TYPE: RNA
<213> ORGANISM: Mus sp.

<400> SEQUENCE: 368
cagugcaaug uuaaaagggc                                                 20
```

```
<210> SEQ ID NO 369
<211> LENGTH: 23
<212> TYPE: RNA
<213> ORGANISM: Mus sp.

<400> SEQUENCE: 369
ucuuugguua ucuagcugua uga                                               23

<210> SEQ ID NO 370
<211> LENGTH: 21
<212> TYPE: RNA
<213> ORGANISM: Mus sp.

<400> SEQUENCE: 370
uaaagcuaga uaaccgaaag u                                                 21

<210> SEQ ID NO 371
<211> LENGTH: 22
<212> TYPE: RNA
<213> ORGANISM: Mus sp.

<400> SEQUENCE: 371
uaacagucua cagccauggu cg                                                22

<210> SEQ ID NO 372
<211> LENGTH: 22
<212> TYPE: RNA
<213> ORGANISM: Mus sp.

<400> SEQUENCE: 372
uugguccccu ucaaccagcu gu                                                22

<210> SEQ ID NO 373
<211> LENGTH: 21
<212> TYPE: RNA
<213> ORGANISM: Mus sp.

<400> SEQUENCE: 373
ugugacuggu ugaccagagg g                                                 21

<210> SEQ ID NO 374
<211> LENGTH: 23
<212> TYPE: RNA
<213> ORGANISM: Mus sp.

<400> SEQUENCE: 374
uauggcuuuu uauuccuaug uga                                               23

<210> SEQ ID NO 375
<211> LENGTH: 23
<212> TYPE: RNA
<213> ORGANISM: Mus sp.

<400> SEQUENCE: 375
acuccauuug uuuugaugau gga                                               23

<210> SEQ ID NO 376
<211> LENGTH: 22
<212> TYPE: RNA
<213> ORGANISM: Mus sp.

<400> SEQUENCE: 376
uauugcuuaa gaauacgcgu ag                                                22
```

```
<210> SEQ ID NO 377
<211> LENGTH: 17
<212> TYPE: RNA
<213> ORGANISM: Mus sp.

<400> SEQUENCE: 377
agcugguguu gugaauc                                                      17

<210> SEQ ID NO 378
<211> LENGTH: 21
<212> TYPE: RNA
<213> ORGANISM: Mus sp.

<400> SEQUENCE: 378
agugguuuua cccuauggua g                                                 21

<210> SEQ ID NO 379
<211> LENGTH: 21
<212> TYPE: RNA
<213> ORGANISM: Mus sp.

<400> SEQUENCE: 379
aacacugucu gguaaagaug g                                                 21

<210> SEQ ID NO 380
<211> LENGTH: 20
<212> TYPE: RNA
<213> ORGANISM: Mus sp.

<400> SEQUENCE: 380
cauaaaguag aaagcacuac                                                   20

<210> SEQ ID NO 381
<211> LENGTH: 22
<212> TYPE: RNA
<213> ORGANISM: Mus sp.

<400> SEQUENCE: 381
uguaguguuu ccuacuuuau gg                                                22

<210> SEQ ID NO 382
<211> LENGTH: 22
<212> TYPE: RNA
<213> ORGANISM: Mus sp.

<400> SEQUENCE: 382
uacaguauag augauguacu ag                                                22

<210> SEQ ID NO 383
<211> LENGTH: 24
<212> TYPE: RNA
<213> ORGANISM: Mus sp.

<400> SEQUENCE: 383
guccaguuuu cccaggaauc ccuu                                              24

<210> SEQ ID NO 384
<211> LENGTH: 22
<212> TYPE: RNA
<213> ORGANISM: Mus sp.

<400> SEQUENCE: 384
```
ugagaacuga auuccauggg uu                     22

<210> SEQ ID NO 385
<211> LENGTH: 22
<212> TYPE: RNA
<213> ORGANISM: Mus sp.

<400> SEQUENCE: 385
ucuggcuccg ugucuucacu cc                     22

<210> SEQ ID NO 386
<211> LENGTH: 22
<212> TYPE: RNA
<213> ORGANISM: Mus sp.

<400> SEQUENCE: 386
ucucccaacc cuuguaccag ug                     22

<210> SEQ ID NO 387
<211> LENGTH: 21
<212> TYPE: RNA
<213> ORGANISM: Mus sp.

<400> SEQUENCE: 387
cuagacugag gcuccuugag g                      21

<210> SEQ ID NO 388
<211> LENGTH: 21
<212> TYPE: RNA
<213> ORGANISM: Mus sp.

<400> SEQUENCE: 388
ucagugcaug acagaacuug g                      21

<210> SEQ ID NO 389
<211> LENGTH: 20
<212> TYPE: RNA
<213> ORGANISM: Mus sp.

<400> SEQUENCE: 389
uugcauaguc acaaaaguga                        20

<210> SEQ ID NO 390
<211> LENGTH: 22
<212> TYPE: RNA
<213> ORGANISM: Mus sp.

<400> SEQUENCE: 390
uagguuaucc guguugccuu cg                     22

<210> SEQ ID NO 391
<211> LENGTH: 22
<212> TYPE: RNA
<213> ORGANISM: Mus sp.

<400> SEQUENCE: 391
uuaaugcuaa uugugauagg gg                     22

<210> SEQ ID NO 392
<211> LENGTH: 22
<212> TYPE: RNA
<213> ORGANISM: Mus sp.

<400> SEQUENCE: 392

```
cccuguagaa ccgaauuugu gu                                              22

<210> SEQ ID NO 393
<211> LENGTH: 22
<212> TYPE: RNA
<213> ORGANISM: Mus sp.

<400> SEQUENCE: 393
cuuuuugcgg ucugggcuug cu                                              22

<210> SEQ ID NO 394
<211> LENGTH: 23
<212> TYPE: RNA
<213> ORGANISM: Mus sp.

<400> SEQUENCE: 394
aacauucaac gcugucggug agu                                             23

<210> SEQ ID NO 395
<211> LENGTH: 22
<212> TYPE: RNA
<213> ORGANISM: Mus sp.

<400> SEQUENCE: 395
uuuggcaaug guagaacuca ca                                              22

<210> SEQ ID NO 396
<211> LENGTH: 23
<212> TYPE: RNA
<213> ORGANISM: Mus sp.

<400> SEQUENCE: 396
uauggcacug guagaauuca cug                                             23

<210> SEQ ID NO 397
<211> LENGTH: 22
<212> TYPE: RNA
<213> ORGANISM: Mus sp.

<400> SEQUENCE: 397
uggacggaga acugauaagg gu                                              22

<210> SEQ ID NO 398
<211> LENGTH: 18
<212> TYPE: RNA
<213> ORGANISM: Mus sp.

<400> SEQUENCE: 398
uggagagaaa ggcaguuc                                                   18

<210> SEQ ID NO 399
<211> LENGTH: 23
<212> TYPE: RNA
<213> ORGANISM: Mus sp.

<400> SEQUENCE: 399
caaagaauuc uccuuuuggg cuu                                             23

<210> SEQ ID NO 400
<211> LENGTH: 22
<212> TYPE: RNA
<213> ORGANISM: Mus sp.
```

```
<400> SEQUENCE: 400
ucgugucuug uguugcagcc gg                                              22

<210> SEQ ID NO 401
<211> LENGTH: 22
<212> TYPE: RNA
<213> ORGANISM: Mus sp.

<400> SEQUENCE: 401
caucccuugc augguggagg gu                                              22

<210> SEQ ID NO 402
<211> LENGTH: 23
<212> TYPE: RNA
<213> ORGANISM: Mus sp.

<400> SEQUENCE: 402
gugccuacug agcugauauc agu                                             23

<210> SEQ ID NO 403
<211> LENGTH: 22
<212> TYPE: RNA
<213> ORGANISM: Mus sp.

<400> SEQUENCE: 403
uggcucaguu cagcaggaac ag                                              22

<210> SEQ ID NO 404
<211> LENGTH: 22
<212> TYPE: RNA
<213> ORGANISM: Mus sp.

<400> SEQUENCE: 404
ugauauguuu gauauauuag gu                                              22

<210> SEQ ID NO 405
<211> LENGTH: 22
<212> TYPE: RNA
<213> ORGANISM: Mus sp.

<400> SEQUENCE: 405
caacggaauc ccaaaagcag cu                                              22

<210> SEQ ID NO 406
<211> LENGTH: 21
<212> TYPE: RNA
<213> ORGANISM: Mus sp.

<400> SEQUENCE: 406
aacuggccua caaaguccca g                                               21

<210> SEQ ID NO 407
<211> LENGTH: 22
<212> TYPE: RNA
<213> ORGANISM: Mus sp.

<400> SEQUENCE: 407
uguaacagca acuccaugug ga                                              22

<210> SEQ ID NO 408
<211> LENGTH: 21
<212> TYPE: RNA
<213> ORGANISM: Mus sp.
```

```
<400> SEQUENCE: 408
uagcagcaca gaaauauugg c                                          21

<210> SEQ ID NO 409
<211> LENGTH: 23
<212> TYPE: RNA
<213> ORGANISM: Mus sp.

<400> SEQUENCE: 409
cccaguguuc agacuaccug uuc                                        23

<210> SEQ ID NO 410
<211> LENGTH: 22
<212> TYPE: RNA
<213> ORGANISM: Mus sp.

<400> SEQUENCE: 410
uacaguaguc ugcacauugg uu                                         22

<210> SEQ ID NO 411
<211> LENGTH: 23
<212> TYPE: RNA
<213> ORGANISM: Mus sp.

<400> SEQUENCE: 411
uaauacugcc ugguaaugau gac                                        23

<210> SEQ ID NO 412
<211> LENGTH: 21
<212> TYPE: RNA
<213> ORGANISM: Mus sp.

<400> SEQUENCE: 412
uacucaguaa ggcauuguuc u                                          21

<210> SEQ ID NO 413
<211> LENGTH: 22
<212> TYPE: RNA
<213> ORGANISM: Mus sp.

<400> SEQUENCE: 413
agagguauag cgcaugggaa ga                                         22

<210> SEQ ID NO 414
<211> LENGTH: 21
<212> TYPE: RNA
<213> ORGANISM: Mus sp.

<400> SEQUENCE: 414
ugaaauguuu aggaccacua g                                          21

<210> SEQ ID NO 415
<211> LENGTH: 23
<212> TYPE: RNA
<213> ORGANISM: Mus sp.

<400> SEQUENCE: 415
uucccuuugu cauccaugc cug                                         23

<210> SEQ ID NO 416
<211> LENGTH: 22
<212> TYPE: RNA
```

```
<213> ORGANISM: Mus sp.

<400> SEQUENCE: 416
uccuucauuc caccggaguc ug                                      22

<210> SEQ ID NO 417
<211> LENGTH: 22
<212> TYPE: RNA
<213> ORGANISM: Mus sp.

<400> SEQUENCE: 417
uggaauguaa ggaagugugu gg                                      22

<210> SEQ ID NO 418
<211> LENGTH: 23
<212> TYPE: RNA
<213> ORGANISM: Mus sp.

<400> SEQUENCE: 418
gcuucuccug gcucuccucc cuc                                     23

<210> SEQ ID NO 419
<211> LENGTH: 23
<212> TYPE: RNA
<213> ORGANISM: Mus sp.

<400> SEQUENCE: 419
uggaguguga caaugguguu ugu                                     23

<210> SEQ ID NO 420
<211> LENGTH: 22
<212> TYPE: RNA
<213> ORGANISM: Mus sp.

<400> SEQUENCE: 420
ugagaugaag cacguagcu ca                                       22

<210> SEQ ID NO 421
<211> LENGTH: 20
<212> TYPE: RNA
<213> ORGANISM: Mus sp.

<400> SEQUENCE: 421
uguaaacauc cuugacugga                                         20

<210> SEQ ID NO 422
<211> LENGTH: 23
<212> TYPE: RNA
<213> ORGANISM: Mus sp.

<400> SEQUENCE: 422
cucaaacuau gggggcacuu uuu                                     23

<210> SEQ ID NO 423
<211> LENGTH: 22
<212> TYPE: RNA
<213> ORGANISM: Mus sp.

<400> SEQUENCE: 423
caucaaagug gaggcccucu cu                                      22

<210> SEQ ID NO 424
<211> LENGTH: 23
```

```
<212> TYPE: RNA
<213> ORGANISM: Mus sp.

<400> SEQUENCE: 424
aaagugcuuc cacuuugugu gcc                                              23

<210> SEQ ID NO 425
<211> LENGTH: 22
<212> TYPE: RNA
<213> ORGANISM: Mus sp.

<400> SEQUENCE: 425
acucaaacug ggggcucuuu ug                                               22

<210> SEQ ID NO 426
<211> LENGTH: 23
<212> TYPE: RNA
<213> ORGANISM: Mus sp.

<400> SEQUENCE: 426
aagugccgcc agguuugag ugu                                               23

<210> SEQ ID NO 427
<211> LENGTH: 22
<212> TYPE: RNA
<213> ORGANISM: Mus sp.

<400> SEQUENCE: 427
agugccgcag aguuguagu gu                                                22

<210> SEQ ID NO 428
<211> LENGTH: 22
<212> TYPE: RNA
<213> ORGANISM: Mus sp.

<400> SEQUENCE: 428
aaagugcuuc ccuuuugugu gu                                               22

<210> SEQ ID NO 429
<211> LENGTH: 23
<212> TYPE: RNA
<213> ORGANISM: Mus sp.

<400> SEQUENCE: 429
aaagugcuac uacuuugag ucu                                               23

<210> SEQ ID NO 430
<211> LENGTH: 21
<212> TYPE: RNA
<213> ORGANISM: Mus sp.

<400> SEQUENCE: 430 agggccccccc cucaauccug u                                               21

<210> SEQ ID NO 431
<211> LENGTH: 21
<212> TYPE: RNA
<213> ORGANISM: Mus sp.

<400> SEQUENCE: 431
auguaugugu gcaugugcau g                                                21

<210> SEQ ID NO 432
```

```
<211> LENGTH: 22
<212> TYPE: RNA
<213> ORGANISM: Mus sp.

<400> SEQUENCE: 432
ggcagaggag ggcuguucuu cc                                              22

<210> SEQ ID NO 433
<211> LENGTH: 22
<212> TYPE: RNA
<213> ORGANISM: Mus sp.

<400> SEQUENCE: 433
ugguuuaccg ucccacauac au                                              22

<210> SEQ ID NO 434
<211> LENGTH: 22
<212> TYPE: RNA
<213> ORGANISM: Mus sp.

<400> SEQUENCE: 434
uaugcaaggg caagcucucu uc                                              22

<210> SEQ ID NO 435
<211> LENGTH: 23
<212> TYPE: RNA
<213> ORGANISM: Mus sp.

<400> SEQUENCE: 435
cagugcaaua guauugucaa agc                                             23

<210> SEQ ID NO 436
<211> LENGTH: 23
<212> TYPE: RNA
<213> ORGANISM: Mus sp.

<400> SEQUENCE: 436
uaagugcuuc cauguuuugg uga                                             23

<210> SEQ ID NO 437
<211> LENGTH: 23
<212> TYPE: RNA
<213> ORGANISM: Mus sp.

<400> SEQUENCE: 437
aggcagugua guuagcugau ugc                                             23

<210> SEQ ID NO 438
<211> LENGTH: 23
<212> TYPE: RNA
<213> ORGANISM: Mus sp.

<400> SEQUENCE: 438
uaggcagugu aauuagcuga uug                                             23

<210> SEQ ID NO 439
<211> LENGTH: 21
<212> TYPE: RNA
<213> ORGANISM: Mus sp.

<400> SEQUENCE: 439
agagguagua gguugcauag u                                               21
```

```
<210> SEQ ID NO 440
<211> LENGTH: 22
<212> TYPE: RNA
<213> ORGANISM: Mus sp.

<400> SEQUENCE: 440
cuauacgacc ugcugccuuu cu                                              22

<210> SEQ ID NO 441
<211> LENGTH: 22
<212> TYPE: RNA
<213> ORGANISM: Mus sp.

<400> SEQUENCE: 441
caaagugcua acagugcagg ua                                              22

<210> SEQ ID NO 442
<211> LENGTH: 21
<212> TYPE: RNA
<213> ORGANISM: Mus sp.

<400> SEQUENCE: 442
uaaagugcug acagugcaga u                                               21

<210> SEQ ID NO 443
<211> LENGTH: 22
<212> TYPE: RNA
<213> ORGANISM: Mus sp.

<400> SEQUENCE: 443
cagugcaaug augaaagggc au                                              22

<210> SEQ ID NO 444
<211> LENGTH: 23
<212> TYPE: RNA
<213> ORGANISM: Mus sp.

<400> SEQUENCE: 444
ugugcaaauc caugcaaaac uga                                             23

<210> SEQ ID NO 445
<211> LENGTH: 23
<212> TYPE: RNA
<213> ORGANISM: Mus sp.

<400> SEQUENCE: 445
uguaaacauc cuacacucuc agc                                             23

<210> SEQ ID NO 446
<211> LENGTH: 22
<212> TYPE: RNA
<213> ORGANISM: Mus sp.

<400> SEQUENCE: 446
uguaaacauc cccgacugga ag                                              22

<210> SEQ ID NO 447
<211> LENGTH: 22
<212> TYPE: RNA
<213> ORGANISM: Mus sp.

<400> SEQUENCE: 447
ucagugcacu acagaacuuu gu                                              22
```

-continued

```
<210> SEQ ID NO 448
<211> LENGTH: 18
<212> TYPE: RNA
<213> ORGANISM: Mus sp.

<400> SEQUENCE: 448
cugaccuaug aauugaca                                                   18

<210> SEQ ID NO 449
<211> LENGTH: 21
<212> TYPE: RNA
<213> ORGANISM: Mus sp.

<400> SEQUENCE: 449
uagguaguuu cauguuguug g                                               21

<210> SEQ ID NO 450
<211> LENGTH: 22
<212> TYPE: RNA
<213> ORGANISM: Mus sp.

<400> SEQUENCE: 450
uaacacuguc ugguaacgau gu                                              22

<210> SEQ ID NO 451
<211> LENGTH: 22
<212> TYPE: RNA
<213> ORGANISM: Mus sp.

<400> SEQUENCE: 451
auaagacgag caaaaagcuu gu                                              22

<210> SEQ ID NO 452
<211> LENGTH: 22
<212> TYPE: RNA
<213> ORGANISM: Mus sp.

<400> SEQUENCE: 452
ugagguagua gguuguauag uu                                              22

<210> SEQ ID NO 453
<211> LENGTH: 22
<212> TYPE: RNA
<213> ORGANISM: Mus sp.

<400> SEQUENCE: 453
ugagguagua gguugugugg uu                                              22

<210> SEQ ID NO 454
<211> LENGTH: 22
<212> TYPE: RNA
<213> ORGANISM: Mus sp.

<400> SEQUENCE: 454
ugagguagua gguuguaugg uu                                              22

<210> SEQ ID NO 455
<211> LENGTH: 21
<212> TYPE: RNA
<213> ORGANISM: Mus sp.

<400> SEQUENCE: 455
ugagguagga gguuguauag u                                               21
```

<210> SEQ ID NO 456
<211> LENGTH: 22
<212> TYPE: RNA
<213> ORGANISM: Mus sp.

<400> SEQUENCE: 456
ugagguagua gauuguauag uu                                              22

<210> SEQ ID NO 457
<211> LENGTH: 22
<212> TYPE: RNA
<213> ORGANISM: Mus sp.

<400> SEQUENCE: 457
uagcagcaca uaaugguuug ug                                              22

<210> SEQ ID NO 458
<211> LENGTH: 22
<212> TYPE: RNA
<213> ORGANISM: Mus sp.

<400> SEQUENCE: 458
uagcagcacg uaaauauugg cg                                              22

<210> SEQ ID NO 459
<211> LENGTH: 22
<212> TYPE: RNA
<213> ORGANISM: Mus sp.

<400> SEQUENCE: 459
uaaggugcau cuagugcaga ua                                              22

<210> SEQ ID NO 460
<211> LENGTH: 23
<212> TYPE: RNA
<213> ORGANISM: Mus sp.

<400> SEQUENCE: 460
uaaagugcuu auagugcagg uag                                             23

<210> SEQ ID NO 461
<211> LENGTH: 22
<212> TYPE: RNA
<213> ORGANISM: Mus sp.

<400> SEQUENCE: 461
uagcuuauca gacugauguu ga                                              22

<210> SEQ ID NO 462
<211> LENGTH: 22
<212> TYPE: RNA
<213> ORGANISM: Mus sp.

<400> SEQUENCE: 462
aagcugccag uugaagaacu gu                                              22

<210> SEQ ID NO 463
<211> LENGTH: 21
<212> TYPE: RNA
<213> ORGANISM: Mus sp.

<400> SEQUENCE: 463
aucacauugc cagggauuuc c    21

<210> SEQ ID NO 464
<211> LENGTH: 22
<212> TYPE: RNA
<213> ORGANISM: Mus sp.

<400> SEQUENCE: 464
uucaaguaau ccaggauagg cu    22

<210> SEQ ID NO 465
<211> LENGTH: 22
<212> TYPE: RNA
<213> ORGANISM: Mus sp.

<400> SEQUENCE: 465
uucaaguaau ucaggauagg uu    22

<210> SEQ ID NO 466
<211> LENGTH: 22
<212> TYPE: RNA
<213> ORGANISM: Mus sp.

<400> SEQUENCE: 466
cuagcaccau cugaaaucgg uu    22

<210> SEQ ID NO 467
<211> LENGTH: 22
<212> TYPE: RNA
<213> ORGANISM: Mus sp.

<400> SEQUENCE: 467
uagcaccauu ugaaaucggu ua    22

<210> SEQ ID NO 468
<211> LENGTH: 21
<212> TYPE: RNA
<213> ORGANISM: Mus sp.

<400> SEQUENCE: 468
uucacagugg cuaaguuccg c    21

<210> SEQ ID NO 469
<211> LENGTH: 22
<212> TYPE: RNA
<213> ORGANISM: Mus sp.

<400> SEQUENCE: 469
aggcaagaug cuggcauagc ug    22

<210> SEQ ID NO 470
<211> LENGTH: 21
<212> TYPE: RNA
<213> ORGANISM: Mus sp.

<400> SEQUENCE: 470
uauugcacuu gucccggccu g    21

<210> SEQ ID NO 471
<211> LENGTH: 23
<212> TYPE: RNA
<213> ORGANISM: Mus sp.

<400> SEQUENCE: 471
caaagugcug uucgugcagg uag                                          23

<210> SEQ ID NO 472
<211> LENGTH: 23
<212> TYPE: RNA
<213> ORGANISM: Mus sp.

<400> SEQUENCE: 472
uuuggcacua gcacauuuuu gcu                                          23

<210> SEQ ID NO 473
<211> LENGTH: 23
<212> TYPE: RNA
<213> ORGANISM: Mus sp.

<400> SEQUENCE: 473
uggcaguguc uuagcugguu guu                                          23

<210> SEQ ID NO 474
<211> LENGTH: 22
<212> TYPE: RNA
<213> ORGANISM: Mus sp.

<400> SEQUENCE: 474
ugagguagua aguuguauug uu                                           22

<210> SEQ ID NO 475
<211> LENGTH: 23
<212> TYPE: RNA
<213> ORGANISM: Mus sp.

<400> SEQUENCE: 475
agcagcauug uacagggcua uga                                          23

<210> SEQ ID NO 476
<211> LENGTH: 22
<212> TYPE: RNA
<213> ORGANISM: Mus sp.

<400> SEQUENCE: 476
gcacauuaca cggucgaccu cu                                           22

<210> SEQ ID NO 477
<211> LENGTH: 23
<212> TYPE: RNA
<213> ORGANISM: Mus sp.

<400> SEQUENCE: 477
cgcauccccu agggcauugg ugu                                          23

<210> SEQ ID NO 478
<211> LENGTH: 22
<212> TYPE: RNA
<213> ORGANISM: Mus sp.

<400> SEQUENCE: 478
ccacugcccc aggugcugcu gg                                           22

<210> SEQ ID NO 479
<211> LENGTH: 23
<212> TYPE: RNA
<213> ORGANISM: Mus sp.

```
<400> SEQUENCE: 479
ccuaguaggu gcucaguaag ugu                                          23

<210> SEQ ID NO 480
<211> LENGTH: 21
<212> TYPE: RNA
<213> ORGANISM: Mus sp.

<400> SEQUENCE: 480
ccucugggcc cuuccuccag u                                            21

<210> SEQ ID NO 481
<211> LENGTH: 22
<212> TYPE: RNA
<213> ORGANISM: Mus sp.

<400> SEQUENCE: 481
cuggcccucu cugcccuucc gu                                           22

<210> SEQ ID NO 482
<211> LENGTH: 22
<212> TYPE: RNA
<213> ORGANISM: Mus sp.

<400> SEQUENCE: 482
aacacaccca gcuaaccuuu uu                                           22

<210> SEQ ID NO 483
<211> LENGTH: 23
<212> TYPE: RNA
<213> ORGANISM: Mus sp.

<400> SEQUENCE: 483
gcaaagcaca gggccugcag aga                                          23

<210> SEQ ID NO 484
<211> LENGTH: 21
<212> TYPE: RNA
<213> ORGANISM: Mus sp.

<400> SEQUENCE: 484
gccccugggc cuauccuaga a                                            21

<210> SEQ ID NO 485
<211> LENGTH: 23
<212> TYPE: RNA
<213> ORGANISM: Mus sp.

<400> SEQUENCE: 485
uucagcuccu auaugaugcc uuu                                          23

<210> SEQ ID NO 486
<211> LENGTH: 23
<212> TYPE: RNA
<213> ORGANISM: Mus sp.

<400> SEQUENCE: 486
uccagcauca gugauuuugu uga                                          23

<210> SEQ ID NO 487
<211> LENGTH: 21
<212> TYPE: RNA
<213> ORGANISM: Mus sp.
```

<400> SEQUENCE: 487
ucccuguccu ccaggagcuc a                                            21

<210> SEQ ID NO 488
<211> LENGTH: 23
<212> TYPE: RNA
<213> ORGANISM: Mus sp.

<400> SEQUENCE: 488
uccgucucag uuacuuuaua gcc                                          23

<210> SEQ ID NO 489
<211> LENGTH: 21
<212> TYPE: RNA
<213> ORGANISM: Mus sp.

<400> SEQUENCE: 489
ucgaucgguc ggucggucag u                                            21

<210> SEQ ID NO 490
<211> LENGTH: 24
<212> TYPE: RNA
<213> ORGANISM: Mus sp.

<400> SEQUENCE: 490
ucucacacag aaaucgcacc cguc                                         24

<210> SEQ ID NO 491
<211> LENGTH: 23
<212> TYPE: RNA
<213> ORGANISM: Mus sp.

<400> SEQUENCE: 491
ugaucuagcc aaagccugac ugu                                          23

<210> SEQ ID NO 492
<211> LENGTH: 21
<212> TYPE: RNA
<213> ORGANISM: Mus sp.

<400> SEQUENCE: 492
ugcugacccc uaguccagug c                                            21

<210> SEQ ID NO 493
<211> LENGTH: 23
<212> TYPE: RNA
<213> ORGANISM: Mus sp.

<400> SEQUENCE: 493
ugucugcccg agugccugcc ucu                                          23

<210> SEQ ID NO 494
<211> LENGTH: 24
<212> TYPE: RNA
<213> ORGANISM: Mus sp.

<400> SEQUENCE: 494
uucacaaagc ccauacacuu ucac                                         24

<210> SEQ ID NO 495
<211> LENGTH: 22
<212> TYPE: RNA

```
<213> ORGANISM: Mus sp.

<400> SEQUENCE: 495
uauggcuuuu cauuccuaug ug                                              22

<210> SEQ ID NO 496
<211> LENGTH: 22
<212> TYPE: RNA
<213> ORGANISM: Mus sp.

<400> SEQUENCE: 496
uacaguacug ugauagcuga ag                                              22

<210> SEQ ID NO 497
<211> LENGTH: 23
<212> TYPE: RNA
<213> ORGANISM: Mus sp.

<400> SEQUENCE: 497
agcagcauug uacagggcua uca                                             23

<210> SEQ ID NO 498
<211> LENGTH: 23
<212> TYPE: RNA
<213> ORGANISM: Mus sp.

<400> SEQUENCE: 498
uacccuguag auccgaauuu gug                                             23

<210> SEQ ID NO 499
<211> LENGTH: 24
<212> TYPE: RNA
<213> ORGANISM: Mus sp.

<400> SEQUENCE: 499
caaagugcuu acagugcagg uagu                                            24

<210> SEQ ID NO 500
<211> LENGTH: 20
<212> TYPE: RNA
<213> ORGANISM: Mus sp.

<400> SEQUENCE: 500
acugcaguga gggcacuugu                                                 20

<210> SEQ ID NO 501
<211> LENGTH: 23
<212> TYPE: RNA
<213> ORGANISM: Mus sp.

<400> SEQUENCE: 501
ugugcaaauc uaugcaaaac uga                                             23

<210> SEQ ID NO 502
<211> LENGTH: 22
<212> TYPE: RNA
<213> ORGANISM: Mus sp.

<400> SEQUENCE: 502
cauugcacuu gucucggucu ga                                              22

<210> SEQ ID NO 503
<211> LENGTH: 22
```

```
<212> TYPE: RNA
<213> ORGANISM: Mus sp.

<400> SEQUENCE: 503
aaggagcuca cagucuauug ag                                              22

<210> SEQ ID NO 504
<211> LENGTH: 21
<212> TYPE: RNA
<213> ORGANISM: Mus sp.

<400> SEQUENCE: 504
uauugcacau uacuaaguug c                                               21

<210> SEQ ID NO 505
<211> LENGTH: 22
<212> TYPE: RNA
<213> ORGANISM: Mus sp.

<400> SEQUENCE: 505
aacccguaga uccgaacuug ug                                              22

<210> SEQ ID NO 506
<211> LENGTH: 18
<212> TYPE: RNA
<213> ORGANISM: Mus sp.

<400> SEQUENCE: 506
ucuacagugc acgugucu                                                   18

<210> SEQ ID NO 507
<211> LENGTH: 22
<212> TYPE: RNA
<213> ORGANISM: Mus sp.

<400> SEQUENCE: 507
aauacugccg gguaaugaug ga                                              22

<210> SEQ ID NO 508
<211> LENGTH: 21
<212> TYPE: RNA
<213> ORGANISM: Mus sp.

<400> SEQUENCE: 508
cugugcgugu gacagcggcu g                                               21

<210> SEQ ID NO 509
<211> LENGTH: 21
<212> TYPE: RNA
<213> ORGANISM: Mus sp.

<400> SEQUENCE: 509
uaacagucuc cagucacggc c                                               21

<210> SEQ ID NO 510
<211> LENGTH: 22
<212> TYPE: RNA
<213> ORGANISM: Mus sp.

<400> SEQUENCE: 510
accaucgacc guugauugua cc                                              22

<210> SEQ ID NO 511
```

```
<211> LENGTH: 21
<212> TYPE: RNA
<213> ORGANISM: Mus sp.

<400> SEQUENCE: 511
acagcaggca cagacaggca g                                              21

<210> SEQ ID NO 512
<211> LENGTH: 21
<212> TYPE: RNA
<213> ORGANISM: Mus sp.

<400> SEQUENCE: 512
uaaucucagc uggcaacugu g                                              21

<210> SEQ ID NO 513
<211> LENGTH: 21
<212> TYPE: RNA
<213> ORGANISM: Mus sp.

<400> SEQUENCE: 513
uugugcuuga ucuaaccaug u                                              21

<210> SEQ ID NO 514
<211> LENGTH: 21
<212> TYPE: RNA
<213> ORGANISM: Mus sp.

<400> SEQUENCE: 514
ugauugucca aacgcaauuc u                                              21

<210> SEQ ID NO 515
<211> LENGTH: 21
<212> TYPE: RNA
<213> ORGANISM: Mus sp.

<400> SEQUENCE: 515
ugucaguuug ucaaauaccc c                                              21

<210> SEQ ID NO 516
<211> LENGTH: 23
<212> TYPE: RNA
<213> ORGANISM: Mus sp.

<400> SEQUENCE: 516
aaaagcuggg uugagagggc gaa                                            23

<210> SEQ ID NO 517
<211> LENGTH: 21
<212> TYPE: RNA
<213> ORGANISM: Mus sp.

<400> SEQUENCE: 517
uaagccaggg auuguggguu c                                              21

<210> SEQ ID NO 518
<211> LENGTH: 19
<212> TYPE: RNA
<213> ORGANISM: Mus sp.

<400> SEQUENCE: 518
gugcauugua guugcauug                                                 19
```

```
<210> SEQ ID NO 519
<211> LENGTH: 22
<212> TYPE: RNA
<213> ORGANISM: Mus sp.

<400> SEQUENCE: 519
uucccuuugu cauccuuugc cu                                              22

<210> SEQ ID NO 520
<211> LENGTH: 22
<212> TYPE: RNA
<213> ORGANISM: Mus sp.

<400> SEQUENCE: 520
agcuacauug ucugcugggu uu                                              22

<210> SEQ ID NO 521
<211> LENGTH: 23
<212> TYPE: RNA
<213> ORGANISM: Mus sp.

<400> SEQUENCE: 521
agcuacaucu ggcuacuggg ucu                                             23

<210> SEQ ID NO 522
<211> LENGTH: 23
<212> TYPE: RNA
<213> ORGANISM: Mus sp.

<400> SEQUENCE: 522
uaagucacua gugguuccgu uua                                             23

<210> SEQ ID NO 523
<211> LENGTH: 23
<212> TYPE: RNA
<213> ORGANISM: Mus sp.

<400> SEQUENCE: 523
cccaguguuu agacuaccug uuc                                             23

<210> SEQ ID NO 524
<211> LENGTH: 24
<212> TYPE: RNA
<213> ORGANISM: Mus sp.

<400> SEQUENCE: 524
aacauucauu gcugucggug gguu                                            24

<210> SEQ ID NO 525
<211> LENGTH: 22
<212> TYPE: RNA
<213> ORGANISM: Mus sp.

<400> SEQUENCE: 525
aacauucaac cugucgguga gu                                              22

<210> SEQ ID NO 526
<211> LENGTH: 22
<212> TYPE: RNA
<213> ORGANISM: Mus sp.

<400> SEQUENCE: 526
ucacagugaa ccggucucuu uc                                              22
```

```
<210> SEQ ID NO 527
<211> LENGTH: 21
<212> TYPE: RNA
<213> ORGANISM: Mus sp.

<400> SEQUENCE: 527
uggaagacua gugauuugu u                                           21

<210> SEQ ID NO 528
<211> LENGTH: 21
<212> TYPE: RNA
<213> ORGANISM: Mus sp.

<400> SEQUENCE: 528
uggaagacuu gugauuuugu u                                          21

<210> SEQ ID NO 529
<211> LENGTH: 24
<212> TYPE: RNA
<213> ORGANISM: Mus sp.

<400> SEQUENCE: 529
uacugcauca ggaacugacu ggau                                       24

<210> SEQ ID NO 530
<211> LENGTH: 21
<212> TYPE: RNA
<213> ORGANISM: Mus sp.

<400> SEQUENCE: 530 uuggucccu ucaaccagcu a                                           21

<210> SEQ ID NO 531
<211> LENGTH: 21
<212> TYPE: RNA
<213> ORGANISM: Mus sp.

<400> SEQUENCE: 531
augaccuaug auuugacaga c                                          21

<210> SEQ ID NO 532
<211> LENGTH: 22
<212> TYPE: RNA
<213> ORGANISM: Drosophila sp.

<400> SEQUENCE: 532
uggaauguaa agaaguaugg ag                                         22

<210> SEQ ID NO 533
<211> LENGTH: 23
<212> TYPE: RNA
<213> ORGANISM: Drosophila sp.

<400> SEQUENCE: 533
uaucacagcc agcuuugaug agc                                        23

<210> SEQ ID NO 534
<211> LENGTH: 23
<212> TYPE: RNA
<213> ORGANISM: Drosophila sp.

<400> SEQUENCE: 534
uaucacagcc agcuuugagg agc                                        23
```

```
<210> SEQ ID NO 535
<211> LENGTH: 22
<212> TYPE: RNA
<213> ORGANISM: Drosophila sp.

<400> SEQUENCE: 535
ucacugggca aaguguqucu ca                                        22

<210> SEQ ID NO 536
<211> LENGTH: 21
<212> TYPE: RNA
<213> ORGANISM: Drosophila sp.

<400> SEQUENCE: 536
auaaagcuag acaaccauug a                                         21

<210> SEQ ID NO 537
<211> LENGTH: 23
<212> TYPE: RNA
<213> ORGANISM: Drosophila sp.

<400> SEQUENCE: 537
aaaggaacga ucguugugau aug                                       23

<210> SEQ ID NO 538
<211> LENGTH: 22
<212> TYPE: RNA
<213> ORGANISM: Drosophila sp.

<400> SEQUENCE: 538
uaucacagug gcuguucuuu uu                                        22

<210> SEQ ID NO 539
<211> LENGTH: 23
<212> TYPE: RNA
<213> ORGANISM: Drosophila sp.

<400> SEQUENCE: 539
uggaagacua gugauuuugu ugu                                       23

<210> SEQ ID NO 540
<211> LENGTH: 23
<212> TYPE: RNA
<213> ORGANISM: Drosophila sp.

<400> SEQUENCE: 540
uaauacuguc agguaaagau guc                                       23

<210> SEQ ID NO 541
<211> LENGTH: 23
<212> TYPE: RNA
<213> ORGANISM: Drosophila sp.

<400> SEQUENCE: 541
ucuuugguua ucuagcugua uga                                       23

<210> SEQ ID NO 542
<211> LENGTH: 21
<212> TYPE: RNA
<213> ORGANISM: Drosophila sp.

<400> SEQUENCE: 542
```
acccuguaga uccgaauuug u                                           21

<210> SEQ ID NO 543
<211> LENGTH: 21
<212> TYPE: RNA
<213> ORGANISM: Drosophila sp.

<400> SEQUENCE: 543
caucacaguc ugaguucuug c                                           21

<210> SEQ ID NO 544
<211> LENGTH: 23
<212> TYPE: RNA
<213> ORGANISM: Drosophila sp.

<400> SEQUENCE: 544
ugaguauuac aucagguacu ggu                                         23

<210> SEQ ID NO 545
<211> LENGTH: 22
<212> TYPE: RNA
<213> ORGANISM: Drosophila sp.

<400> SEQUENCE: 545
uaucacagcc auuuugauga gu                                          22

<210> SEQ ID NO 546
<211> LENGTH: 22
<212> TYPE: RNA
<213> ORGANISM: Drosophila sp.

<400> SEQUENCE: 546
uaucacagcc auuuugacga gu                                          22

<210> SEQ ID NO 547
<211> LENGTH: 21
<212> TYPE: RNA
<213> ORGANISM: Drosophila sp.

<400> SEQUENCE: 547
ucagucuuuu ucucucuccu a                                           21

<210> SEQ ID NO 548
<211> LENGTH: 24
<212> TYPE: RNA
<213> ORGANISM: Drosophila sp.

<400> SEQUENCE: 548
guuaauggca cuggaagaau ucac                                        24

<210> SEQ ID NO 549
<211> LENGTH: 21
<212> TYPE: RNA
<213> ORGANISM: Drosophila sp.

<400> SEQUENCE: 549
ccuuaucauu cucucgcccc g                                           21

<210> SEQ ID NO 550
<211> LENGTH: 22
<212> TYPE: RNA
<213> ORGANISM: Drosophila sp.

<400> SEQUENCE: 550
uggacggaga acugauaagg gc                                            22

<210> SEQ ID NO 551
<211> LENGTH: 26
<212> TYPE: RNA
<213> ORGANISM: Drosophila sp.

<400> SEQUENCE: 551
uuuugugacc gacacuaacg gguaau                                        26

<210> SEQ ID NO 552
<211> LENGTH: 23
<212> TYPE: RNA
<213> ORGANISM: Drosophila sp.

<400> SEQUENCE: 552
ucagguaccu gaaguagcgc gcg                                           23

<210> SEQ ID NO 553
<211> LENGTH: 22
<212> TYPE: RNA
<213> ORGANISM: Drosophila sp.

<400> SEQUENCE: 553
cauugcacuu gucccggccu au                                            22

<210> SEQ ID NO 554
<211> LENGTH: 23
<212> TYPE: RNA
<213> ORGANISM: Drosophila sp.

<400> SEQUENCE: 554
ugauugucca aacgcaauuc uug                                           23

<210> SEQ ID NO 555
<211> LENGTH: 23
<212> TYPE: RNA
<213> ORGANISM: Drosophila sp.

<400> SEQUENCE: 555
cagcgaggua uagaguuccu acg                                           23

<210> SEQ ID NO 556
<211> LENGTH: 22
<212> TYPE: RNA
<213> ORGANISM: Drosophila sp.

<400> SEQUENCE: 556
uaggaacuuc auaccgugcu cu                                            22

<210> SEQ ID NO 557
<211> LENGTH: 23
<212> TYPE: RNA
<213> ORGANISM: Drosophila sp.

<400> SEQUENCE: 557
uaaaugcacu aucugguacg aca                                           23

<210> SEQ ID NO 558
<211> LENGTH: 22
<212> TYPE: RNA
<213> ORGANISM: Drosophila sp.

```
<400> SEQUENCE: 558 ucgguggac uuucguccgu uu                                    22

<210> SEQ ID NO 559
<211> LENGTH: 22
<212> TYPE: RNA
<213> ORGANISM: Drosophila sp.

<400> SEQUENCE: 559 uuggucccu ucaaccagcu gu                                    22

<210> SEQ ID NO 560
<211> LENGTH: 22
<212> TYPE: RNA
<213> ORGANISM: Drosophila sp.

<400> SEQUENCE: 560
ugacuagauc cacacucauu aa                                   22

<210> SEQ ID NO 561
<211> LENGTH: 21
<212> TYPE: RNA
<213> ORGANISM: Drosophila sp.

<400> SEQUENCE: 561
aggugcauug uagucgcauu g                                    21

<210> SEQ ID NO 562
<211> LENGTH: 27
<212> TYPE: RNA
<213> ORGANISM: Drosophila sp.

<400> SEQUENCE: 562
uguauuuacg uugcauauga aaugaua                              27

<210> SEQ ID NO 563
<211> LENGTH: 22
<212> TYPE: RNA
<213> ORGANISM: Drosophila sp.

<400> SEQUENCE: 563
aagagagcug uccgucgaca gu                                   22

<210> SEQ ID NO 564
<211> LENGTH: 23
<212> TYPE: RNA
<213> ORGANISM: Drosophila sp.

<400> SEQUENCE: 564
ugucauggaa uugcucucuu ugu                                  23

<210> SEQ ID NO 565
<211> LENGTH: 28
<212> TYPE: RNA
<213> ORGANISM: Drosophila sp.

<400> SEQUENCE: 565
aaucuagccu cuacuaggcu uugucugu                             28

<210> SEQ ID NO 566
<211> LENGTH: 21
<212> TYPE: RNA
<213> ORGANISM: Drosophila sp.
```

-continued

```
<400> SEQUENCE: 566
uaaauaucag cugguaauuc u                                              21

<210> SEQ ID NO 567
<211> LENGTH: 29
<212> TYPE: RNA
<213> ORGANISM: Drosophila sp.

<400> SEQUENCE: 567
ugaagucagc aacuugauuc cagcaauug                                      29

<210> SEQ ID NO 568
<211> LENGTH: 22
<212> TYPE: RNA
<213> ORGANISM: Drosophila sp.

<400> SEQUENCE: 568
aagagagcua uccgucgaca gu                                             22

<210> SEQ ID NO 569
<211> LENGTH: 22
<212> TYPE: RNA
<213> ORGANISM: Drosophila sp.

<400> SEQUENCE: 569
uggcagugug guuagcuggu ug                                             22

<210> SEQ ID NO 570
<211> LENGTH: 23
<212> TYPE: RNA
<213> ORGANISM: Drosophila sp.

<400> SEQUENCE: 570
uaaggcacgc ggugaaugcc aag                                            23

<210> SEQ ID NO 571
<211> LENGTH: 22
<212> TYPE: RNA
<213> ORGANISM: Drosophila sp.

<400> SEQUENCE: 571
uaaagcuaga uuaccaaagc au                                             22

<210> SEQ ID NO 572
<211> LENGTH: 23
<212> TYPE: RNA
<213> ORGANISM: Drosophila sp.

<400> SEQUENCE: 572
cagcgaggua uagaguuccu acg                                            23

<210> SEQ ID NO 573
<211> LENGTH: 22
<212> TYPE: RNA
<213> ORGANISM: Drosophila sp.

<400> SEQUENCE: 573
uaggaacuua auaccgugcu cu                                             22

<210> SEQ ID NO 574
<211> LENGTH: 21
<212> TYPE: RNA
```

```
<213> ORGANISM: Drosophila sp.

<400> SEQUENCE: 574
uugugcgugu gacagcggcu a                                           21

<210> SEQ ID NO 575
<211> LENGTH: 22
<212> TYPE: RNA
<213> ORGANISM: Drosophila sp.

<400> SEQUENCE: 575
uagcaccauu cgaaaucagu gc                                          22

<210> SEQ ID NO 576
<211> LENGTH: 22
<212> TYPE: RNA
<213> ORGANISM: Drosophila sp.

<400> SEQUENCE: 576
aacccguaaa uccgaacuug ug                                          22

<210> SEQ ID NO 577
<211> LENGTH: 22
<212> TYPE: RNA
<213> ORGANISM: Drosophila sp.

<400> SEQUENCE: 577
aauugcacua gucccggccu gc                                          22

<210> SEQ ID NO 578
<211> LENGTH: 23
<212> TYPE: RNA
<213> ORGANISM: Drosophila sp.

<400> SEQUENCE: 578
ugacuagacc gaacacucgu gcu                                         23

<210> SEQ ID NO 579
<211> LENGTH: 21
<212> TYPE: RNA
<213> ORGANISM: Drosophila sp.

<400> SEQUENCE: 579
uguguugaaa aucguuugca c                                           21

<210> SEQ ID NO 580
<211> LENGTH: 21
<212> TYPE: RNA
<213> ORGANISM: Drosophila sp.

<400> SEQUENCE: 580
uugagcaaaa uuucaggugu g                                           21

<210> SEQ ID NO 581
<211> LENGTH: 21
<212> TYPE: RNA
<213> ORGANISM: Drosophila sp.

<400> SEQUENCE: 581
cuuggcacug ggagaauuca c                                           21

<210> SEQ ID NO 582
<211> LENGTH: 23
```

```
<212> TYPE: RNA
<213> ORGANISM: Drosophila sp.

<400> SEQUENCE: 582
uuucaugucg auuucauuuc aug                                          23

<210> SEQ ID NO 583
<211> LENGTH: 26
<212> TYPE: RNA
<213> ORGANISM: Drosophila sp.

<400> SEQUENCE: 583
uaaauauuua aguggagccu gcgacu                                       26

<210> SEQ ID NO 584
<211> LENGTH: 23
<212> TYPE: RNA
<213> ORGANISM: Drosophila sp.

<400> SEQUENCE: 584
ugagaucauu uugaaagcug auu                                          23

<210> SEQ ID NO 585
<211> LENGTH: 23
<212> TYPE: RNA
<213> ORGANISM: Drosophila sp.

<400> SEQUENCE: 585
uuuagguuuc acaggaaacu ggu                                          23

<210> SEQ ID NO 586
<211> LENGTH: 22
<212> TYPE: RNA
<213> ORGANISM: Drosophila sp.

<400> SEQUENCE: 586
uggcaagaug ucggaauagc ug                                           22

<210> SEQ ID NO 587
<211> LENGTH: 23
<212> TYPE: RNA
<213> ORGANISM: Drosophila sp.

<400> SEQUENCE: 587
uaaucucaau uuguaaaugu gag                                          23

<210> SEQ ID NO 588
<211> LENGTH: 23
<212> TYPE: RNA
<213> ORGANISM: Drosophila sp.

<400> SEQUENCE: 588
auuguacuuc aucaggugcu cug                                          23

<210> SEQ ID NO 589
<211> LENGTH: 22
<212> TYPE: RNA
<213> ORGANISM: Drosophila sp.

<400> SEQUENCE: 589
ucuuugguau ucuagcugua ga                                           22

<210> SEQ ID NO 590
```

```
<211> LENGTH: 22
<212> TYPE: RNA
<213> ORGANISM: Drosophila sp.

<400> SEQUENCE: 590
ucagguacuu agugacucuc aa                                              22

<210> SEQ ID NO 591
<211> LENGTH: 22
<212> TYPE: RNA
<213> ORGANISM: Drosophila sp.

<400> SEQUENCE: 591
gggggucacu cugugccugu gc                                              22

<210> SEQ ID NO 592
<211> LENGTH: 23
<212> TYPE: RNA
<213> ORGANISM: Drosophila sp.

<400> SEQUENCE: 592
ucuuggguga uuuuagcugu aug                                             23

<210> SEQ ID NO 593
<211> LENGTH: 21
<212> TYPE: RNA
<213> ORGANISM: Drosophila sp.

<400> SEQUENCE: 593
ugagguagua gguuguauag u                                               21

<210> SEQ ID NO 594
<211> LENGTH: 22
<212> TYPE: RNA
<213> ORGANISM: Drosophila sp.

<400> SEQUENCE: 594
ucccugagac ccuaacuugu ga                                              22

<210> SEQ ID NO 595
<211> LENGTH: 20
<212> TYPE: RNA
<213> ORGANISM: Drosophila sp.

<400> SEQUENCE: 595
ucacaaccuc cuugagugag                                                 20

<210> SEQ ID NO 596
<211> LENGTH: 22
<212> TYPE: RNA
<213> ORGANISM: Drosophila sp.

<400> SEQUENCE: 596
aaucacagga uuauacugug ag                                              22

<210> SEQ ID NO 597
<211> LENGTH: 23
<212> TYPE: RNA
<213> ORGANISM: Drosophila sp.

<400> SEQUENCE: 597
uggcaagaug ucggcauagc uga                                             23
```

```
<210> SEQ ID NO 598
<211> LENGTH: 22
<212> TYPE: RNA
<213> ORGANISM: Drosophila sp.

<400> SEQUENCE: 598
gcacugggua aaguuugucc ua                                           22

<210> SEQ ID NO 599
<211> LENGTH: 22
<212> TYPE: RNA
<213> ORGANISM: Drosophila sp.

<400> SEQUENCE: 599
uauugcacac uucccggccu uu                                           22

<210> SEQ ID NO 600
<211> LENGTH: 22
<212> TYPE: RNA
<213> ORGANISM: Drosophila sp.

<400> SEQUENCE: 600
uauugcacau ucaccggccu ga                                           22

<210> SEQ ID NO 601
<211> LENGTH: 22
<212> TYPE: RNA
<213> ORGANISM: Drosophila sp.

<400> SEQUENCE: 601
uauugcacuu gagacggccu ga                                           22

<210> SEQ ID NO 602
<211> LENGTH: 22
<212> TYPE: RNA
<213> ORGANISM: Drosophila sp.

<400> SEQUENCE: 602
uauugcacuu uucacagccc ga                                           22

<210> SEQ ID NO 603
<211> LENGTH: 21
<212> TYPE: RNA
<213> ORGANISM: Drosophila sp.

<400> SEQUENCE: 603
uauucgagcc aauaaguucg g                                            21

<210> SEQ ID NO 604
<211> LENGTH: 22
<212> TYPE: RNA
<213> ORGANISM: Drosophila sp.

<400> SEQUENCE: 604
uuuugauugu ugcucagaaa gc                                           22

<210> SEQ ID NO 605
<211> LENGTH: 22
<212> TYPE: RNA
<213> ORGANISM: Drosophila sp.

<400> SEQUENCE: 605
ugucuuuuuc cgcuuacugg cg                                           22
```

<210> SEQ ID NO 606
<211> LENGTH: 24
<212> TYPE: RNA
<213> ORGANISM: Drosophila sp.

<400> SEQUENCE: 606
ugaacacagc uggugguauc cagu                                              24

<210> SEQ ID NO 607
<211> LENGTH: 22
<212> TYPE: RNA
<213> ORGANISM: Drosophila sp.

<400> SEQUENCE: 607
ucacugggcu uuguuuaucu ca                                                22

<210> SEQ ID NO 608
<211> LENGTH: 23
<212> TYPE: RNA
<213> ORGANISM: Drosophila sp.

<400> SEQUENCE: 608
uaucacagcc agcuuugaug ggc                                               23

<210> SEQ ID NO 609
<211> LENGTH: 22
<212> TYPE: RNA
<213> ORGANISM: Drosophila sp.

<400> SEQUENCE: 609
acguauacug aauguauccu ga                                                22

<210> SEQ ID NO 610
<211> LENGTH: 24
<212> TYPE: RNA
<213> ORGANISM: Drosophila sp.

<400> SEQUENCE: 610
cgguauaccu ucaguauacg uaac                                              24

<210> SEQ ID NO 611
<211> LENGTH: 20
<212> TYPE: RNA
<213> ORGANISM: Rattus sp.

<400> SEQUENCE: 611
aaacaugaag cgcugcaaca                                                   20

<210> SEQ ID NO 612
<211> LENGTH: 22
<212> TYPE: RNA
<213> ORGANISM: Rattus sp.

<400> SEQUENCE: 612
gcacauuaca cggucgaccu cu                                                22

<210> SEQ ID NO 613
<211> LENGTH: 25
<212> TYPE: RNA
<213> ORGANISM: Rattus sp.

<400> SEQUENCE: 613
cagugcaaua guauugucaa agcau                                             25

<210> SEQ ID NO 614
<211> LENGTH: 23
<212> TYPE: RNA
<213> ORGANISM: Rattus sp.

<400> SEQUENCE: 614 cgcaucccu agggcauugg ugu                                    23

<210> SEQ ID NO 615
<211> LENGTH: 22
<212> TYPE: RNA
<213> ORGANISM: Rattus sp.

<400> SEQUENCE: 615
ccacugcccc aggugcugcu gg                                    22

<210> SEQ ID NO 616
<211> LENGTH: 23
<212> TYPE: RNA
<213> ORGANISM: Rattus sp.

<400> SEQUENCE: 616
ccuaguaggu gcucaguaag ugu                                   23

<210> SEQ ID NO 617
<211> LENGTH: 21
<212> TYPE: RNA
<213> ORGANISM: Rattus sp.

<400> SEQUENCE: 617
ccucugggcc cuuccuccag u                                     21

<210> SEQ ID NO 618
<211> LENGTH: 21
<212> TYPE: RNA
<213> ORGANISM: Rattus sp.

<400> SEQUENCE: 618
agagguagua gguugcauag u                                     21

<210> SEQ ID NO 619
<211> LENGTH: 22
<212> TYPE: RNA
<213> ORGANISM: Rattus sp.

<400> SEQUENCE: 619
cuauacgacc ugcugccuuu cu                                    22

<210> SEQ ID NO 620
<211> LENGTH: 22
<212> TYPE: RNA
<213> ORGANISM: Rattus sp.

<400> SEQUENCE: 620
cuggcccucu cugcccuucc gu                                    22

<210> SEQ ID NO 621
<211> LENGTH: 22
<212> TYPE: RNA
<213> ORGANISM: Rattus sp.

<400> SEQUENCE: 621
aacacaccca gcuaaccuuu uu                                        22

<210> SEQ ID NO 622
<211> LENGTH: 23
<212> TYPE: RNA
<213> ORGANISM: Rattus sp.

<400> SEQUENCE: 622
gcaaagcaca gggccugcag aga                                       23

<210> SEQ ID NO 623
<211> LENGTH: 21
<212> TYPE: RNA
<213> ORGANISM: Rattus sp.

<400> SEQUENCE: 623
gccccugggc cuauccuaga a                                         21

<210> SEQ ID NO 624
<211> LENGTH: 20
<212> TYPE: RNA
<213> ORGANISM: Rattus sp.

<400> SEQUENCE: 624
guggugugcu aguuacuuuu                                           20

<210> SEQ ID NO 625
<211> LENGTH: 21
<212> TYPE: RNA
<213> ORGANISM: Rattus sp.

<400> SEQUENCE: 625
agugguuuua cccuauggua g                                         21

<210> SEQ ID NO 626
<211> LENGTH: 24
<212> TYPE: RNA
<213> ORGANISM: Rattus sp.

<400> SEQUENCE: 626
uaccacaggg uagaaccacg gaca                                      24

<210> SEQ ID NO 627
<211> LENGTH: 21
<212> TYPE: RNA
<213> ORGANISM: Rattus sp.

<400> SEQUENCE: 627
ucacccuucc auaucuaguc u                                         21

<210> SEQ ID NO 628
<211> LENGTH: 23
<212> TYPE: RNA
<213> ORGANISM: Rattus sp.

<400> SEQUENCE: 628
uucagcuccu auaugaugcc uuu                                       23

<210> SEQ ID NO 629
<211> LENGTH: 22
<212> TYPE: RNA
<213> ORGANISM: Rattus sp.

<400> SEQUENCE: 629
ucagugcauc acagaacuuu gu                                    22

<210> SEQ ID NO 630
<211> LENGTH: 23
<212> TYPE: RNA
<213> ORGANISM: Rattus sp.

<400> SEQUENCE: 630
uccagcauca gugauuuugu uga                                   23

<210> SEQ ID NO 631
<211> LENGTH: 21
<212> TYPE: RNA
<213> ORGANISM: Rattus sp.

<400> SEQUENCE: 631
ucccuguccu ccaggagcuc a                                     21

<210> SEQ ID NO 632
<211> LENGTH: 21
<212> TYPE: RNA
<213> ORGANISM: Rattus sp.

<400> SEQUENCE: 632
ucgaucgguc ggucggucag u                                     21

<210> SEQ ID NO 633
<211> LENGTH: 24
<212> TYPE: RNA
<213> ORGANISM: Rattus sp.

<400> SEQUENCE: 633
ucucacacag aaaucgcacc cguc                                  24

<210> SEQ ID NO 634
<211> LENGTH: 23
<212> TYPE: RNA
<213> ORGANISM: Rattus sp.

<400> SEQUENCE: 634
ugaucuagcc aaagccugac cgu                                   23

<210> SEQ ID NO 635
<211> LENGTH: 21
<212> TYPE: RNA
<213> ORGANISM: Rattus sp.

<400> SEQUENCE: 635
ugcugacccc uaguccagug c                                     21

<210> SEQ ID NO 636
<211> LENGTH: 23
<212> TYPE: RNA
<213> ORGANISM: Rattus sp.

<400> SEQUENCE: 636
ugucugccug agugccugcc ucu                                   23

<210> SEQ ID NO 637
<211> LENGTH: 22
<212> TYPE: RNA
<213> ORGANISM: Rattus sp.

```
<400> SEQUENCE: 637
cagcccugcu gucuuaaccu cu                                              22

<210> SEQ ID NO 638
<211> LENGTH: 22
<212> TYPE: RNA
<213> ORGANISM: Rattus sp.

<400> SEQUENCE: 638
cuuuuugcgg ucugggcuug cu                                              22

<210> SEQ ID NO 639
<211> LENGTH: 22
<212> TYPE: RNA
<213> ORGANISM: Rattus sp.

<400> SEQUENCE: 639
aagcccuuac cccaaaaagc au                                              22

<210> SEQ ID NO 640
<211> LENGTH: 23
<212> TYPE: RNA
<213> ORGANISM: Rattus sp.

<400> SEQUENCE: 640
uaaagugcuu auagugcagg uag                                             23

<210> SEQ ID NO 641
<211> LENGTH: 21
<212> TYPE: RNA
<213> ORGANISM: Rattus sp.

<400> SEQUENCE: 641
acugcauuac gagcacuuac a                                               21

<210> SEQ ID NO 642
<211> LENGTH: 24
<212> TYPE: RNA
<213> ORGANISM: Rattus sp.

<400> SEQUENCE: 642
uucacaaagc ccauacacuu ucac                                            24

<210> SEQ ID NO 643
<211> LENGTH: 21
<212> TYPE: RNA
<213> ORGANISM: Rattus sp.

<400> SEQUENCE: 643
uggaagacua gugauuuugu u                                               21

<210> SEQ ID NO 644
<211> LENGTH: 22
<212> TYPE: RNA
<213> ORGANISM: Rattus sp.

<400> SEQUENCE: 644
caacaaauca cagucugcca ua                                              22

<210> SEQ ID NO 645
<211> LENGTH: 24
<212> TYPE: RNA
<213> ORGANISM: Rattus sp.
```

-continued

```
<400> SEQUENCE: 645
ucccugagga gcccuuugag ccug                                          24

<210> SEQ ID NO 646
<211> LENGTH: 22
<212> TYPE: RNA
<213> ORGANISM: Rattus sp.

<400> SEQUENCE: 646
uauggcuuuu cauuccuaug ug                                            22

<210> SEQ ID NO 647
<211> LENGTH: 22
<212> TYPE: RNA
<213> ORGANISM: Rattus sp.

<400> SEQUENCE: 647
ucgaggagcu cacagucuag ua                                            22

<210> SEQ ID NO 648
<211> LENGTH: 22
<212> TYPE: RNA
<213> ORGANISM: Rattus sp.

<400> SEQUENCE: 648
acuagacuga ggcuccuuga gg                                            22

<210> SEQ ID NO 649
<211> LENGTH: 22
<212> TYPE: RNA
<213> ORGANISM: Rattus sp.

<400> SEQUENCE: 649
uacaguacug ugauagcuga ag                                            22

<210> SEQ ID NO 650
<211> LENGTH: 22
<212> TYPE: RNA
<213> ORGANISM: Rattus sp.

<400> SEQUENCE: 650
ugagguagua gguuguauag uu                                            22

<210> SEQ ID NO 651
<211> LENGTH: 22
<212> TYPE: RNA
<213> ORGANISM: Rattus sp.

<400> SEQUENCE: 651
ugagguagua gguugugugg uu                                            22

<210> SEQ ID NO 652
<211> LENGTH: 22
<212> TYPE: RNA
<213> ORGANISM: Rattus sp.

<400> SEQUENCE: 652
ugagguagua gguuguaugg uu                                            22

<210> SEQ ID NO 653
<211> LENGTH: 21
<212> TYPE: RNA
```

-continued

```
<213> ORGANISM: Rattus sp.

<400> SEQUENCE: 653
ugagguagga gguuguauag u                                              21

<210> SEQ ID NO 654
<211> LENGTH: 22
<212> TYPE: RNA
<213> ORGANISM: Rattus sp.

<400> SEQUENCE: 654
ugagguagua gauuguauag uu                                             22

<210> SEQ ID NO 655
<211> LENGTH: 19
<212> TYPE: RNA
<213> ORGANISM: Rattus sp.

<400> SEQUENCE: 655
ugagguagua guuugugcu                                                 19

<210> SEQ ID NO 656
<211> LENGTH: 21
<212> TYPE: RNA
<213> ORGANISM: Rattus sp.

<400> SEQUENCE: 656
uggaagacuu gugauuuugu u                                              21

<210> SEQ ID NO 657
<211> LENGTH: 23
<212> TYPE: RNA
<213> ORGANISM: Rattus sp.

<400> SEQUENCE: 657
ucuuugguua ucuagcugua uga                                            23

<210> SEQ ID NO 658
<211> LENGTH: 23
<212> TYPE: RNA
<213> ORGANISM: Rattus sp.

<400> SEQUENCE: 658
uacccuguag auccgaauuu gug                                            23

<210> SEQ ID NO 659
<211> LENGTH: 22
<212> TYPE: RNA
<213> ORGANISM: Rattus sp.

<400> SEQUENCE: 659
uacccuguag aaccgaauuu gu                                             22

<210> SEQ ID NO 660
<211> LENGTH: 22
<212> TYPE: RNA
<213> ORGANISM: Rattus sp.

<400> SEQUENCE: 660
uagcagcaca ucaugguuua ca                                             22

<210> SEQ ID NO 661
<211> LENGTH: 22
```

```
<212> TYPE: RNA
<213> ORGANISM: Rattus sp.

<400> SEQUENCE: 661
uagcagcacg uaaauauugg cg                                      22

<210> SEQ ID NO 662
<211> LENGTH: 24
<212> TYPE: RNA
<213> ORGANISM: Rattus sp.

<400> SEQUENCE: 662
caaagugcuu acagucagg uagu                                     24

<210> SEQ ID NO 663
<211> LENGTH: 22
<212> TYPE: RNA
<213> ORGANISM: Rattus sp.

<400> SEQUENCE: 663
uaaggugcau cuagugcaga ua                                      22

<210> SEQ ID NO 664
<211> LENGTH: 23
<212> TYPE: RNA
<213> ORGANISM: Rattus sp.

<400> SEQUENCE: 664
ugugcaaauc caugcaaaac uga                                     23

<210> SEQ ID NO 665
<211> LENGTH: 23
<212> TYPE: RNA
<213> ORGANISM: Rattus sp.

<400> SEQUENCE: 665
ugugcaaauc uaugcaaaac uga                                     23

<210> SEQ ID NO 666
<211> LENGTH: 22
<212> TYPE: RNA
<213> ORGANISM: Rattus sp.

<400> SEQUENCE: 666
uagcuuauca gacugauguu ga                                      22

<210> SEQ ID NO 667
<211> LENGTH: 22
<212> TYPE: RNA
<213> ORGANISM: Rattus sp.

<400> SEQUENCE: 667
aagcugccag uugaagaacu gu                                      22

<210> SEQ ID NO 668
<211> LENGTH: 21
<212> TYPE: RNA
<213> ORGANISM: Rattus sp.

<400> SEQUENCE: 668
aucacauugc cagggauuuc c                                       21

<210> SEQ ID NO 669
```

```
<211> LENGTH: 23
<212> TYPE: RNA
<213> ORGANISM: Rattus sp.

<400> SEQUENCE: 669
aucacauugc cagggauuac cac                                              23

<210> SEQ ID NO 670
<211> LENGTH: 22
<212> TYPE: RNA
<213> ORGANISM: Rattus sp.

<400> SEQUENCE: 670
uggcucaguu cagcaggaac ag                                               22

<210> SEQ ID NO 671
<211> LENGTH: 22
<212> TYPE: RNA
<213> ORGANISM: Rattus sp.

<400> SEQUENCE: 671
cauugcacuu gucucggucu ga                                               22

<210> SEQ ID NO 672
<211> LENGTH: 22
<212> TYPE: RNA
<213> ORGANISM: Rattus sp.

<400> SEQUENCE: 672
uucaaguaau ccaggauagg cu                                               22

<210> SEQ ID NO 673
<211> LENGTH: 22
<212> TYPE: RNA
<213> ORGANISM: Rattus sp.

<400> SEQUENCE: 673
uucaaguaau ucaggauagg uu                                               22

<210> SEQ ID NO 674
<211> LENGTH: 20
<212> TYPE: RNA
<213> ORGANISM: Rattus sp.

<400> SEQUENCE: 674
uucacagugg cuaaguucug                                                  20

<210> SEQ ID NO 675
<211> LENGTH: 21
<212> TYPE: RNA
<213> ORGANISM: Rattus sp.

<400> SEQUENCE: 675
uucacagugg cuaaguuccg c                                                21

<210> SEQ ID NO 676
<211> LENGTH: 22
<212> TYPE: RNA
<213> ORGANISM: Rattus sp.

<400> SEQUENCE: 676
aaggagcuca cagucuauug ag                                               22
```

```
<210> SEQ ID NO 677
<211> LENGTH: 22
<212> TYPE: RNA
<213> ORGANISM: Rattus sp.

<400> SEQUENCE: 677
uagcaccauu ugaaaucagu gu                                              22

<210> SEQ ID NO 678
<211> LENGTH: 22
<212> TYPE: RNA
<213> ORGANISM: Rattus sp.

<400> SEQUENCE: 678
cuagcaccau cugaaaucgg uu                                              22

<210> SEQ ID NO 679
<211> LENGTH: 22
<212> TYPE: RNA
<213> ORGANISM: Rattus sp.

<400> SEQUENCE: 679
uagcaccauu ugaaaucggu ua                                              22

<210> SEQ ID NO 680
<211> LENGTH: 23
<212> TYPE: RNA
<213> ORGANISM: Rattus sp.

<400> SEQUENCE: 680
uguaaacauc cuacacucuc agc                                             23

<210> SEQ ID NO 681
<211> LENGTH: 20
<212> TYPE: RNA
<213> ORGANISM: Rattus sp.

<400> SEQUENCE: 681
uguaaacauc cuugacugga                                                 20

<210> SEQ ID NO 682
<211> LENGTH: 21
<212> TYPE: RNA
<213> ORGANISM: Rattus sp.

<400> SEQUENCE: 682
uguaaacauc cuacacucag c                                               21

<210> SEQ ID NO 683
<211> LENGTH: 22
<212> TYPE: RNA
<213> ORGANISM: Rattus sp.

<400> SEQUENCE: 683
uguaaacauc cccgacugga ag                                              22

<210> SEQ ID NO 684
<211> LENGTH: 22
<212> TYPE: RNA
<213> ORGANISM: Rattus sp.

<400> SEQUENCE: 684
cuuucagucg gauguuugca gc                                              22
```

<210> SEQ ID NO 685
<211> LENGTH: 22
<212> TYPE: RNA
<213> ORGANISM: Rattus sp.

<400> SEQUENCE: 685
aggcaagaug cuggcauagc ug                                    22

<210> SEQ ID NO 686
<211> LENGTH: 21
<212> TYPE: RNA
<213> ORGANISM: Rattus sp.

<400> SEQUENCE: 686
uauugcacau uacuaaguug c                                     21

<210> SEQ ID NO 687
<211> LENGTH: 19
<212> TYPE: RNA
<213> ORGANISM: Rattus sp.

<400> SEQUENCE: 687
gugcauugua guugcauug                                        19

<210> SEQ ID NO 688
<211> LENGTH: 23
<212> TYPE: RNA
<213> ORGANISM: Rattus sp.

<400> SEQUENCE: 688
uaggcagugu aauuagcuga uug                                   23

<210> SEQ ID NO 689
<211> LENGTH: 23
<212> TYPE: RNA
<213> ORGANISM: Rattus sp.

<400> SEQUENCE: 689
aggcagugua guuagcugau ugc                                   23

<210> SEQ ID NO 690
<211> LENGTH: 23
<212> TYPE: RNA
<213> ORGANISM: Rattus sp.

<400> SEQUENCE: 690
uggcaguguc uuagcugguu guu                                   23

<210> SEQ ID NO 691
<211> LENGTH: 21
<212> TYPE: RNA
<213> ORGANISM: Rattus sp.

<400> SEQUENCE: 691
uauugcacuu gucccggccu g                                     21

<210> SEQ ID NO 692
<211> LENGTH: 23
<212> TYPE: RNA
<213> ORGANISM: Rattus sp.

<400> SEQUENCE: 692
caaagugcug uucgugcagg uag                                   23

<210> SEQ ID NO 693
<211> LENGTH: 23
<212> TYPE: RNA
<213> ORGANISM: Rattus sp.

<400> SEQUENCE: 693
uuuggcacua gcacauuuuu gcu                                           23

<210> SEQ ID NO 694
<211> LENGTH: 22
<212> TYPE: RNA
<213> ORGANISM: Rattus sp.

<400> SEQUENCE: 694
ugagguagua aguuguauug uu                                            22

<210> SEQ ID NO 695
<211> LENGTH: 22
<212> TYPE: RNA
<213> ORGANISM: Rattus sp.

<400> SEQUENCE: 695
aacccguaga uccgaucuug ug                                            22

<210> SEQ ID NO 696
<211> LENGTH: 22
<212> TYPE: RNA
<213> ORGANISM: Rattus sp.

<400> SEQUENCE: 696
cacccguaga accgaccuug cg                                            22

<210> SEQ ID NO 697
<211> LENGTH: 22
<212> TYPE: RNA
<213> ORGANISM: Rattus sp.

<400> SEQUENCE: 697
aacccguaga uccgaacuug ug                                            22

<210> SEQ ID NO 698
<211> LENGTH: 22
<212> TYPE: RNA
<213> ORGANISM: Rattus sp.

<400> SEQUENCE: 698
uacaguacug ugauaacuga ag                                            22

<210> SEQ ID NO 699
<211> LENGTH: 23
<212> TYPE: RNA
<213> ORGANISM: Rattus sp.

<400> SEQUENCE: 699
agcagcauug uacagggcua uga                                           23

<210> SEQ ID NO 700
<211> LENGTH: 21
<212> TYPE: RNA
<213> ORGANISM: Rattus sp.

<400> SEQUENCE: 700
uaaagugcug acagugcaga u                                    21

<210> SEQ ID NO 701
<211> LENGTH: 23
<212> TYPE: RNA
<213> ORGANISM: Rattus sp.

<400> SEQUENCE: 701
agcagcauug uacagggcua uca                                  23

<210> SEQ ID NO 702
<211> LENGTH: 23
<212> TYPE: RNA
<213> ORGANISM: Rattus sp.

<400> SEQUENCE: 702
uggaguguga caauguguu ugu                                   23

<210> SEQ ID NO 703
<211> LENGTH: 22
<212> TYPE: RNA
<213> ORGANISM: Rattus sp.

<400> SEQUENCE: 703
uuaaggcacg cggugaaugc ca                                   22

<210> SEQ ID NO 704
<211> LENGTH: 23
<212> TYPE: RNA
<213> ORGANISM: Rattus sp.

<400> SEQUENCE: 704
ucccugagac ccuuuaaccu gug                                  23

<210> SEQ ID NO 705
<211> LENGTH: 22
<212> TYPE: RNA
<213> ORGANISM: Rattus sp.

<400> SEQUENCE: 705
ucccugagac ccuaacuugu ga                                   22

<210> SEQ ID NO 706
<211> LENGTH: 21
<212> TYPE: RNA
<213> ORGANISM: Rattus sp.

<400> SEQUENCE: 706
cauuauuacu uuugguacgc g                                    21

<210> SEQ ID NO 707
<211> LENGTH: 21
<212> TYPE: RNA
<213> ORGANISM: Rattus sp.

<400> SEQUENCE: 707
ucguaccgug aguaauaaug c                                    21

<210> SEQ ID NO 708
<211> LENGTH: 22
<212> TYPE: RNA
<213> ORGANISM: Rattus sp.

<400> SEQUENCE: 708
ucggauccgu cugagcuugg cu                                                22

<210> SEQ ID NO 709
<211> LENGTH: 22
<212> TYPE: RNA
<213> ORGANISM: Rattus sp.

<400> SEQUENCE: 709
ucacagugaa ccggucucuu uu                                                22

<210> SEQ ID NO 710
<211> LENGTH: 22
<212> TYPE: RNA
<213> ORGANISM: Rattus sp.

<400> SEQUENCE: 710
ucacagugaa ccggucucuu uc                                                22

<210> SEQ ID NO 711
<211> LENGTH: 20
<212> TYPE: RNA
<213> ORGANISM: Rattus sp.

<400> SEQUENCE: 711
cagugcaaug uuaaaagggc                                                   20

<210> SEQ ID NO 712
<211> LENGTH: 22
<212> TYPE: RNA
<213> ORGANISM: Rattus sp.

<400> SEQUENCE: 712
cagugcaaug augaaagggc au                                                22

<210> SEQ ID NO 713
<211> LENGTH: 22
<212> TYPE: RNA
<213> ORGANISM: Rattus sp.

<400> SEQUENCE: 713
uaacagucua cagccauggu cg                                                22

<210> SEQ ID NO 714
<211> LENGTH: 22
<212> TYPE: RNA
<213> ORGANISM: Rattus sp.

<400> SEQUENCE: 714
uugguccccu ucaaccagcu gu                                                22

<210> SEQ ID NO 715
<211> LENGTH: 21
<212> TYPE: RNA
<213> ORGANISM: Rattus sp.

<400> SEQUENCE: 715
ugugacuggu ugaccagagg g                                                 21

<210> SEQ ID NO 716
<211> LENGTH: 23
<212> TYPE: RNA
<213> ORGANISM: Rattus sp.

```
<400> SEQUENCE: 716
uauggcuuuu uauuccuaug uga                                          23

<210> SEQ ID NO 717
<211> LENGTH: 23
<212> TYPE: RNA
<213> ORGANISM: Rattus sp.

<400> SEQUENCE: 717
acuccauuug uuuugaugau gga                                          23

<210> SEQ ID NO 718
<211> LENGTH: 22
<212> TYPE: RNA
<213> ORGANISM: Rattus sp.

<400> SEQUENCE: 718
uauugcuuaa gaauacgcgu ag                                           22

<210> SEQ ID NO 719
<211> LENGTH: 17
<212> TYPE: RNA
<213> ORGANISM: Rattus sp.

<400> SEQUENCE: 719
agcugguguu gugaauc                                                 17

<210> SEQ ID NO 720
<211> LENGTH: 18
<212> TYPE: RNA
<213> ORGANISM: Rattus sp.

<400> SEQUENCE: 720
ucuacagugc acgugucu                                                18

<210> SEQ ID NO 721
<211> LENGTH: 21
<212> TYPE: RNA
<213> ORGANISM: Rattus sp.

<400> SEQUENCE: 721
aacacugucu gguaaagaug g                                            21

<210> SEQ ID NO 722
<211> LENGTH: 20
<212> TYPE: RNA
<213> ORGANISM: Rattus sp.

<400> SEQUENCE: 722
cauaaaguag aaagcacuac                                              20

<210> SEQ ID NO 723
<211> LENGTH: 23
<212> TYPE: RNA
<213> ORGANISM: Rattus sp.

<400> SEQUENCE: 723
uguaguguuu ccuacuuuau gga                                          23

<210> SEQ ID NO 724
<211> LENGTH: 22
<212> TYPE: RNA
<213> ORGANISM: Rattus sp.
```

-continued

```
<400> SEQUENCE: 724
ugagaugaag cacuguagcu ca                                             22

<210> SEQ ID NO 725
<211> LENGTH: 22
<212> TYPE: RNA
<213> ORGANISM: Rattus sp.

<400> SEQUENCE: 725
uacaguauag augauguacu ag                                             22

<210> SEQ ID NO 726
<211> LENGTH: 24
<212> TYPE: RNA
<213> ORGANISM: Rattus sp.

<400> SEQUENCE: 726
guccaguuuu cccaggaauc ccuu                                           24

<210> SEQ ID NO 727
<211> LENGTH: 22
<212> TYPE: RNA
<213> ORGANISM: Rattus sp.

<400> SEQUENCE: 727
ugagaacuga auuccauggg uu                                             22

<210> SEQ ID NO 728
<211> LENGTH: 22
<212> TYPE: RNA
<213> ORGANISM: Rattus sp.

<400> SEQUENCE: 728
ucucccaacc cuuguaccag ug                                             22

<210> SEQ ID NO 729
<211> LENGTH: 21
<212> TYPE: RNA
<213> ORGANISM: Rattus sp.

<400> SEQUENCE: 729
ucagugcaug acagaacuug g                                              21

<210> SEQ ID NO 730
<211> LENGTH: 20
<212> TYPE: RNA
<213> ORGANISM: Rattus sp.

<400> SEQUENCE: 730
uugcauaguc acaaaaguga                                                20

<210> SEQ ID NO 731
<211> LENGTH: 22
<212> TYPE: RNA
<213> ORGANISM: Rattus sp.

<400> SEQUENCE: 731
uagguuaucc guguugccuu cg                                             22

<210> SEQ ID NO 732
<211> LENGTH: 22
<212> TYPE: RNA
```

```
<213> ORGANISM: Rattus sp.

<400> SEQUENCE: 732
aacauucaac cugucgguga gu                                        22

<210> SEQ ID NO 733
<211> LENGTH: 23
<212> TYPE: RNA
<213> ORGANISM: Rattus sp.

<400> SEQUENCE: 733
aacauucaac gcugucggug agu                                       23

<210> SEQ ID NO 734
<211> LENGTH: 24
<212> TYPE: RNA
<213> ORGANISM: Rattus sp.

<400> SEQUENCE: 734
aacauucauu gcugucggug gguu                                      24

<210> SEQ ID NO 735
<211> LENGTH: 23
<212> TYPE: RNA
<213> ORGANISM: Rattus sp.

<400> SEQUENCE: 735
uauggcacug guagaauuca cug                                       23

<210> SEQ ID NO 736
<211> LENGTH: 22
<212> TYPE: RNA
<213> ORGANISM: Rattus sp.

<400> SEQUENCE: 736
uggacggaga acugauaagg gu                                        22

<210> SEQ ID NO 737
<211> LENGTH: 18
<212> TYPE: RNA
<213> ORGANISM: Rattus sp.

<400> SEQUENCE: 737
uggagagaaa ggcaguuc                                             18

<210> SEQ ID NO 738
<211> LENGTH: 23
<212> TYPE: RNA
<213> ORGANISM: Rattus sp.

<400> SEQUENCE: 738
caaagaauuc uccuuuggg cuu                                        23

<210> SEQ ID NO 739
<211> LENGTH: 21
<212> TYPE: RNA
<213> ORGANISM: Rattus sp.

<400> SEQUENCE: 739
ucgugucuug uguugcagcc g                                         21

<210> SEQ ID NO 740
<211> LENGTH: 22
```

```
<212> TYPE: RNA
<213> ORGANISM: Rattus sp.

<400> SEQUENCE: 740
ugauauguuu gauauauuag gu                                              22

<210> SEQ ID NO 741
<211> LENGTH: 22
<212> TYPE: RNA
<213> ORGANISM: Rattus sp.

<400> SEQUENCE: 741
caacggaauc ccaaaagcag cu                                              22

<210> SEQ ID NO 742
<211> LENGTH: 21
<212> TYPE: RNA
<213> ORGANISM: Rattus sp.

<400> SEQUENCE: 742
cugaccuaug aauugacagc c                                               21

<210> SEQ ID NO 743
<211> LENGTH: 21
<212> TYPE: RNA
<213> ORGANISM: Rattus sp.

<400> SEQUENCE: 743
aacuggccua caaaguccca g                                               21

<210> SEQ ID NO 744
<211> LENGTH: 22
<212> TYPE: RNA
<213> ORGANISM: Rattus sp.

<400> SEQUENCE: 744
uguaacagca acuccaugug ga                                              22

<210> SEQ ID NO 745
<211> LENGTH: 21
<212> TYPE: RNA
<213> ORGANISM: Rattus sp.

<400> SEQUENCE: 745
uagcagcaca gaaauauugg c                                               21

<210> SEQ ID NO 746
<211> LENGTH: 21
<212> TYPE: RNA
<213> ORGANISM: Rattus sp.

<400> SEQUENCE: 746
uagguaguuu cauguuguug g                                               21

<210> SEQ ID NO 747
<211> LENGTH: 23
<212> TYPE: RNA
<213> ORGANISM: Rattus sp.

<400> SEQUENCE: 747
cccaguguuc agacuaccug uuc                                             23

<210> SEQ ID NO 748
```

```
<211> LENGTH: 22
<212> TYPE: RNA
<213> ORGANISM: Rattus sp.

<400> SEQUENCE: 748
aauacugccg gguaaugaug ga                                              22

<210> SEQ ID NO 749
<211> LENGTH: 22
<212> TYPE: RNA
<213> ORGANISM: Rattus sp.

<400> SEQUENCE: 749
uaacacuguc ugguaacgau gu                                              22

<210> SEQ ID NO 750
<211> LENGTH: 24
<212> TYPE: RNA
<213> ORGANISM: Rattus sp.

<400> SEQUENCE: 750
cucuaauacu gccugguaau gaug                                            24

<210> SEQ ID NO 751
<211> LENGTH: 22
<212> TYPE: RNA
<213> ORGANISM: Rattus sp.

<400> SEQUENCE: 751
gugaaauguu uaggaccacu ag                                              22

<210> SEQ ID NO 752
<211> LENGTH: 22
<212> TYPE: RNA
<213> ORGANISM: Rattus sp.

<400> SEQUENCE: 752
uucccuuugu cauccaugc cu                                               22

<210> SEQ ID NO 753
<211> LENGTH: 22
<212> TYPE: RNA
<213> ORGANISM: Rattus sp.

<400> SEQUENCE: 753
uccuucauuc caccggaguc ug                                              22

<210> SEQ ID NO 754
<211> LENGTH: 22
<212> TYPE: RNA
<213> ORGANISM: Rattus sp.

<400> SEQUENCE: 754
uggaauguaa ggaagugugu gg                                              22

<210> SEQ ID NO 755
<211> LENGTH: 22
<212> TYPE: RNA
<213> ORGANISM: Rattus sp.

<400> SEQUENCE: 755
auaagacgag caaaaagcuu gu                                              22
```

```
<210> SEQ ID NO 756
<211> LENGTH: 21
<212> TYPE: RNA
<213> ORGANISM: Rattus sp.

<400> SEQUENCE: 756
cugugcgugu gacagcggcu g                                                    21

<210> SEQ ID NO 757
<211> LENGTH: 22
<212> TYPE: RNA
<213> ORGANISM: Rattus sp.

<400> SEQUENCE: 757
uucccuuugu cauccuugc cu                                                    22

<210> SEQ ID NO 758
<211> LENGTH: 21
<212> TYPE: RNA
<213> ORGANISM: Rattus sp.

<400> SEQUENCE: 758
uaacagucuc cagucacggc c                                                    21

<210> SEQ ID NO 759
<211> LENGTH: 22
<212> TYPE: RNA
<213> ORGANISM: Rattus sp.

<400> SEQUENCE: 759
accaucgacc guugauugua cc                                                   22

<210> SEQ ID NO 760
<211> LENGTH: 21
<212> TYPE: RNA
<213> ORGANISM: Rattus sp.

<400> SEQUENCE: 760
acagcaggca cagacaggca g                                                    21

<210> SEQ ID NO 761
<211> LENGTH: 21
<212> TYPE: RNA
<213> ORGANISM: Rattus sp.

<400> SEQUENCE: 761
uaaucucagc uggcaacugu g                                                    21

<210> SEQ ID NO 762
<211> LENGTH: 24
<212> TYPE: RNA
<213> ORGANISM: Rattus sp.

<400> SEQUENCE: 762
uacugcauca ggaacugacu ggau                                                 24

<210> SEQ ID NO 763
<211> LENGTH: 21
<212> TYPE: RNA
<213> ORGANISM: Rattus sp.

<400> SEQUENCE: 763
uugugcuuga ucuaaccaug u                                                    21
```

```
<210> SEQ ID NO 764
<211> LENGTH: 21
<212> TYPE: RNA
<213> ORGANISM: Rattus sp.

<400> SEQUENCE: 764
ugauugucca aacgcaauuc u                                              21

<210> SEQ ID NO 765
<211> LENGTH: 23
<212> TYPE: RNA
<213> ORGANISM: Rattus sp.

<400> SEQUENCE: 765
agcuacauug ucugcugggu uuc                                            23

<210> SEQ ID NO 766
<211> LENGTH: 24
<212> TYPE: RNA
<213> ORGANISM: Rattus sp.

<400> SEQUENCE: 766
agcuacaucu ggcuacuggg ucuc                                           24

<210> SEQ ID NO 767
<211> LENGTH: 21
<212> TYPE: RNA
<213> ORGANISM: Rattus sp.

<400> SEQUENCE: 767
ugucaguuug ucaaauaccc c                                              21

<210> SEQ ID NO 768
<211> LENGTH: 23
<212> TYPE: RNA
<213> ORGANISM: Rattus sp.

<400> SEQUENCE: 768
cucaaacuau gggggcacuu uuu                                            23

<210> SEQ ID NO 769
<211> LENGTH: 22
<212> TYPE: RNA
<213> ORGANISM: Rattus sp.

<400> SEQUENCE: 769
caucaaagug gaggcccucu cu                                             22

<210> SEQ ID NO 770
<211> LENGTH: 23
<212> TYPE: RNA
<213> ORGANISM: Rattus sp.

<400> SEQUENCE: 770
aaagugcuuc cacuuugugu gcc                                            23

<210> SEQ ID NO 771
<211> LENGTH: 22
<212> TYPE: RNA
<213> ORGANISM: Rattus sp.

<400> SEQUENCE: 771
acucaaacug ggggcucuuu ug                                             22
```

<210> SEQ ID NO 772
<211> LENGTH: 23
<212> TYPE: RNA
<213> ORGANISM: Rattus sp.

<400> SEQUENCE: 772
aagugccgcc agguuugag ugu                                              23

<210> SEQ ID NO 773
<211> LENGTH: 21
<212> TYPE: RNA
<213> ORGANISM: Rattus sp.

<400> SEQUENCE: 773 agggccccccc cucaauccug u                                              21

<210> SEQ ID NO 774
<211> LENGTH: 23
<212> TYPE: RNA
<213> ORGANISM: Rattus sp.

<400> SEQUENCE: 774
auguaugugu gcauguaugc aug                                             23

<210> SEQ ID NO 775
<211> LENGTH: 22
<212> TYPE: RNA
<213> ORGANISM: Rattus sp.

<400> SEQUENCE: 775
ggcagaggag ggcuguucuu cc                                              22

<210> SEQ ID NO 776
<211> LENGTH: 22
<212> TYPE: RNA
<213> ORGANISM: Rattus sp.

<400> SEQUENCE: 776
ugguuuaccg ucccacauac au                                              22

<210> SEQ ID NO 777
<211> LENGTH: 22
<212> TYPE: RNA
<213> ORGANISM: Rattus sp.

<400> SEQUENCE: 777
uaugcaaggg caagcucucu uc                                              22

<210> SEQ ID NO 778
<211> LENGTH: 23
<212> TYPE: RNA
<213> ORGANISM: Rattus sp.

<400> SEQUENCE: 778
aaaagcuggg uugagagggc gaa                                             23

<210> SEQ ID NO 779
<211> LENGTH: 21
<212> TYPE: RNA
<213> ORGANISM: Rattus sp.

<400> SEQUENCE: 779

```
uaagccaggg auugugggguu c                                              21

<210> SEQ ID NO 780
<211> LENGTH: 72
<212> TYPE: DNA
<213> ORGANISM: Artificial Sequence
<220> FEATURE:
<223> OTHER INFORMATION: Description of Combined DNA/RNA Molecule:
      Synthetic oligonucleotide
<220> FEATURE:
<223> OTHER INFORMATION: Description of Artificial Sequence: Synthetic
      oligonucleotide

<400> SEQUENCE: 780
uagcagcacg uaaauauugg cggtcgtatc cagtgcaggg tccgaggtat tcgcactgga    60
tacgaccgcc aa                                                        72

<210> SEQ ID NO 781
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 781
cgcgctagca gcacgtaaat                                                 20

<210> SEQ ID NO 782
<211> LENGTH: 16
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 782
atacgaccgc caatat                                                     16

<210> SEQ ID NO 783
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 783
gtgcagggtc cga                                                        13
```